(12) United States Patent
Jefferies et al.

(10) Patent No.: US 9,150,846 B2
(45) Date of Patent: *Oct. 6, 2015

(54) P97-ANTIBODY CONJUGATES AND METHODS OF USE

(75) Inventors: Wilfred Jefferies, South Surrey (GB); Timothy Z. Vitalis, Vancouver (CA); Reinhard Gabathuler, Montreal (CA)

(73) Assignee: biOasis Technologies, Inc., Richmond (CA)

( * ) Notice: Subject to any disclaimer, the term of this patent is extended or adjusted under 35 U.S.C. 154(b) by 364 days.

This patent is subject to a terminal disclaimer.

(21) Appl. No.: 13/542,435

(22) Filed: Jul. 5, 2012

(65) Prior Publication Data

US 2013/0183368 A1    Jul. 18, 2013

Related U.S. Application Data

(60) Provisional application No. 61/504,646, filed on Jul. 5, 2011, provisional application No. 61/658,217, filed on Jun. 11, 2012.

(51) Int. Cl.
| | |
|---|---|
| A61K 47/48 | (2006.01) |
| C07K 14/79 | (2006.01) |
| C12N 9/96 | (2006.01) |
| C07K 16/32 | (2006.01) |
| C12N 9/14 | (2006.01) |
| A61K 45/06 | (2006.01) |

(52) U.S. Cl.
CPC . *C12N 9/96* (2013.01); *A61K 45/06* (2013.01); *A61K 47/4843* (2013.01); *A61K 47/48246* (2013.01); *A61K 47/48584* (2013.01); *C07K 14/79* (2013.01); *C07K 16/32* (2013.01); *C12N 9/14* (2013.01); *C12Y 306/04006* (2013.01); *C07K 2317/24* (2013.01); *C07K 2319/00* (2013.01)

(58) Field of Classification Search
CPC ...... C07K 14/705; C07K 16/00; A61K 38/00; A61K 39/00; A61K 39/395
USPC .............. 530/391.7, 391.1; 424/134.1, 179.1, 424/185.1
See application file for complete search history.

(56) References Cited

U.S. PATENT DOCUMENTS

| | | | |
|---|---|---|---|
| 4,391,904 A | 7/1983 | Litman et al. |
| 4,394,448 A | 7/1983 | Szoka, Jr. et al. |
| 4,399,216 A | 8/1983 | Axel et al. |
| 4,683,195 A | 7/1987 | Mullis et al. |
| 4,683,202 A | 7/1987 | Mullis |
| 4,704,362 A | 11/1987 | Itakura et al. |
| 4,766,075 A | 8/1988 | Goeddel et al. |
| 4,784,950 A | 11/1988 | Hagen et al. |
| 4,800,159 A | 1/1989 | Mullis et al. |
| 4,801,542 A | 1/1989 | Murray et al. |
| 4,866,042 A | 9/1989 | Neuwelt |
| 4,935,349 A | 6/1990 | McKnight et al. |
| 4,946,778 A | 8/1990 | Ladner et al. |
| 5,091,513 A | 2/1992 | Huston et al. |
| 5,132,405 A | 7/1992 | Huston et al. |
| 5,186,941 A | 2/1993 | Callahan et al. |
| 5,672,683 A | 9/1997 | Friden et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,844,093 A | 12/1998 | Kettleborough et al. |
| 5,962,012 A | 10/1999 | Lin et al. |
| 5,981,194 A | 11/1999 | Jefferies et al. |
| 6,015,557 A | 1/2000 | Tobinick et al. |
| 6,165,464 A | 12/2000 | Hudziak et al. |
| 6,177,077 B1 | 1/2001 | Tobinick |
| 6,261,595 B1 | 7/2001 | Stanley et al. |
| 6,387,371 B1 | 5/2002 | Hudziak et al. |
| 6,399,063 B1 | 6/2002 | Hudziak et al. |
| 6,419,934 B1 | 7/2002 | Tobinick |
| 6,419,944 B2 | 7/2002 | Tobinick |
| 6,455,494 B1 | 9/2002 | Jefferies et al. |
| 6,537,549 B2 | 3/2003 | Tobinick |
| 6,596,541 B2 | 7/2003 | Murphy et al. |
| 6,765,087 B1 | 7/2004 | Casterman et al. |
| 6,838,254 B1 | 1/2005 | Hamers et al. |
| 6,982,089 B2 | 1/2006 | Tobinick |
| 7,132,511 B2 | 11/2006 | Carr et al. |
| 7,138,371 B2 | 11/2006 | DeFrees et al. |
| 7,179,617 B2 | 2/2007 | DeFrees et al. |
| 7,214,658 B2 | 5/2007 | Tobinick |

(Continued)

FOREIGN PATENT DOCUMENTS

| | | |
|---|---|---|
| GB | 2188637 | 10/1987 |
| WO | WO 89/04663 | 6/1989 |
| WO | WO 93/11161 | 6/1993 |
| WO | WO 94/01463 | 1/1994 |
| WO | WO 94/13804 | 6/1994 |
| WO | WO 98/23646 | 6/1998 |
| WO | WO 00/50636 | 8/2000 |
| WO | WO 01/59459 | 8/2001 |
| WO | WO 01/83722 | 8/2001 |
| WO | WO 02/13843 | 2/2002 |

(Continued)

OTHER PUBLICATIONS

International Search Report for International Application No. PCT/US2003/00894, mailed Sep. 10, 2003.

(Continued)

*Primary Examiner* — Yan Xiao
(74) *Attorney, Agent, or Firm* — Cooley LLP

(57) ABSTRACT

The present invention provides p97-antibody conjugates and related compositions and methods, which may be used in any of a variety of therapeutic methods, including methods for the treatment of cancers such as Her2/neu-expressing and Her1/EGFR-expressing cancers.

17 Claims, 26 Drawing Sheets

(56) References Cited

U.S. PATENT DOCUMENTS

| | | | |
|---|---|---|---|
| 7,244,592 | B2 | 7/2007 | Hoogenboom et al. |
| 7,247,301 | B2 | 7/2007 | van de Winkel et al. |
| 7,462,697 | B2 | 12/2008 | Couto et al. |
| 7,595,378 | B2 | 9/2009 | van de Winkel et al. |
| 7,700,554 | B2 | 4/2010 | Beliveau et al. |
| 7,723,484 | B2 | 5/2010 | Beidler et al. |
| 7,939,072 | B2 | 5/2011 | Yarden et al. |
| 7,960,516 | B2 | 6/2011 | Matheus et al. |
| 8,546,319 | B2 | 10/2013 | Starr et al. |
| 8,722,019 | B2 | 5/2014 | Jefferies et al. |
| 2002/0119095 | A1 | 8/2002 | Gabathuler et al. |
| 2004/0055022 | A1 | 3/2004 | Cheng et al. |
| 2004/0137557 | A1 | 7/2004 | DeFrees et al. |
| 2005/0026823 | A1 | 2/2005 | Zankel et al. |
| 2005/0158296 | A1 | 7/2005 | Starr et al. |
| 2007/0167365 | A1 | 7/2007 | Beliveau et al. |
| 2008/0014188 | A1 | 1/2008 | Zankel et al. |
| 2009/0226421 | A1 | 9/2009 | Parren et al. |
| 2010/0303797 | A1 | 12/2010 | Starr et al. |
| 2011/0093962 | A1 | 4/2011 | Heidbrink et al. |
| 2012/0107302 | A1* | 5/2012 | Berry et al. ............ 424/133.1 |
| 2013/0058873 | A1 | 3/2013 | Jefferies et al. |
| 2014/0322132 | A1* | 10/2014 | Vitalis et al. ............ 424/1.69 |

FOREIGN PATENT DOCUMENTS

| | | | |
|---|---|---|---|
| WO | WO 02/13873 | 2/2002 | |
| WO | WO 03/009815 | 2/2003 | |
| WO | WO 03/057179 | 7/2003 | |
| WO | WO 2004/078215 | 9/2004 | |
| WO | WO 2006/079372 | 8/2006 | |
| WO | WO 2009/019314 | * 2/2009 | ............ C07K 14/79 |
| WO | WO 2011/044542 | 4/2011 | |
| WO | WO 2011/163649 | 12/2011 | |
| WO | WO 2013/006706 | 1/2013 | |
| WO | WO 2013/022738 | 2/2013 | |
| WO | WO 2014/022515 | 2/2014 | |
| WO | WO 2014/160438 | 10/2014 | |

OTHER PUBLICATIONS

International Preliminary Examination Report for International Application No. PCT/US2003/00894, dated Feb. 14, 2005.
Office Action for U.S. Appl. No. 13/969,280, mailed Sep. 22, 2014.
Examination Report for Australian Application No. 2012278944, dated Aug. 26, 2014.
International Preliminary Report on Patentability for International Application No. PCT/US2012/045568, dated Jan. 7, 2014.
International Search Report and Written Opinion for International Application No. PCT/US2012/045568, mailed on Sep. 27, 2012.
Notice of Allowance in U.S. Appl. No. 13/566,260, mailed Dec. 26, 2013.
Office Action in U.S. Appl. No. 13/566,260, mailed Sep. 5, 2013.
International Preliminary Report on Patentability for International Application No. PCT/US2012/049475, dated Feb. 11, 2014.
International Search Report and Written Opinion for International Application No. PCT/US2012/049475, mailed on Oct. 25, 2012.
Bickel, U. et al., "Pharmacologic effects in vivo in brain by vector-mediated peptide drug delivery," Proc. Natl. Acad. Sci. USA, 90(7):2618-2622 (1993).
Bickel, U. et al., "In vivo demonstration of subcellular localization of anti-transferrin receptor monoclonal antibody-colloidal gold conjugate in brain capillary endothelium," Journal of Histochemistry and Cytochemistry, 42(11):1493-1497 (1994).
Bickel, U. et al., "Delivery of peptides and proteins through the blood-brain barrier," Advanced Drug Delivery Review, 46(1-3):247-279 (2001).
Broadwell, R. D. et al., "Transcytosis of protein through the mammalian cerebral epithelium and endothelium. III. Receptor-mediated transcytosis through the blood-brain barrier of blood-borne transferrin and antibody against the transferrin receptor," Experimental Neurology, 142(1):47-65 (1996).
Carter, P. et al., "Humanization of an anti-p185$^{HER2}$ antibody for human cancer therapy," Proc. Natl. Acad. Sci. USA, 89:4285-4289 (1992).
Cerletti, A. et al., "Endocytosis and transcytosis of an immunoliposome-based brain drug delivery system," Journal of Drug Targeting, 8(6):435-446 (2000).
Chen, Q. et al., "Efficient Synthesis of Doxorubicin Melanotransferrin p97 Conjugates Through SMCC Linker," Synthetic Communications, 34(13) (2004).
Deguchi, Y. et al., "Retention of biologic activity of human epidermal growth factor following conjugation to a blood-brain barrier drug delivery vector via an extended poly (ethylene glycol) linker," Bioconjugate Chem., 10(1):32-37 (1999).
Delabarre, B. et al., "Central Pore Residues Mediate the p97/VCP activity required for ERAD," Molecular Cell, 19(22):451-462 (2006).
Demeule, M. et al., "High transcytosis of melanotransferrin (P97) across the blood-brain barrier," Journal of Neurochemistry, 83:924-933 (2002).
Demeule, M. et al., "Regulation of plasminogen activation: A role for melantransferrin (p97) in cell migration," Blood, 102(5):1723-1731 (2003).
Dorr, R. T. et al., "In vitro rat myocyte cardiotoxicity model for antitumor antibiotics using adenosine triphosphate/protein ratios," Cancer Research, 48:5222-5227 (1988).
Friden, P. M., "Anti-transferrin receptor antibody and antibody-drug conjugates cross the blood-brain barrier," Proc. Natl. Acad. Sci. USA, 88(11):4771-4775 (1991).
Jefferies, W. A. et al., "Transferrin receptor on endothelium of brain capillaries," Nature, 312:162-163 (1984).
Kang, Y. S. et al., "Pharmacokinetics and organ clearance of a 3'-biotinylated, internaly [32P]-labeled phosphodiester oligodeoxynucleotide coupled to a neutral avidin/monoclonal antibody conjugate," Drug Metabolism and Disposition, 23(1):55-59 (1995).
Kang, Y. S. et al., "Stability of the disulfide bond in an avidin-biotin linked chimeric peptide during in vivo transcytosis through brain endothelial cells," Journal of Drug Targeting, 8(6):425-434 (2000).
Kang, Y. S. et al., "Use of neutral avidin improves pharmacokinetics and brain delivery of biotin bound to an avidin-monoclonal antibody conjugate," Journal of Pharmacology & Experimental Therapeutics, 269(1):344-350 (1994).
Karkan, D. et al., "A Unique Carrier for Delivery of Therapeutic Compounds beyond the Blood-Brain Barrier," PLOS One, 3(6):E2469.1-E2469.14 (2008).
Moos, T. et al., "Restricted transport of anti-transferrin receptor antibody (OX26) through the blood-brain barrier in the rat," Journal of Neurochemistry, 79(1):119-129 (2001).
Moroo, I. et al. "Identification of a Novel Route of iron Transcytosis across the Mammalian Blood-Brain Barrier," Microcirculation, 10(6):457-462 (2003).
Muraszoko, K. et al., "Pharmacokinetics and toxicology of immunotoxins administered into the subarachnoid space in nonhuman primates and rodents," Cancer Research, 53(16):3752-3757 (1993).
Pardridge, W. M. et al., "Transport of human recombinant brain-derived neurotrophic factor (BDNF) through the rat blood-brain barrier in vivo using vector-mediated peptide drug delivery," Pharmaceutical Research, 11(50:738-746 (1994).
Pardridge, W. M. et al., "Vector-mediated delivery of a polyamide ("peptide") nucleic acid analogue through the blood-brain barrier in vivo," Proc. Natl. Acad. Sci. USA, 92(12):5592-5596 (1995).
Qian, Z. M. et al., "Targeted drug delivery via the transferrin receptor-mediated endocytosis pathway," Pharmacol. Rev., 54(4):561-587 (2002).
Richardson, D. R. et al., "The uptake of iron and transferrin by the human malignant melanoma cell," Biochimica et Biophysica Acta, 1053:1-12 (1990).
Rose, T. M. et al., "Primary Structure of the Human Melanoma-Associated Antigen P97 (Melanotransferrin) Deduced from the MRNA Sequence," Proc. Natl. Acad. Sci. USA, 83:1261-1265 (1986).

(56) References Cited

OTHER PUBLICATIONS

Sala, R. et al., "The Human Melanoma Associated Protein Melanotransferrin Promotes Endothelial Cell Migration and Angiogenesis in vivo," European Journal of Cell Biology, 81(11):599-607 (2002).

Shi, N. et al., "Noninvasive gene targeting to the brain," Proc. Natl. Acad. Sci. USA, 97(13):7567-7572 (2000).

Skarlatos, S. et al., "Transport of [125]transferrin through the rat blood-brain barrier," Brain Research, 683(2):164-171 (1995).

Song, B. W. et al., "Enhanced neuroprotective effects of basic fibroblast growth factor in regional brain ischemia after conjugation to a blood-brain barrier delivery vector," Journal of Pharmacology and Experimental Therapeutics, 301(2):605-610 (2002).

Tang, Y. et al., "Directing adenovirus across the blood-brain barrier via melanotransferrin (P97) transcytosis pathway in an vitro model," Gene Therapy, 14(6):523-532 (2007).

Wu, D. et al., "Pharmacokinetics and brain uptake of biotinylated basic fibroblast growth factor conjugated to a blood-brain barrier drug delivery system," Journal of Drug Targeting, 10(3):239-245 (2002).

Wu, D. et al., "Central nervous system pharmacologic effect in conscious rate after intravenous injection of a biotinylated vasoactive intestinal peptide analog coupled to a blood-brain barrier drug delivery system," Journal of Pharmacology and Experimental Therapeutics, 279(1):77-83 (1996).

Wu, D. et al., "Pharmacokinetics and blood-brain transport of [3H]-biotinylated phosphorothioate oligodeoxynucleotide conjugated to a vector-mediated drug delivery system," Journal of Pharmacology and Experimental Therapeutics, 276(1):206-211 (1996).

Yang, J. et al., "Deletion of the GPI pre-anchor sequence in human p97-a general approach for generating the soluble form of GPI-linked proteins," Protein Expression and Purification, 34(1):28-48 (2004).

Yoshikawa, T. et al., "Biotin delivery to brain with a covalent conjugate of avidin and a monoclonal antibody to the transferrin receptor," Journal of Pharmacology and Experimental Therapeutics, 263(2):897-903 (1992).

Zhang, Y. et al., "Conjugation of brain-derived neurotrophic factor to a blood-brain barrier drug targeting system enables neuroprotection in regional brain ischemia following intravenous injection of the neurotrophin," Brain Research, 889(1-2):49-56 (2001).

* cited by examiner

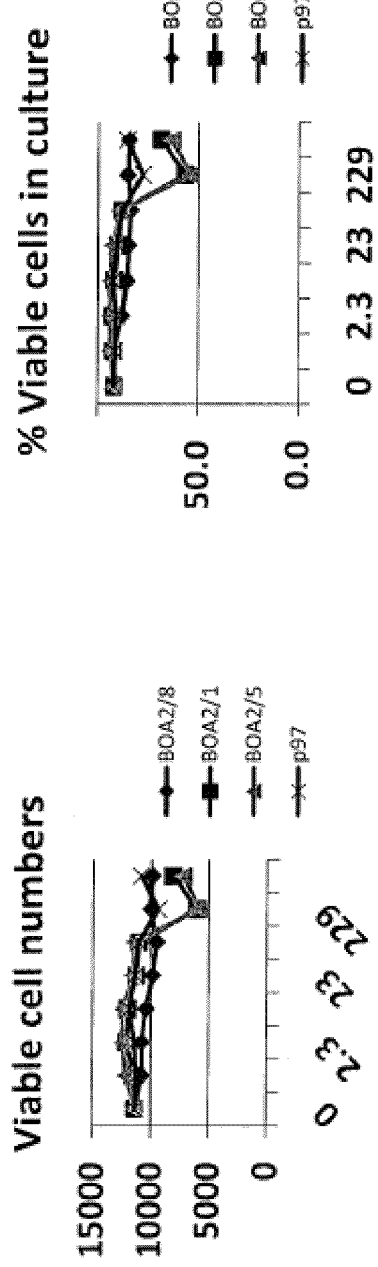
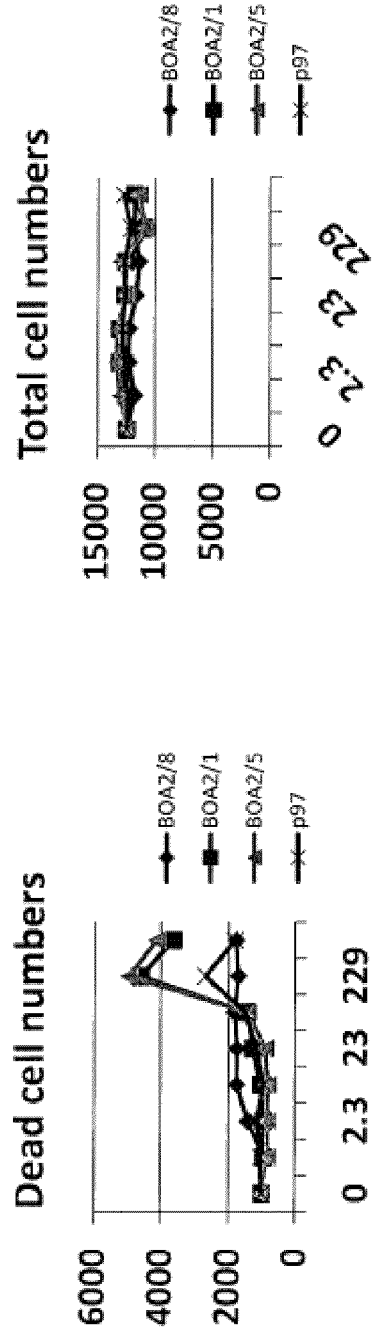
FIG. 1A
FIG. 1B
FIG. 1C
FIG. 1D
CELL LINE: BT474

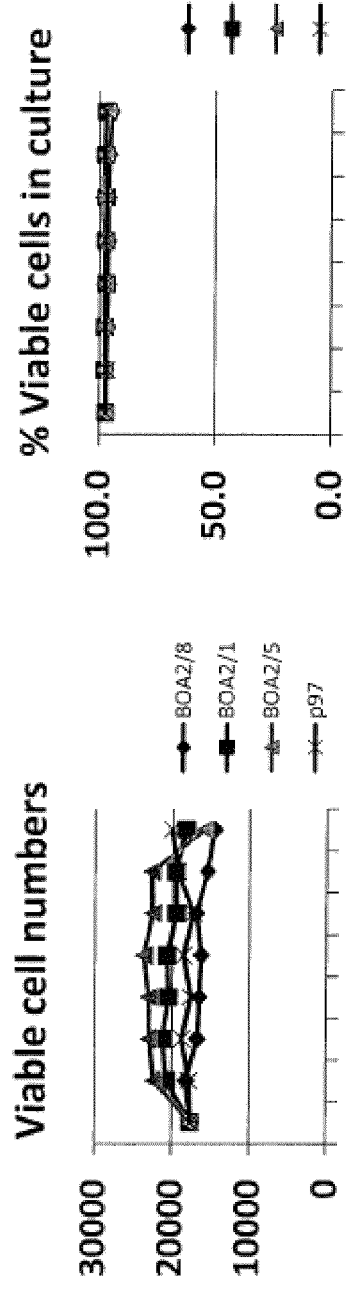
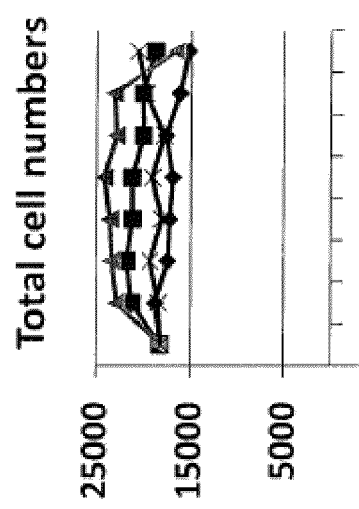
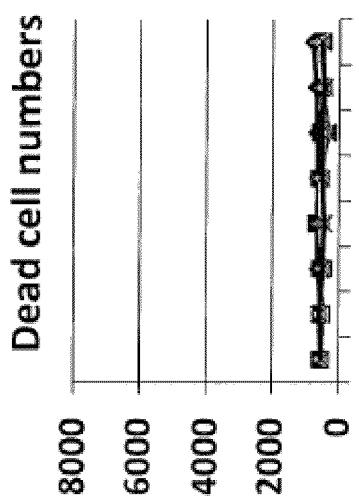
FIG. 2A, FIG. 2B, FIG. 2C, FIG. 2D
CELL LINE: MCF7-HER2

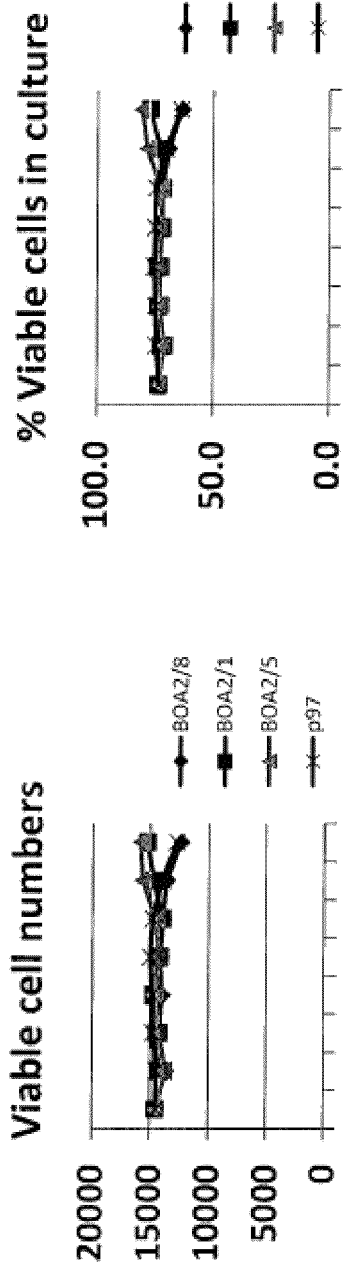
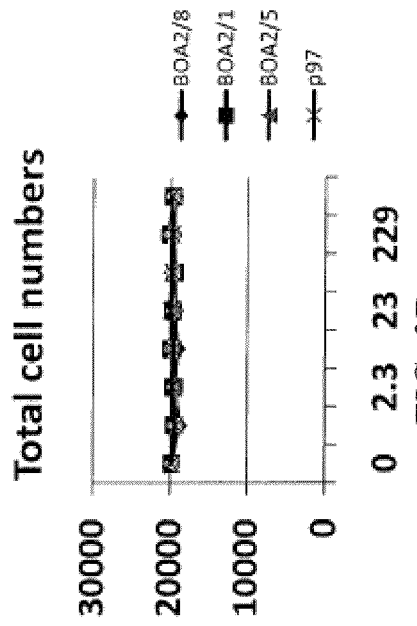
FIG. 3A
FIG. 3B
FIG. 3C
FIG. 3D
CELL LINE: MCF7-Vector

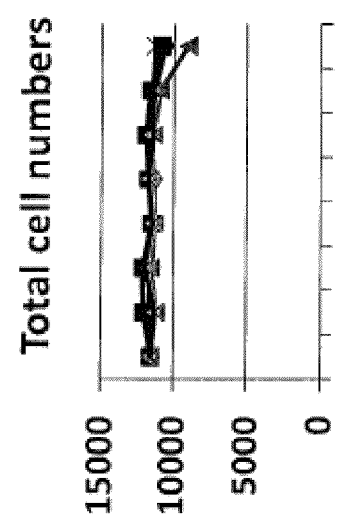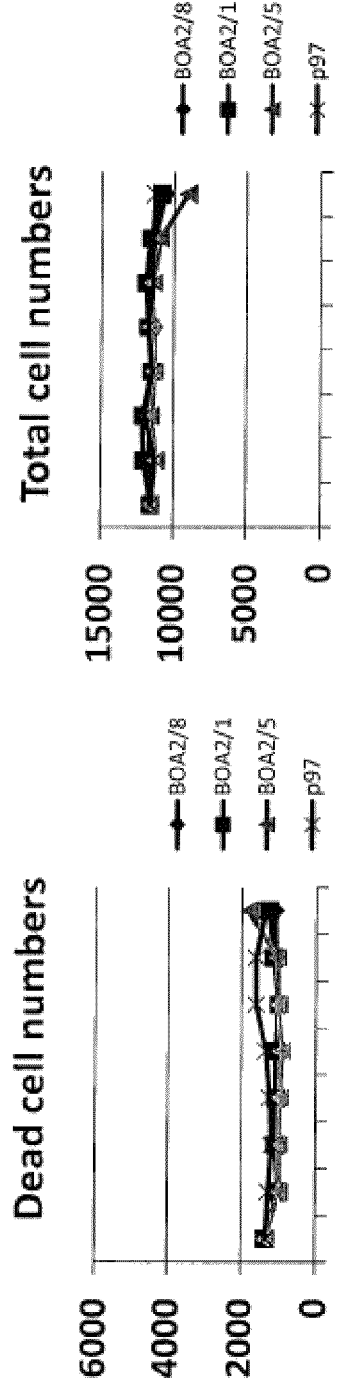
FIG. 4A  FIG. 4B  FIG. 4C  FIG. 4D
CELL LINE: SKBR3

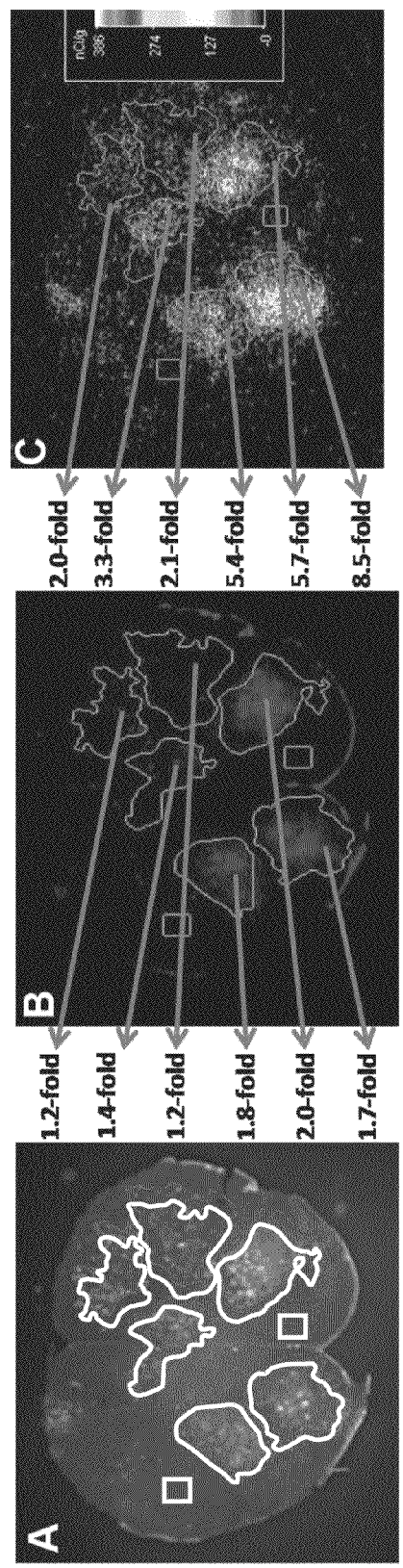

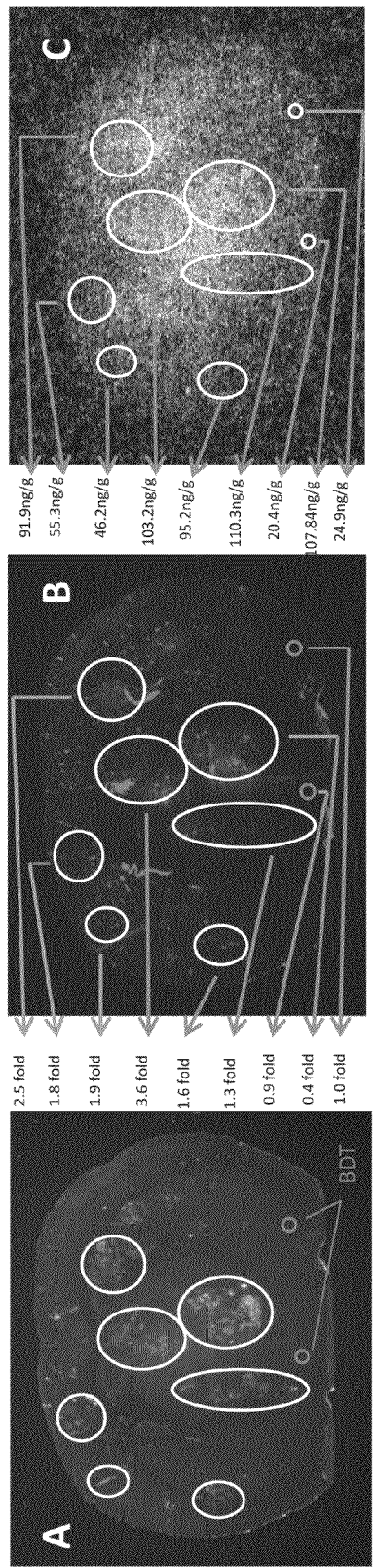

SEQUENCE LISTING

<160> NUMBER OF SEQ ID NOS: 15

<210> SEQ ID NO 1
<211> LENGTH: 738
<212> TYPE: PRT
<213> ORGANISM: Homo sapiens

<400> SEQUENCE: 1

```
Met Arg Gly Pro Ser Gly Ala Leu Trp Leu Leu Leu Ala Leu Arg Thr
1               5                   10                  15

Val Leu Gly Gly Met Glu Val Arg Trp Cys Ala Thr Ser Asp Pro Glu
            20                  25                  30

Gln His Lys Cys Gly Asn Met Ser Glu Ala Phe Arg Glu Ala Gly Ile
        35                  40                  45

Gln Pro Ser Leu Leu Cys Val Arg Gly Thr Ser Ala Asp His Cys Val
    50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95
```

-continued

```
Glu Val Tyr Asp Gln Glu Val Gly Thr Ser Tyr Ala Val Ala Val
             100                 105                 110

Val Arg Arg Ser Ser His Val Thr Ile Asp Thr Leu Lys Gly Val Lys
        115                 120                 125

Ser Cys His Thr Gly Ile Asn Arg Thr Val Gly Trp Asn Val Pro Val
    130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
                180                 185                 190

Ser Ser Gly Glu Gly Val Cys Asp Lys Ser Pro Leu Glu Arg Tyr Tyr
        195                 200                 205

Asp Tyr Ser Gly Ala Phe Arg Cys Leu Ala Glu Gly Ala Gly Asp Val
    210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
                260                 265                 270

Leu Ala Arg Val Pro Ala His Ala Val Val Arg Ala Asp Thr Asp
        275                 280                 285

Gly Gly Leu Ile Phe Arg Leu Leu Asn Glu Gly Gln Arg Leu Phe Ser
290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
                340                 345                 350

Lys Gly Leu Leu Cys Asp Pro Asn Arg Leu Pro Pro Tyr Leu Arg Trp
            355                 360                 365

Cys Val Leu Ser Thr Pro Glu Ile Gln Lys Cys Gly Asp Met Ala Val
370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Thr Tyr
            420                 425                 430

Gly Leu Val Pro Ala Ala Gly Glu His Tyr Ala Pro Glu Asp Ser Ser
            435                 440                 445

Asn Ser Tyr Tyr Val Val Ala Val Val Arg Arg Asp Ser Ser His Ala
    450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
            500                 505                 510
```

-continued

```
Phe Phe Asn Ala Ser Cys Val Pro Val Asn Asn Pro Lys Asn Tyr Pro
            515                 520                 525

Ser Ser Leu Cys Ala Leu Cys Val Gly Asp Glu Gln Gly Arg Asn Lys
    530                 535                 540

Cys Val Gly Asn Ser Gln Glu Arg Tyr Gly Tyr Arg Gly Ala Phe
545                 550                 555                 560

Arg Cys Leu Val Glu Asn Ala Gly Asp Val Ala Phe Val Arg His Thr
                565                 570                 575

Thr Val Phe Asp Asn Thr Asn Gly His Asn Ser Glu Pro Trp Ala Ala
                580                 585                 590

Glu Leu Arg Ser Glu Asp Tyr Glu Leu Leu Cys Pro Asn Gly Ala Arg
            595                 600                 605

Ala Glu Val Ser Gln Phe Ala Ala Cys Asn Leu Ala Gln Ile Pro Pro
    610                 615                 620

His Ala Val Met Val Arg Pro Asp Thr Asn Ile Phe Thr Val Tyr Gly
625                 630                 635                 640

Leu Leu Asp Lys Ala Gln Asp Leu Phe Gly Asp His Asn Lys Asn
                645                 650                 655

Gly Phe Lys Met Phe Asp Ser Ser Asn Tyr His Gly Gln Asp Leu Leu
            660                 665                 670

Phe Lys Asp Ala Thr Val Arg Ala Val Pro Val Gly Glu Lys Thr Thr
        675                 680                 685

Tyr Arg Gly Trp Leu Gly Leu Asp Tyr Val Ala Ala Leu Glu Gly Met
    690                 695                 700

Ser Ser Gln Gln Cys Ser Gly Ala Ala Ala Pro Ala Pro Gly Ala Pro
705                 710                 715                 720

Leu Leu Pro Leu Leu Leu Pro Ala Leu Ala Arg Leu Leu Pro Pro
                725                 730                 735

Ala Leu

<210> SEQ ID NO 2
<211> LENGTH: 1255
<212> TYPE: PRT
<213> ORGANISM: Homo sapiens

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140
```

-continued

```
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
```

```
Leu Pro Cys His Pro Glu Cys Gln Pro Gln Asn Gly Ser Val Thr Cys
                 565                 570                 575

Phe Gly Pro Glu Ala Asp Gln Cys Val Ala Cys Ala His Tyr Lys Asp
             580                 585                 590

Pro Pro Phe Cys Val Ala Arg Cys Pro Ser Gly Val Lys Pro Asp Leu
             595                 600                 605

Ser Tyr Met Pro Ile Trp Lys Phe Pro Asp Glu Gly Ala Cys Gln
             610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
             645                 650                 655

Ala Val Val Gly Ile Leu Leu Val Val Val Leu Gly Val Val Phe Gly
             660                 665                 670

Ile Leu Ile Lys Arg Arg Gln Gln Lys Ile Arg Lys Tyr Thr Met Arg
             675                 680                 685

Arg Leu Leu Gln Glu Thr Glu Leu Val Glu Pro Leu Thr Pro Ser Gly
             690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
             725                 730                 735

Gly Ile Trp Ile Pro Asp Gly Glu Asn Val Lys Ile Pro Val Ala Ile
             740                 745                 750

Lys Val Leu Arg Glu Asn Thr Ser Pro Lys Ala Asn Lys Glu Ile Leu
             755                 760                 765

Asp Glu Ala Tyr Val Met Ala Gly Val Gly Ser Pro Tyr Val Ser Arg
             770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
             805                 810                 815

Leu Gly Ser Gln Asp Leu Leu Asn Trp Cys Met Gln Ile Ala Lys Gly
             820                 825                 830

Met Ser Tyr Leu Glu Asp Val Arg Leu Val His Arg Asp Leu Ala Ala
             835                 840                 845

Arg Asn Val Leu Val Lys Ser Pro Asn His Val Lys Ile Thr Asp Phe
             850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
             885                 890                 895

Arg Arg Phe Thr His Gln Ser Asp Val Trp Ser Tyr Gly Val Thr Val
             900                 905                 910

Trp Glu Leu Met Thr Phe Gly Ala Lys Pro Tyr Asp Gly Ile Pro Ala
             915                 920                 925

Arg Glu Ile Pro Asp Leu Leu Glu Lys Gly Glu Arg Leu Pro Gln Pro
             930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
             965                 970                 975
```

| | | | | | | | | | | | | |
|---|---|---|---|---|---|---|---|---|---|---|---|---|
|Ser|Arg|Met|Ala|Arg|Asp|Pro|Gln|Arg|Phe|Val|Val|Ile|Gln|Asn|Glu|
| | |980| | | |985| | | |990| | |
|Asp|Leu|Gly|Pro|Ala|Ser|Pro|Leu|Asp|Ser|Thr|Phe|Tyr|Arg|Ser|Leu|
| | |995| | | |1000| | | |1005| | |
|Leu|Glu|Asp|Asp|Asp|Met|Gly|Asp|Leu|Val|Asp|Ala|Glu|Glu|Tyr|
| | |1010| | | |1015| | | |1020| | |
|Leu|Val|Pro|Gln|Gln|Gly|Phe|Phe|Cys|Pro|Asp|Pro|Ala|Pro|Gly|
| | |1025| | | |1030| | | |1035| | |
|Ala|Gly|Gly|Met|Val|His|His|Arg|His|Arg|Ser|Ser|Thr|Arg|
| | |1040| | | |1045| | | |1050| | |
|Ser|Gly|Gly|Gly|Asp|Leu|Thr|Leu|Gly|Leu|Glu|Pro|Ser|Glu|Glu|
| | |1055| | | |1060| | | |1065| | |
|Glu|Ala|Pro|Arg|Ser|Pro|Leu|Ala|Pro|Ser|Glu|Gly|Ala|Gly|Ser|
| | |1070| | | |1075| | | |1080| | |
|Asp|Val|Phe|Asp|Gly|Asp|Leu|Gly|Met|Gly|Ala|Ala|Lys|Gly|Leu|
| | |1085| | | |1090| | | |1095| | |
|Gln|Ser|Leu|Pro|Thr|His|Asp|Pro|Ser|Pro|Leu|Gln|Arg|Tyr|Ser|
| | |1100| | | |1105| | | |1110| | |
|Glu|Asp|Pro|Thr|Val|Pro|Leu|Pro|Ser|Glu|Thr|Asp|Gly|Tyr|Val|
| | |1115| | | |1120| | | |1125| | |
|Ala|Pro|Leu|Thr|Cys|Ser|Pro|Gln|Pro|Glu|Tyr|Val|Asn|Gln|Pro|
| | |1130| | | |1135| | | |1140| | |
|Asp|Val|Arg|Pro|Gln|Pro|Pro|Ser|Pro|Arg|Glu|Gly|Pro|Leu|Pro|
| | |1145| | | |1150| | | |1155| | |
|Ala|Ala|Arg|Pro|Ala|Gly|Ala|Thr|Leu|Glu|Arg|Pro|Lys|Thr|Leu|
| | |1160| | | |1165| | | |1170| | |
|Ser|Pro|Gly|Lys|Asn|Gly|Val|Val|Lys|Asp|Val|Phe|Ala|Phe|Gly|
| | |1175| | | |1180| | | |1185| | |
|Gly|Ala|Val|Glu|Asn|Pro|Glu|Tyr|Leu|Thr|Pro|Gln|Gly|Gly|Ala|
| | |1190| | | |1195| | | |1200| | |
|Ala|Pro|Gln|Pro|His|Pro|Pro|Ala|Phe|Ser|Pro|Ala|Phe|Asp|
| | |1205| | | |1210| | | |1215| | |
|Asn|Leu|Tyr|Tyr|Trp|Asp|Gln|Asp|Pro|Pro|Glu|Arg|Gly|Ala|Pro|
| | |1220| | | |1225| | | |1230| | |
|Pro|Ser|Thr|Phe|Lys|Gly|Thr|Pro|Thr|Ala|Glu|Asn|Pro|Glu|Tyr|
| | |1235| | | |1240| | | |1245| | |
|Leu|Gly|Leu|Asp|Val|Pro|Val|
| | |1250| | | |1255|

<210> SEQ ID NO 3
<211> LENGTH: 3963
<212> TYPE: DNA
<213> ORGANISM: Homo sapiens

<400> SEQUENCE: 3

```
cacttaagga gctcgggcca gcgcgagggg gagcagggag gaagcccggc tgctgcggac    60
ctcctcggac ccggacccag ccccagcccg gccccagcca gccccgacgg cgccatgcgg   120
ggtccgagcg gggctctgtg gctgctcctg gctctgcgca ccgtgctcgg tggcatggag   180
gtgcggtggt gcgccaccct ggacccagag cagcacaagt gcggcaacat gagcgaggcc   240
ttccgggaag cgggcatcca gcctccctc ctctgcgtcc ggggcacctc cgccgaccac   300
tgcgtccagc tcatcgcggc ccaggaggct gacgccatca ctctggatgg aggagccatc   360
tatgaggcgg gaaaggagca cggcctgaag ccggtggtgg cgaagtgta cgatcaagag   420
```

-continued

```
gtcggtacct cctattacgc cgtggctgtg gtcaggagga gctcccatgt gaccattgac      480
accctgaaag gcgtgaagtc ctgccacacg ggcatcaatc gcacagtggg ctggaacgtg      540
cccgtgggct acctggtgga gagcggccgc ctctcggtga tgggctgcga tgtactcaaa      600
gctgtcagcg actattttgg gggcagctgc gtcccggggg caggagagac cagttactct      660
gagtccctct gtcgcctctg caggggtgac agctctgggg aaggggtgtg tgacaagagc      720
cccctggaga gatactacga ctacagcggg gccttccggt gcctggcgga aggggcaggg      780
gacgtggctt ttgtgaagca cagcacggta ctggagaaca cggatgggaa gacgcttccc      840
tcctggggcc aggccctgct gtcacaggac ttcgagctgc tgtgccggga tggtagccgg      900
gccgatgtca ccgagtggag gcagtgccat ctggcccggg tgcctgctca cgccgtggtg      960
gtccgggccg acacagatgg gggcctcatc ttccggctgc tcaacgaagg ccagcgtctg     1020
ttcagccacg agggcagcag cttccagatg ttcagctctg aggcctatgg ccagaaggat     1080
ctactcttca aagactctac ctcggagctt gtgcccatcg ccacacagac ctatgaggcg     1140
tggctgggcc atgagtacct gcacgccatg aagggtctgc tctgtgaccc caaccggctg     1200
cccccctacc tgcgctggtg tgtgctctcc actcccgaga tccagaagtg tggagacatg     1260
gccgtggcct tccgccggca gcggctcaag ccagagatcc agtgcgtgtc agccaagtcc     1320
ccccaacact gcatggagcg gatccaggct gagcaggtcg acgctgtgac cctgagtggc     1380
gaggacattt acacgcgggg gaagacgtac ggcctggttc ccgcagccgg ggagcactat     1440
gccccggaag acagcagcaa ctcgtactac gtggtggccg tggtgagacg ggacagctcc     1500
cacgccttca ccttggatga gcttcggggc aagcgctcct gccacgccgg tttcggcagc     1560
cctgcaggct gggatgtccc cgtgggtgcc cttattcaga gaggcttcat ccggcccaag     1620
gactgtgacg tcctcacagc agtgagcgag ttcttcaatg ccagctgcgt gcccgtgaac     1680
aaccccaaga actacccctc ctcgctgtgt gcactgtgcg tgggggacga gcagggccgc     1740
aacaagtgtg tgggcaacag ccaggagcgg tattacggct accgcggcgc cttcaggtgc     1800
ctggtggaga atgcgggtga cgttgccttc gtcaggcaca caaccgtctt tgacaacaca     1860
aacggccaca attccgagcc ctgggctgct gagctcaggt cagaggacta tgaactgctg     1920
tgccccaacg gggcccgagc cgaggtgtcc cagtttgcag cctgcaacct ggcacagata     1980
ccaccccacg ccgtgatggt ccggcccgac accaacatct tcaccgtgta tggactgctg     2040
gacaaggccc aggacctgtt tggagacgac cacaataaga acgggttcaa aatgttcgac     2100
tcctccaact atcatggcca agacctgctt ttcaaggatg ccaccgtccg ggcggtgcct     2160
gtcggagaga aaaccaccta ccgcggctgg ctggggctgg actacgtggc ggcgctggaa     2220
gggatgtcgt ctcagcagtg ctcgggcgca gcggccccgg cgcccgggc gcccctgctc     2280 ccgctgctgc tgcccgccct cgccgcccgc ctgctcccgc ccgccctctg agcccggccg     2340
ccccgcccca gagctccgat gcccgccggg ggagtttccg cggcggcttc gcgctggaat     2400
ccagaaggaa gctcgcgaag gccgggcccg gcgtgggcgg gagcaggcgc ctccccggga     2460
gccccgccgc ccacgggcgc cacctggcgc tgctacctga ggcgccgccc ccgggcccgc     2520
gcggcccttc ccgccaaccg ccgcctcccg ccacctggag ccgcgcgggc cgcgccgagc     2580
gaggccggtt gcccaggaaa ccgctgagtc cgggcttccc gccgcccgcc ccgcggtgtc     2640
gcccgagggg cccgcccgcc tcctccccgc agcccgcgcc cccgtccgc gaggcccct     2700 ggggacgcgt tggccgccga ggcgcctaca cccgcaggcc gcggccaggc cgtcccagga     2760
ggccccggcg ccaacgggac ccggcgcgtg ggacagcggc ctctgctggc ggcggcggga     2820
```

```
gggaggccgg accggggcga cggggagaag ccttcgcccg cgggaccgtg tccggggtgg    2880
gggctccagt tcctccgacc gcccgtgcgc tgggagggag gccgagcccg ggaacgccg     2940 cgtgccctgc ctcgtccccc actgtggccg cgccagctcc atcccgggcc agccgcgtcc    3000
acgggccccc tcccgagtct cctcaggctc tcgcctcccc tacccccgtg ggatgccac     3060 cgcccgcacc cacgcccgag cctggcggca gcagccgccc ccgcctgaa gggagccgga    3120 ggtgacccag gccgcgggct cccgaggccc ctgaagggct cgcgcgtggg acccgccatg   3180
cttctgggtt ccgaacgggg gtgagctccg tctcctcacc cggccccgca cccgctgggc    3240
ctggggaccc ctcactcccc gtgcccgccc tccgcgagg cagcagaaag cgccggccg     3300 gggcctctct ctactccatc ttgccacagt tgtctgagaa gccagaaaaa gtttccagaa    3360
ctggcagccc ttaaaaaaaa tgaagaggaa gagaagaaat gggagcaggc agccctcgtc    3420
agcagaccgg gagccgcgtg ggcgcggagc catttgcatt ccggtctgcg ggggctcggg    3480
gatgctggtg acaggcccgg ttccggtgg ctcgccccca cctgcgggcg tcggaagga    3540 tcccttccat ctctcagccg cagaggaggc cctggcagcg ccccggctgt agccatgcaa   3600
ccccgaggag tcccgggcac cttcaccca ccgggagggg ccacaaggac ctgggcctcg   3660
gccaccaagc tttgtcccct ctcgctgtgg ggggctagtg attctcctcc gacctgacga    3720
ttgcttggtt ttttcaaaag ggagttttgt gcggtgagaa gtgtgtttct gtgtggctaa    3780
ctctgggcta gcgtgccgtg gccattgaag gtgtggcctg cgtgggtgca gtgtaagtga    3840
cgctggattg tcaggtggca gcaggggacc cctgctgtgt cagtgctaat gaaacatgtt    3900
ggttggtttc taaaataaag ccaaacaagc cagcacatgc agaggcttgg accctgatag    3960
aaa                                                                  3963

<210> SEQ ID NO 4
<211> LENGTH: 4624
<212> TYPE: DNA
<213> ORGANISM: Homo sapiens

<400> SEQUENCE: 4
ggaggaggtg gaggaggagg gctgcttgag gaagtataag aatgaagttg tgaagctgag      60
attcccctcc attgggaccg gagaaaccag gggagccccc cgggcagccg cgcgcccctt     120
cccacggggc cctttactgc gccgcgcgcc cggcccccac ccctcgcagc accccgcgcc    180
ccgcgccctc ccagccgggt ccagccggag ccatggggcc ggagccgcag tgagcaccat    240
ggagctggcg gccttgtgcc gctgggggct cctcctcgcc ctcttgcccc cggagccgc     300 gagcacccaa gtgtgcaccg gcacagacat gaagctgcgg ctccctgcca gtcccgagac    360
ccacctggac atgctccgcc acctctacca gggctgccag gtggtgcagg gaaacctgga    420
actcacctac ctgcccacca atgccagcct gtccttcctg caggatatcc aggaggtgca    480
gggctacgtg ctcatcgctc acaaccaagt gaggcaggtc ccactgcaga ggctgcggat    540
tgtgcgaggc acccagctct ttgaggacaa ctatgccctg gccgtgctag acaatggaga    600
cccgctgaac aataccaccc ctgtcacagg ggcctcccca ggaggcctgc gggagctgca    660
gcttcgaagc ctcacagaga tcttgaaagg aggggtcttg atccagcgga accccccagc    720
ctgctaccag gacacgattt gtggaaggac atcttccac aagaacaacc agctggctct    780
cacactgata gacaccaacc gctctcgggc ctgccaccc tgttctccga tgtgtaaggg    840
ctcccgctgc tggggagaga gttctgagga ttgtcagagc ctgacgcgca ctgtctgtgc    900
cggtggctgt gcccgctgca aggggccact gcccactgac tgctgccatg agcagtgtgc    960
```

```
tgccggctgc acgggcccca agcactctga ctgcctggcc tgcctccact tcaaccacag    1020
tggcatctgt gagctgcact gcccagccct ggtcacctac aacacagaca cgtttgagtc    1080
catgcccaat cccgagggcc ggtatacatt cggcgccagc tgtgtgactg cctgtcccta    1140
caactacctt tctacggacg tgggatcctg caccctcgtc tgcccctgc acaaccaaga     1200 ggtgacagca gaggatggaa cacagcggtg tgagaagtgc agcaagccct gtgcccgagt    1260
gtgctatggt ctgggcatgg agcacttgcg agaggtgagg gcagttacca gtgccaatat    1320
ccaggagttt gctggctgca agaagatctt tgggagcctg gcatttctgc cggagagctt    1380
tgatggggac ccagcctcca acactgcccc gctccagcca gagcagctcc aagtgtttga    1440
gactctggaa gagatcacag gttacctata catctcagca tggccggaca gcctgcctga    1500
cctcagcgtc ttccagaacc tgcaagtaat ccggggacga attctgcaca atggcgccta    1560
ctcgctgacc ctgcaagggc tgggcatcag ctggctgggg ctgcgctcac tgagggaact    1620
gggcagtgga ctgccctca tccaccataa cacccacctc tgcttcgtgc acacggtgcc     1680
ctgggaccag ctctttcgga acccgcacca agctctgctc cacactgcca accggccaga    1740
ggacgagtgt gtgggcgagg gcctggcctg ccaccagctg tgcgcccgag ggcactgctg    1800
gggtccaggg cccacccagt gtgtcaactg cagccagttc cttcggggcc aggagtgcgt    1860
ggaggaatgc cgagtactgc aggggctccc cagggagtat gtgaatgcca ggcactgttt    1920
gccgtgccac cctgagtgtc agccccagaa tggctcagtg acctgttttg gaccggaggc    1980
tgaccagtgt gtggcctgtg cccactataa ggaccctccc ttctgcgtgg cccgctgccc    2040
cagcggtgtg aaacctgacc tctcctacat gcccatctgg aagtttccag atgaggaggg    2100
cgcatgccag ccttgcccca tcaactgcac ccactcctgt gtggacctgg atgacaaggg    2160
ctgccccgcc gagcagagag ccagccctct gacgtccatc atctctgcgg tggttggcat    2220
tctgctggtc gtggtcttgg gggtggtctt tgggatcctc atcaagcgac ggcagcagaa    2280
gatccggaag tacacgatgc ggagactgct gcaggaaacg gagctggtgg agccgctgac    2340
acctagcgga gcgatgccca accaggcgca gatgcggatc ctgaaagaga cggagctgag    2400
gaaggtgaag gtgcttggat ctggcgcttt tggcacagtc tacaagggca tctggatccc    2460
tgatggggag aatgtgaaaa ttccagtggc catcaaagtg ttgagggaaa acatcccc     2520 caaagccaac aaagaaatct tagacgaagc atacgtgatg ctggtgtgg ctcccata      2580 tgtctcccgc cttctgggca tctgcctgac atccacggtg cagctggtga cacagcttat    2640
gccctatggc tgcctcttag accatgtccg ggaaaaccgc ggacgcctgg gctcccagga    2700
cctgctgaac tggtgtatgc agattgccaa ggggatgagc tacctggagg atgtgcggct    2760
cgtacacagg gacttggccg ctcggaacgt gctggtcaag agtcccaacc atgtcaaaat    2820
tacagacttc gggctggctc ggctgctgga cattgacgag acagagtacc atgcagatgg    2880
gggcaaggtg cccatcaagt ggatggcgct ggagtccatt ctccgccggc ggttcaccca    2940
ccagagtgat gtgtggagtt atggtgtgac tgtgtgggag ctgatgactt ttgggccaa    3000 accttacgat gggatcccag cccgggagat ccctgacctg ctggaaaagg gggagcggct    3060
gccccagccc cccatctgca ccattgatgt ctacatgatc atggtcaaat gttggatgat    3120
tgactctgaa tgtcggccaa gattccggga gttggtgtct gaattctccc gcatggccag    3180 ggaccccag cgctttgtgg tcatccagaa tgaggacttg ggcccagcca gtccccttgga    3240 cagcaccttc taccgctcac tgctggagga cgatgacatg ggggacctgg tggatgctga    3300
ggagtatctg gtaccccagc agggcttctt ctgtccagac cctgccccgg gcgctggggg    3360
```

```
catggtccac cacaggcacc gcagctcatc taccaggagt ggcggtgggg acctgacact    3420
agggctggag ccctctgaag aggaggcccc caggtctcca ctggcaccct ccgaaggggc    3480
tggctccgat gtatttgatg gtgacctggg aatgggggca gccaaggggc tgcaaagcct    3540
ccccacacat gaccccagcc ctctacagcg gtacagtgag gacccacag tacccctgcc     3600 ctctgagact gatggctacg ttgcccccct gacctgcagc cccagcctg aatatgtgaa     3660 ccagccagat gttcggcccc agccccttc gccccgagag ggccctctgc ctgctgcccg     3720
acctgctggt gccactctgg aaaggcccaa gactctctcc ccagggaaga atggggtcgt    3780
caaagacgtt tttgcctttg ggggtgccgt ggagaacccc gagtactga cacccccaggg   3840 aggagctgcc cctcagcccc accctcctcc tgccttcagc ccagccttcg acaacctcta   3900
ttactgggac caggacccac cagagcgggg ggctccaccc agcaccttca agggacacc    3960 tacggcagag aacccagagt acctgggtct ggacgtgcca gtgtgaacca gaaggccaag   4020
tccgcagaag ccctgatgtg tcctcaggga gcagggaagg cctgacttct gctggcatca   4080
agaggtggga gggccctccg accacttcca ggggaacctg ccatgccagg aacctgtcct   4140
aaggaaccct tccttcctgct tgagttccca gatggctgga aggggtccag cctcgttgga   4200
agaggaacag cactggggag tctttgtgga ttctgaggcc ctgcccaatg agactctagg    4260
gtccagtgga tgccacagcc cagcttggcc ctttccttcc agatcctggg tactgaaagc    4320
cttaggaaag ctggcctgag aggggaagcg gccctaaggg agtgtctaag aacaaaagcg    4380
acccattcag agactgtccc tgaaacctag tactgccccc catgaggaag gaacagcaat    4440
ggtgtcagta tccaggcttt gtacagagtg cttttctgtt tagttttac tttttttgtt    4500 ttgttttttt aaagatgaaa taaagaccca ggggagaat gggtgttgta tggggaggca    4560
agtgtggggg gtccttctcc acccactt tgtccatttg caaatatatt ttggaaaaca    4620
gcta                                                                4624

<210> SEQ ID NO 5
<211> LENGTH: 5
<212> TYPE: PRT
<213> ORGANISM: Artificial Sequence
<220> FEATURE:
<223> OTHER INFORMATION: Heterologous sulfatase motif
<220> FEATURE:
<221> NAME/KEY: MISC_FEATURE
<222> LOCATION: (1)..(1)
<223> OTHER INFORMATION: X = Any Amino Acid or may be absent
<220> FEATURE:
<221> NAME/KEY: MOD_RES
<222> LOCATION: (2)..(2)
<223> OTHER INFORMATION: C-alpha-formylglycine (FGly)
<220> FEATURE:
<221> NAME/KEY: MISC_FEATURE
<222> LOCATION: (3)..(3)
<223> OTHER INFORMATION: Xaa = Any Amino Acid
<220> FEATURE:
<221> NAME/KEY: MISC_FEATURE
<222> LOCATION: (4)..(4)
<223> OTHER INFORMATION: Xaa = Ala or Pro
<220> FEATURE:
<221> NAME/KEY: MISC_FEATURE
<222> LOCATION: (5)..(5)
<223> OTHER INFORMATION: Xaa = Any amino acid

<400> SEQUENCE: 5

Xaa Gly Xaa Xaa Xaa
1               5
```

```
<210> SEQ ID NO 6
<211> LENGTH: 5
<212> TYPE: PRT
<213> ORGANISM: Artificial Sequence
<220> FEATURE:
<223> OTHER INFORMATION: Heterologous sulfatase motif
<220> FEATURE:
<221> NAME/KEY: MISC_FEATURE
<222> LOCATION: (1)..(1)
<223> OTHER INFORMATION: Xaa = any amino acid or may be absent
<220> FEATURE:
<221> NAME/KEY: MISC_FEATURE
<222> LOCATION: (2)..(2)
<223> OTHER INFORMATION: Xaa = Cys or Ser
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Pro or Ala
<220> FEATURE:
<221> NAME/KEY: MISC_FEATURE
<222> LOCATION: (5)..(5)
<223> OTHER INFORMATION: Xaa = Any amino acid

<400> SEQUENCE: 6

Xaa Xaa Xaa Xaa Xaa
1               5

<210> SEQ ID NO 7
<211> LENGTH: 4
<212> TYPE: PRT
<213> ORGANISM: Artificial Sequence
<220> FEATURE:
<223> OTHER INFORMATION: Peptide linker

<400> SEQUENCE: 7

Gly Ser Gly Ser
1

<210> SEQ ID NO 8
<211> LENGTH: 4
<212> TYPE: PRT
<213> ORGANISM: Artificial Sequence
<220> FEATURE:
<223> OTHER INFORMATION: Peptide linker

<400> SEQUENCE: 8

Gly Gly Ser Gly
1

<210> SEQ ID NO 9
<211> LENGTH: 4
<212> TYPE: PRT
<213> ORGANISM: Artificial Sequence
<220> FEATURE:
<223> OTHER INFORMATION: Peptide linker

<400> SEQUENCE: 9

Gly Gly Gly Ser
1

<210> SEQ ID NO 10
<211> LENGTH: 5
<212> TYPE: PRT
<213> ORGANISM: Artificial Sequence
<220> FEATURE:
<223> OTHER INFORMATION: Peptide Linker
```

<400> SEQUENCE: 10

Gly Gly Gly Gly Ser
1               5

<210> SEQ ID NO 11
<211> LENGTH: 4
<212> TYPE: PRT
<213> ORGANISM: Artificial Sequence
<220> FEATURE:
<223> OTHER INFORMATION: Peptide linker

<400> SEQUENCE: 11

Gly Asn Gly Asn
1

<210> SEQ ID NO 12
<211> LENGTH: 4
<212> TYPE: PRT
<213> ORGANISM: Artificial Sequence
<220> FEATURE:
<223> OTHER INFORMATION: Peptide linker

<400> SEQUENCE: 12

Gly Gly Asn Gly
1

<210> SEQ ID NO 13
<211> LENGTH: 4
<212> TYPE: PRT
<213> ORGANISM: Artificial Sequence
<220> FEATURE:
<223> OTHER INFORMATION: Peptide linker

<400> SEQUENCE: 13

Gly Gly Gly Asn
1

<210> SEQ ID NO 14
<211> LENGTH: 5
<212> TYPE: PRT
<213> ORGANISM: Artificial Sequence
<220> FEATURE:
<223> OTHER INFORMATION: Peptide linker

<400> SEQUENCE: 14

Gly Gly Gly Gly Asn
1               5

<210> SEQ ID NO 15
<211> LENGTH: 1210
<212> TYPE: PRT
<213> ORGANISM: Homo sapiens

<400> SEQUENCE: 15

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

-continued

```
Thr Ile Gln Glu Val Ala Gly Tyr Val Leu Ile Ala Leu Asn Thr Val
                 85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
Lys Thr Gly Leu Lys Glu Leu Pro Met Arg Asn Leu Gln Glu Ile Leu
130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
```

-continued

Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
        610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
        690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
        770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
        850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910

-continued

```
Lys Pro Tyr Asp Gly Ile Pro Ala Ser Glu Ile Ser Ile Leu Glu
        915                 920                 925

Lys Gly Glu Arg Leu Pro Gln Pro Pro Ile Cys Thr Ile Asp Val Tyr
930                     935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210
```

P97-ANTIBODY CONJUGATES AND METHODS OF USE

CROSS REFERENCE TO RELATED APPLICATIONS

This application claims the benefit under 35 U.S.C. §119 (e) of U.S. Application No. 61/658,217, filed Jun. 11, 2012, and U.S. Application No. 61/504,646, filed Jul. 5, 2011, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BIOA_003_02US_ST25.txt. The text file is about 41 KB, was created on Jul. 5, 2012, and is being submitted electronically via EFS-Web.

BACKGROUND

1. Technical Field

The present invention relates generally to p97-antibody conjugates, related compositions and methods of using the same. Certain embodiments are more specifically directed to conjugates comprising a p97 polypeptide sequence and an antibody or antigen-binding fragment thereof that specifically binds to a cell surface receptor or cell surface protein, or a cancer-associated antigen, such as the human Her2/neu protein or the Her1/EGF receptor. Such antibody conjugates are useful, for example, in methods for treating a variety of diseases, including oncological diseases such as Her2/neu-expressing and Her1/EGFR-expressing cancers.

2. Description of the Related Art

Overcoming the difficulties of delivering therapeutic agents to specific regions of the brain represents a major challenge to treatment of most brain disorders. In its neuroprotective role, the blood-brain barrier (BBB) functions to hinder the delivery of many potentially important diagnostic and therapeutic agents to the brain. Therapeutic molecules and genes that might otherwise be effective in diagnosis and therapy do not cross the BBB in adequate amounts. It is reported that over 95% of all therapeutic molecules do not cross the blood-brain barrier.

Trastuzumab (tradename Herceptin®), an approved monoclonal antibody specific for the human Her2/neu protein, is an important therapeutic option in the treatment of the approximately 30% of human breast cancers that are positive for this protein. While trastuzumab has proven valuable in the treatment and control of systemic disease; it cannot address the frequently observed spread of metastatic Her2/neu-expressing cancer cells in the central nervous system (CNS), due to the fact that trastuzumab cannot cross the blood-brain barrier.

There is an important unmet need for improving the therapeutic potential of antibodies, including those that are specific for Her2/neu or Her1/EGFR. For example, there is a need for anti-Her2/neu or anti-Her1/EGFR antibodies and antigen-binding fragments that have improved activity and/or other properties relative to conventional antibodies. In addition, there is a need for compositions and methods that facilitate the delivery of anti-Her2/neu or anti-Her1/EGFR antibodies across the blood-brain-barrier in order to effectively treat Her2/neu+ or Her1/EGFR+ cancers, particularly those that have metastasized to the CNS. These same needs apply to other cancer antigen-specific antibodies, including antibodies that are specific for Her3, A33 antigen, CD5, CD19, CD20, CD22, CD23 (IgE Receptor), C242 antigen, 5T4, IL-6, IL-13, vascular endothelial growth factor VEGF (e.g., VEGF-A), and others.

The present invention addresses these needs and offers other related advantages.

BRIEF SUMMARY

According to a general aspect, the present invention provides therapeutic compositions comprising a p97 polypeptide sequence and an antibody or an antigen-binding fragment thereof. In some embodiments, the antibody or fragment thereof specifically binds to a cell surface protein, such as a cell surface receptor. In particular embodiments, the antibody specifically binds to a cancer-associated antigen, or cancer antigen. Certain cancer antigens include cell surface proteins and their respective ligands. In specific embodiments, the antibody or fragment thereof specifically binds the human Her2/neu protein or the human Her1/EGF receptor.

In certain aspects, the p97 polypeptide sequence and the antibody or fragment thereof are each bound to or encapsulated within a particle, e.g., a nanoparticle, bead, lipid formulation, lipid particle, or liposome, e.g., immunoliposome. In particular embodiments, the p97 polypeptide sequence is present on the surface of the particle, and the antibody or fragment thereof is present on surface of the particle and/or encapsulated within the particle.

In a related general aspect, the present invention also provides therapeutic conjugates comprising a p97 polypeptide sequence covalently linked to an antibody or antigen-binding fragment thereof. In specific embodiments, the antibody or fragment thereof specifically binds the human Her2/neu protein. As described herein, such compositions and conjugates are of particular value in the treatment of Her2/neu-expressing cancers, including those which have metastasized to the CNS.

The p97 polypeptide sequence used in the conjugates of the invention can be essentially any amino acid sequence derived from a p97 protein. In a specific embodiment, the p97 polypeptide sequence used in a conjugate of the invention comprises the amino acid sequence set forth in SEQ ID NO: 1. In another specific embodiment, the p97 polypeptide sequence is a sequence having at least 80% identity to the sequence of SEQ ID NO: 1. In still another specific embodiment, the p97 polypeptide sequence is a fragment of a human p97 protein sequence having at least about 20, 30, 40, 50, 60, 70, 80, 90 or 100, or more contiguous amino acid residues of the sequence set forth in SEQ ID NO: 1. In another specific embodiment, the p97 polypeptide sequence is a soluble p97 polypeptide sequence. In still another specific embodiment, the p97 polypeptide sequence is a sequence that is effective for facilitating transport of an antibody to which it is linked across the blood-brain barrier.

A p97 polypeptide sequence can be conjugated to any therapeutic antibody or antigen-binding fragment (e.g., anti-Her2/neu antibody or antigen-binding fragment) using any of a variety of known and established methodologies, illustrative examples of which are described herein. These techniques include chemical conjugation techniques. In other embodiments, the techniques rely upon standard recombinant DNA technology (e.g., for producing fusion polypeptides).

In certain more specific embodiments of the invention, the p97 polypeptide sequence is covalently linked to the antibody or antigen-binding fragment with a linker. In a more specific embodiment, the p97 polypeptide sequence is (a) covalently linked to the antibody or antigen-binding fragment with a polymeric cross-linker, (b) covalently linked to the antibody or antigen-binding fragment via a nanoparticle, or (c) operatively linked to the antibody or antigen-binding fragment thereof via a liposome. In another specific embodiment, the p97 polypeptide sequence is covalently linked to the antibody or antigen-binding fragment with a polymeric cross-linker comprising polyethylene glycol. In another specific embodiment, the p97 polypeptide sequence is covalently linked to the antibody or antigen-binding fragment with a polymeric cross-linker comprising thioether linkage(s).

The anti-Her2/neu antibody or antigen-binding fragment thereof used in accordance with the invention will generally be capable of specifically binding to a human Her2/neu protein having a sequence set forth in SEQ ID NO: 2.

In a more specific embodiment, the anti-Her2/neu antibody is trastuzumab or an antigen-binding fragment or derivative thereof.

The p97 antibody conjugate can also be a fusion polypeptide comprising a p97 polypeptide sequence and a Her2/neu specific antibody or antigen binding sequence. The fusion polypeptides may be advantageously co-expressed using routine recombinant DNA methodologies to produce a desired conjugate of the invention.

Accordingly, in another aspect, the present invention provides isolated fusion polynucleotides, and host cells containing the same, wherein the fusion polynucleotides encode fusion polypeptides comprising a p97 polypeptide sequence and therapeutic antibody or antigen-binding fragment thereof, for instance, a Her2/neu specific antibody or antigen binding fragment.

According to still another aspect, the present invention provides pharmaceutical compositions comprising a p97 antibody conjugate or a polynucleotide encoding a p97 conjugate, and a pharmaceutically acceptable excipient.

According to still another aspect, the invention provides a method for the treatment of a subject with a Her2/neu-expressing cancer by administering to the subject a pharmaceutical composition comprising a p97-antibody conjugate of the invention. The Her2/neu-expressing cancer to be treated is, in certain embodiments, a metastatic cancer, particularly a metastatic cancer characterized by CNS progression.

Also included are conjugates, comprising a p97 polypeptide sequence covalently linked to a monoclonal antibody or antigen-binding fragment thereof. In some embodiments, the antibody or antigen-binding fragment thereof specifically binds to a eukaryotic cell-surface protein. In certain embodiments, the antibody or antigen-binding fragment thereof specifically binds to a mammalian cell-surface protein, optionally a human cell-surface protein. In particular embodiments, the antibody or antigen binding fragment thereof specifically binds to a cancer-associated antigen.

In certain embodiments, the cancer-associated antigen is associated with one or more of breast cancer, metastatic brain cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, epithelial tumor, bone cancer, or a hematopoietic cancer.

In some embodiments, the cancer-associated antigen is selected from one or more of Her2/neu, Her1/EGF receptor (EGFR), Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein, alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In certain embodiments, the monoclonal antibody is selected from one or more of trastuzumab, 3F8, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

In specific embodiments, the monoclonal antibody is a humanized or chimeric monoclonal antibody.

Also included are pharmaceutical compositions comprising a p97-antibody conjugate described herein and a pharmaceutically acceptable carrier or excipient. Certain embodiments relate to methods for the treatment of a subject with a cancer, comprising administering to the subject a pharmaceutical composition described herein. In some embodiments, the subject has a cancer selected from one or more of breast cancer, metastatic brain cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, epithelial tumor, bone cancer, or a hematopoietic cancer.

In particular embodiments, the cancer is associated with expression of at least one of Her2/neu, Her1/EGFR, Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein, alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), or mesothelin. In certain embodiments, the monoclonal antibody portion of the p97-antibody conjugate specifically binds to the cancer-associated antigen.

In certain embodiments, the cancer is a metastatic colorectal cancer or a head and neck cancer, and the monoclonal antibody specifically binds to Her1/EGFR and is an EGFR antagonist. In particular embodiments, the monoclonal antibody specifically binds to (e.g., one or more continuous or discontinuous epitopes of) SEQ ID NO:15 (Her1/EGFR). In certain embodiments, the cancer is an EGFR-expressing metastatic colorectal cancer. In specific embodiments, the colorectal cancer is KRAS wild-type. In certain embodiments, the conjugate is administered after failure of both irinotecan- and oxiplatin-based regimens. In some embodiments, the subject is intolerant to irinotecan-based regimens or is refractory to irinotecan-based chemotherapy. In other aspects, the cancer is a locally or regionally advanced squamous cell carcinoma of the head and neck, a recurrent locoregional disease or metastatic squamous cell carcinoma of the head and neck, or a recurrent or metastatic squamous cell carcinoma of the head and neck progressing after platinum-based therapy. In some embodiments, the conjugate is administered in combination with radiation therapy, platinum-based therapy, or platinum-based therapy with 5-FU. In certain of these and related embodiments, the antibody is cetuximab, or an antigen-binding fragment thereof.

Certain conjugates comprise a p97 polypeptide covalently linked to an antibody (Ab) according to one of the structures:

p97(FGly)-R$_1$-Ab or p97-R$_1$-(FGly)Ab where R$_1$ is at least one aldehyde reactive linkage; and FGly is a formylglycine residue within a heterologous sulfatase motif that comprises the structure:

X$_1$(FGly)X$_2$Z$_2$X$_3$ (SEQ ID NO:5)

where Z$_2$ is a proline or alanine residue; X$_1$ is present or absent and, when present, is any amino acid, where X$_1$ is optionally present when the heterologous sulfatase motif is at the N-terminus of the p97 polypeptide; and X$_2$ and X$_3$ are each independently any amino acid.

In some embodiments, R$_1$ comprises a Schiff base. In particular embodiments, R$_1$ is an oxime linkage, a hydrazine linkage, or a hydrazine carbothiamide linkage.

Also included are isolated p97 polypeptides, comprising at least one heterologous sulfatase motif that comprises the following structure:

X$_1$Z$_1$X$_2$Z$_2$X$_3$ (SEQ ID NO:6)

where Z$_1$ is cysteine or serine; Z$_2$ is a proline or alanine residue; X$_1$ is present or absent and, when present, is any amino acid, where X$_1$ is optionally present when the heterologous sulfatase motif is at the N-terminus of the aldehyde tagged polypeptide; and X$_2$ and X$_3$ are each independently any amino acid.

Certain isolated p97 polypeptides comprise at least one heterologous sulfatase motif that comprises the structure:

X$_1$(FGly)X$_2$Z$_2$X$_3$ (SEQ ID NO:5)

where FGly is a formylglycine residue; Z$_2$ is a proline or alanine residue; X$_1$ is present or absent and, when present, is any amino acid, where X$_1$ is optionally present when the heterologous sulfatase motif is at the N-terminus of the p97 polypeptide; and X$_2$ and X$_3$ are each independently any amino acid.

In some embodiments, the isolated p97 polypeptide is covalently linked to an antibody (Ab) that comprises at least one heterologous sulfatase motif, where the motif comprises the structure:

X$_1$(FGly)X$_2$Z$_2$X$_3$ (SEQ ID NO:5)

where FGly is a formylglycine residue; Z$_2$ is a proline or alanine residue; X$_1$ is present or absent and, when present, is any amino acid, where X$_1$ is optionally present when the heterologous sulfatase motif is at the N-terminus of the antibody; and X$_2$ and X$_3$ are each independently any amino acid, where the p97 polypeptide and the antibody are covalently linked via their respective FGly residues to form a p97-antibody conjugate. In some embodiments, the isolated p97-antibody conjugate comprises the following structure:

p97(FGly)-R$_1$-L-R$_2$-(FGly)Ab where R$_1$ and R$_2$ are the same or different aldehyde reactive linkage; and L is a linker moiety.

In some embodiments, the at least one heterologous sulfatase motif is at the C-terminus of the p97 polypeptide and the N-terminus of the antibody. In certain embodiments, the at least one heterologous sulfatase motif is at the N-terminus of the p97 polypeptide and the C-terminus of the antibody. In particular embodiments, the at least one heterologous sulfatase motif is at the N-terminus of the p97 polypeptide and the N-terminus of the antibody. In some embodiments, the at least one heterologous sulfatase motif is at the C-terminus of the p97 polypeptide and the C-terminus of the antibody. In specific embodiments, R$_1$ and R$_2$ independently comprise a Schiff base. In certain instances, R$_1$ and R$_2$ are independently an oxime linkage, a hydrazide linkage, or a hydrazine carbothiamide linkage. In some instances, L is a peptide, a water-soluble polymer, a detectable label, or a glycan.

Also included are methods of producing a p97 polypeptide, comprising a) culturing a host cell that expresses an introduced polynucleotide, where the introduced polynucleotide encodes the p97 polypeptide of claim 20, and where the host cell expresses a formylglycine generating enzyme (FGE) which converts Z$_1$ into a formylglycine (FGly) residue; and b) isolating the 97 polypeptide from the cell. In some embodiments, the p97 polypeptide comprises (i) at least one unnatural amino acid with an azide side-chain, or (ii) at least one unnatural amino acid with an alkyne side-chain.

Certain embodiments relate to conjugate, comprising the structure (I) or (II):

-continued

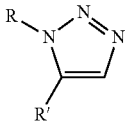

(II)

where R is a p97 polypeptide and R' is an antibody or antigen-binding fragment thereof; or where R is an antibody or antigen-binding fragment thereof and R' is a p97 polypeptide. In some embodiments, the antibody specifically binds the human Her2/neu protein, or other cell surface protein or cancer associated antigen described herein. Particular examples include Her1/EGF receptor (EGFR), Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein, alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In specific embodiments, the antibody is trastuzumab, 3F8, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, NEURADIAB® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, tucotuzumab (celmoleukin), ublituximab, urelumab, veltuzumab, volociximab, votumumab, or zalutumumab, or an antigen-binding fragment thereof.

Also included are methods of producing a p97-antibody conjugate, comprising: (a) performing an azide-alkyne cycloaddition reaction between: (i) a p97 polypeptide that comprises at least one unnatural amino acid with an azide side-chain and an antibody or antigen-binding fragment thereof that comprises at least one unnatural amino acid with an alkyne side-chain; or (ii) a p97 polypeptide that comprises at least one unnatural amino acid with an alkyne side-chain and an antibody or antigen-binding fragment thereof that comprises at least one unnatural amino acid with an azide side-chain; and (b) isolating a p97-antibody conjugate from the reaction, thereby producing a p97-antibody conjugate.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A-1D show the results of cell viability assays for the human breast cancer cell line BT474.

FIGS. 2A-2D show the results of cell viability assays for the human breast cancer cell line MCF7-HER2.

FIGS. 3A-3D show the results of cell viability assays for the human breast cancer cell line MCF7-vector.

FIGS. 4A-4D show the results of cell viability assays for the human breast cancer cell line SKBR3.

FIG. 6A shows brain metastases of heterogenous size within the regions outlined in red, and FIG. 6B shows Texas Red-Dextran staining of the metastases. FIG. 6C shows an autoradiogram of $^{125}$I-labeled trastuzumab, and indicates the fold increase in antibody relative to the surrounding normal brain tissue. As shown in FIG. 6F, the $K_{in}$ values for trastuzumab alone are about $1.46 \times 10^{-7}$ mL/sec/g in normal brain tissue and about $3.8 \times 10^{-7}$ mL/sec/g in brain metastases.

FIGS. 7A-7E show the distribution of $^{125}$I-labeled trastuzumab in the mouse brain and other tissues at 24 hours post-intravenous administration. FIG. 7A shows brain metastases of heterogenous size within the regions outlined in red, and FIG. 7B shows Texas Red-Dextran staining of the metastases. FIG. 7C shows the autoradiogram of $^{125}$I-labeled trastuzumab, and indicates the fold increase in antibody relative to the surrounding normal brain tissue. FIG. 7D shows the tissue to blood ratio of $^{125}$I-labeled trastuzumab in various tissues, and FIG. 7E shows the distribution in normal brain tissue and brain metastases (Mets).

FIG. 8A shows brain metastases of heterogenous size within the regions outlined in red, and FIG. 8B shows Texas Red-Dextran staining of the metastases. FIG. 8C shows an autoradiogram of $^{125}$I-labeled p97-trastuzumab conjugates, and the left of FIG. 8C indicates the amount (ng/g) of conjugate found in each metastases. The left of FIG. 8B shows the fold increase of p97-trastuzumab conjugate found in each metastases, relative to the brain distant to tumor (BDT) region shown in FIG. 8A. FIG. 8D shows the tissue/blood ratio of p97-trastuzumab conjugate for a variety of tissues. Figure BE shows the ratio of p97-trastuzumab conjugate in normal brain/blood and brain metastases/blood. FIG. 8F summarizes the concentration of $^{125}$I-labeled p97-trastuzumab conjugate found in individual brain metastases.

FIGS. 9A-9F show the distribution of $^{125}$I-labeled p97-trastuzumab in the mouse brain and other tissues at eight hours post-intravenous administration. FIG. 9A shows brain metastases of heterogenous size within the regions outlined in red, and FIG. 9B shows Texas Red-Dextran staining of the metastases. FIG. 9C shows an autoradiogram of $^{125}$I-labeled p97-trastuzumab conjugate, and the left of FIG. 9C indicates the amount (ng/g) of conjugate found in each metastases. The left of FIG. 9B shows the fold increase of p97-trastuzumab conjugate found in each metastases, relative to the brain distant to tumor (BDT) regions shown in FIG. 9A. FIG. 9D shows the tissue/blood ratio of p97-trastuzumab conjugate for a variety of tissues. FIG. 9E shows the ratio of p97-trastuzumab conjugate in normal brain/blood and brain metastases/blood. FIG. 9F summarizes the concentration of $^{125}$I-labeled p97-trastuzumab conjugate found in individual brain metastases.

FIG. 10A shows the tissue/blood ratio of p97-trastuzumab conjugate for a variety of tissues. FIG. 10B shows that the levels of conjugate in normal brain tissue are marginally higher at the eight hour time point (relative to the two hour time point), and the levels of conjugate in brain metastases are significantly higher at the that same time point. FIG. 10C shows the measured $K_{in}$ values for the p97-trastuzumab conjugate in normal brain tissue ($1.1 \times 10^{-4}$ mL/sec/g) and brain metastases ($4.9 \times 10^{-4}$ mL/sec/g). FIG. 10D shows the percentage of injected dose in brain tissue at 2 and 8 hours, and FIG. 10E summarizes the concentration of $^{125}$I-labeled p97-trastuzumab conjugate in individual brain metastases at two and eight hours post-administration.

FIG. 11A shows the HPLC profile of the crude reaction mixture after 24 hours at room temperature, and FIG. 11B shows the size-exclusion HPLC profile of purified 1:1 p97-cetuximab conjugate (>96% purity, HPLC detection at 220 nm).

BRIEF DESCRIPTION OF THE SEQUENCES

Figure 5A:
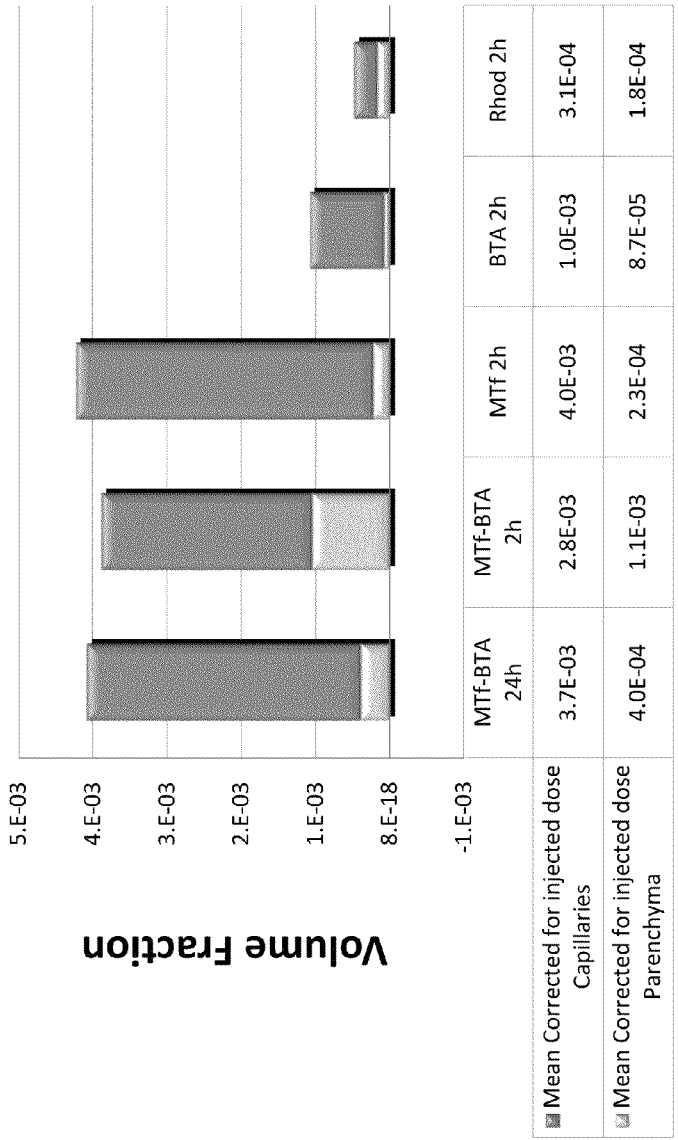
FIGS. 5A-5D show the biodistribution of rhodamine (rhod)-labeled proteins in the brain tissue of mice. In these figures, "MTF" is p97, "BTA" is trastuzumab, and "MTF-BTA" is a p97-trastuzumab conjugate.

SEQ ID NO:1 is the amino acid sequence of the human p97 melanotransferrin protein (NP_005920.2).

SEQ ID NO:2 is the amino acid sequence of the human Her2/neu protein (NP_004439.2).

SEQ ID NO:3 is a nucleic acid sequence encoding the polypeptide sequence of SEQ ID NO: 1.

SEQ ID NO:4 is a nucleic acid sequence of the encoding the polypeptide sequence of SEQ ID NO: 2.

SEQ ID NOS:5 and 6 are peptide sulfatase motifs.

SEQ ID NOS:8-14 are peptide linkers.

SEQ ID NO:15 is the amino acid sequence of the human Her1/epidermal growth factor receptor (EGFR).

DETAILED DESCRIPTION

The present invention relates generally to conjugate molecules comprising p97 polypeptide sequences linked to antibodies or antigen-binding fragments thereof. Also included are compositions that comprise a p97 polypeptide sequence and an antibody or antigen-binding fragment thereof, such as particle-based compositions, e.g., liposomes. The p97 polypeptide sequences of the invention can be conjugated to or composed with any antibody or antigen-binding fragment thereof, including therapeutic and diagnostic antibodies. Certain therapeutic and/or diagnostic antibodies or antigen-binding fragments thereof specifically bind to a cell surface protein, such as a cell surface receptor.

In particular embodiments, the antibodies or fragments specifically bind to the human Her2/neu protein. As demonstrated herein, trastuzumab (trade name Herceptin®), a humanized monoclonal antibody used clinically in the treatment of HER2+ breast cancer, was chemically linked to p97 polypeptide sequences to generate p97-antibody conjugates. Unexpectedly, the p97-antibody conjugates demonstrated a significant improvement in cancer killing activity compared to trastuzumab alone. Furthermore, the results confirmed, as expected, that trastuzumab does not enter human brain endothelial (HBE) cells in culture. However, in the case of p97-antibody conjugates, there was a marked transport of the conjugates into HBE cells, indicating that the conjugates have the potential to enter brain tissue. The combination of p97 and trastuzumab as a protein conjugate also synergistically increased delivery across the blood brain barrier to parenchymal brain tissue, relative to delivery of p97 alone and trastuzumab alone. Based on these unexpected findings, the present invention provides compositions and methods for the improved treatment of Her-2/neu-expressing cancers, including those associated with metastasis to the CNS. The present invention further provides p97-antibody conjugates, compositions, and related methods for the improved treatment of other types of cancer, particularly those that associate with at least one antigen that can be targeted by antibody therapy.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology or Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise," or variations such as "comprises" or "comprising," will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

The functional properties of the p97-antibody conjugates described herein may be assessed using a variety of methods known to the skilled person, including, e.g., affinity/binding assays (for example, surface plasmon resonance, competitive inhibition assays); cytotoxicity assays, cell viability assays, cell proliferation or differentiation assays, cancer cell and/or tumor growth inhibition using in vitro or in vivo models. Other assays may test the ability of conjugates described herein to block normal Her2/neu-mediated responses. The conjugates described herein may also be tested for effects on receptor internalisation, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

p97 Polypeptide Sequences

As noted above, exemplary conjugate molecules and compositions of the present invention include a p97 polypeptide sequence. The term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

In certain specific embodiments, a p97 polypeptide sequence used in a conjugate of the invention comprises the human p97 sequence set forth in SEQ ID NO: 1.

In other specific embodiments, a p97 polypeptide sequence used in a conjugate of the invention comprises a sequence having at least 70%, 75%, 80%, 85%, 90%, 95%, 96%, 97%, 98%, or 99% identity, along its length, to a human p97 sequence set forth in SEQ ID NO: 1.

In still other specific embodiments, a p97 polypeptide sequence used in a conjugate of the invention comprises a fragment of a human p97 sequence set forth in SEQ ID NO: 1, e.g., wherein the fragment comprises at least about 10, 20, 30, 40, 50, 60, 70, 80, 90 or 100, or more, contiguous amino acids, including all intermediate lengths, of a human p97 sequence set forth in SEQ ID NO: 1.

In other specific embodiments, a p97 polypeptide sequence used in a conjugate of the invention comprises a fragment of a human p97 sequence set forth in SEQ ID NO: 1, wherein the fragment consists of no more than about 10, 20, 30, 40, 50, 60, 70, 80, 90 or 100, or more, contiguous amino acids, including all intermediate lengths, of a human p97 sequence set forth in SEQ ID NO: 1.

In still other specific embodiments, a p97 polypeptide sequence used in a conjugate of the invention comprises a fragment of a human p97 sequence set forth in SEQ ID NO: 1, wherein the fragment includes about 20-500, 20-400, 20-300, 20-200, 20-100, or 20-50, contiguous amino acids of a human p97 sequence set forth in SEQ ID NO: 1.

In certain other embodiments, p97 polypeptide sequences of interest are amino acid subsequences and variants of p97 that are effective for transporting an anti-Her2/neu antibody across the blood brain barrier.

In other specific embodiments, a p97 polypeptide sequence used in a conjugate is a soluble form of a p97 polypeptide (e.g., Yang et al., *Prot Exp Purif.* 34:28-48, 2004), or a fragment or variant thereof. In some aspects, the p97 polypeptide has a deletion of the all or a portion of the hydrophobic domain (residues 710-738 of SEQ ID NO:1), alone or in combination with a deletion of all or a portion of the signal peptide (residues 1-19 of SEQ ID NO:1). In specific aspects, the p97 polypeptide comprises or consists of residues 20-711 of SEQ ID NO:1, including variants and fragments thereof.

In certain other embodiments, the p97 fragment or variant used in a conjugate of the invention is a fragment or variant capable of binding a p97 receptor, a LRP1 receptor and/or a LRP1B receptor.

It will be understood that a conjugate may also comprise additional amino acids unrelated to the p97 and anti-Her2/neu antibody sequences present.

The p97 polypeptide sequence may also be a variant p97 polypeptide sequence. A p97 polypeptide "variant," as the term is used herein, is a polypeptide that typically differs from a p97 polypeptide specifically disclosed herein in one or more substitutions, deletions, additions and/or insertions. Such variants may be naturally occurring or may be synthetically generated, for example, by modifying one or more of the above polypeptide sequences of the invention and evaluating their activity as described herein and/or using any of a number of techniques well known in the art.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides of the invention may be prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-46 (1963). Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

When comparing polypeptide or polynucleotide sequences, two sequences are said to be "identical" if the nucleotide or amino acid sequence in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., *A model of evolutionary change in proteins—Matrices for detecting distant relationships* (1978). In *Atlas of Protein Sequence and Structure*, vol. 5, supp. 3, pp. 345-58 (Dayhoff, M. O., ed.); Hein J., *Methods in Enzymology* 183:626-45 (1990); Higgins et al., *CABIOS* 5:151-53 (1989); Myers et al., *CABIOS* 4:11-17 (1988); Robinson, E. D., *Comb. Theor* 11:105 (1971); Saitou et al., *Mol. Biol. Evol.* 4:406-25 (1987); Sneath at al., *Numerical Taxonomy—the Principles and Practice of Numerical Taxonomy* (1973); Wilbur et al., *Proc. Natl. Acad. Sci. USA* 80:726-30 (1983).

Alternatively, optimal alignment of sequences for comparison may be conducted by the local identity algorithm of Smith et al., *Add. APL. Math* 2:482 (1981), by the identity alignment algorithm of Needleman et al., *J. Mol. Biol.* 48:443 (1970), by the search for similarity methods of Pearson et al., *Proc. Natl. Acad. Sci. USA* 85:2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-10 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide or polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid or nucleic acid residue occurs in both sequences to yield the number of matched positions, dividing the number of matched positions by the total number of positions in the reference sequence (i.e., the window size) and multiplying the results by 100 to yield the percentage of sequence identity.

Antibodies

The antibody or antigen-binding fragment used in the conjugates or compositions of the present invention can be of essentially any type. Particular examples include therapeutic and diagnostic antibodies. As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies," multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, for instance, the human Her2/neu protein. In this regard, an antigen-binding fragment of the herein described antibodies may comprise 1, 2, 3, 4, 5, or all 6 CDRs of a VH and VL sequence from antibodies that bind to a therapeutic or diagnostic target, such as human Her2/neu.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (III et al., *Prot. Eng.* 10: 949-57 (1997); minibodies (Martin et al., *EMBO J* 13: 5305-9 (1994); diabodies (Holliger et al., *PNAS* 90: 6444-8 (1993); or Janusins (Traunecker et al., *EMBO J* 10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward, E. S. et al., Nature 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts e.g. *E. coli* (see e.g. U.S. Pat. No. 6,765,087), moulds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of nanobodies have been produced. Nanobodies may be formulated as a ready-to-use solution having a long shelf life. The Nanoclone method (see, e.g., WO 06/079372) is a proprietary method for generating Nanobodies against a desired target, based on automated high-throughput selection of B-cells.

In certain embodiments, the antibodies or antigen-binding fragments thereof are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332: 323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present invention may be chimeric antibodies. In this regard, a chimeric antibody is comprised of an antigen-binding fragment of an antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

An epitope that "specifically binds" or "preferentially binds" (used interchangeably herein) to an antibody or a polypeptide is a term well understood in the art, and methods to determine such specific or preferential binding are also well known in the art.

A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

In certain embodiments, the antibody or antigen-binding fragment thereof specifically binds to a cancer-associated antigen, or cancer antigen. Exemplary cancer antigens include cell surface proteins such as cell surface receptors. Also included as cancer-associated antigens are ligands that bind to such cell surface proteins or receptors. In specific embodiments, the antibody or antigen-binding fragment specifically binds to a intracellular cancer antigen.

In some embodiments, the cancer that associates with the cancer antigen is one or more of breast cancer, metastatic brain cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, epithelial tumor, bone cancer, or a hematopoietic cancer.

In particular embodiments, the antibody or antigen-binding fragment specifically binds to at least one cancer antigen selected from human Her2/neu, Her1/EGF receptor, Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In particular embodiments, the antibody or antigen-binding fragment thereof specifically binds to the human Her2/neu protein. Essentially any anti-Her2/neu antibody, antigen-binding fragment or other Her2/neu-specific binding agent may be used in producing the p97-antibody conjugates of the present invention. Illustrative anti-Her2/neu antibodies are described, for example, in U.S. Pat. Nos. 5,677,171; 5,720,937; 5,720,954; 5,725,856; 5,770,195; 5,772,997; 6,165,464; 6,387,371; and 6,399,063, the contents of which are incorporated by reference in their entireties.

In some embodiments, the antibody or antigen-binding fragment thereof specifically binds to the human Her1/EGFR (epidermal growth factor receptor). Essentially any anti-Her1/EGFR antibody, antigen-binding fragment or other Her1-EGFR-specific binding agent may be used in producing the p97-antibody conjugates of the present invention. Illustrative anti-Her1/EGFR antibodies are described, for example, in U.S. Pat. Nos. 5,844,093; 7,132,511; 7,247,301; 7,595,378; 7,723,484; 7,939,072; and 7,960,516, the contents of which are incorporated by reference in their entireties.

In certain embodiments, the antibody is an anti-cancer therapeutic antibody, including exemplary antibodies such as 3F8, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, trastuzumab, tucotuzumab (celmoleukin), ublituximab, urelumab, veltuzumab, volociximab, votumumab, and zalutumumab. Also included are fragments, variants, and derivatives of these antibodies In specific embodiments, the anti-Her2/neu antibody used in a conjugate of the invention is trastuzumab (Hercepti®), or a fragment or derivative thereof. Trastuzumab is a Her2/neu-specific monoclonal antibody approved for the treatment of human breast cancer. As demonstrated herein, conjugation of p97 amino acid sequences to the trastuzumab antibody unexpectedly resulted in greater levels of cancer cell killing than with the trastuzumab antibody alone. Furthermore, there was a marked transport of the p97-antibody conjugates into HBE cells, suggesting that the conjugates will be effective for delivery across the blood-brain barrier. Further data strongly suggest that therapeutically effective concentrations of p97-trastuzumab conjugate can be achieved in brain tissue metastases, even by systemic (e.g., intravenous) administration of such conjugates. These data also suggest that p97 and trastuzumab work synergistically together to selectively target p97-trastuzumab conjugates to brain metastases relative to normal brain tissue, and at a significantly greater rate (~1000 fold) than trastuzumab alone. Conjugation to p97 thus not only increases transport of trastuzumab across the blood-brain barrier, but also the blood-tumor barrier. Further, because of the reduced distribution to heart tissues relative to other tissues, these data suggest that conjugation to p97 might reduce the cardiotoxic effects of antibodies such as trastuzumab. Accordingly, the p97-antibody conjugates of the invention, in certain embodiments, will give rise to particular advantages in the treatment of Her2/neu-expressing cancers, including but not limited to those that have metastasized to the CNS.

In some embodiments, an anti-Her2/neu binding fragment comprises one or more of the CDRs of a Her2/neu antibody. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc*. (1994) 116: 2161-2162.

In specific embodiments, the anti-Her1/EGFR antibody used in a conjugate of the invention is cetuximab (Erbitux®), or a fragment or derivative thereof. In certain embodiments, an anti-Her1/EGFR binding fragment comprises one or more of the CDRs of a Her1/EGFR antibody such as cetuximab. Cetuximab is approved for the treatment of head and neck cancer, and colorectal cancer. Cetuximab is composed of the Fv (variable; antigen-binding) regions of the 225 murine EGFR monoclonal antibody specific for the N-terminal portion of human EGFR with human IgG1 heavy and kappa light chain constant (framework) regions.

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto. Also included are methods that utilize transgenic animals such as mice to express human antibodies. See, e.g., Neuberger et al., *Nature Biotechnology* 14:826, 1996; Lonberg et al., *Handbook of Experimental Pharmacology* 113:49-101, 1994; and Lonberg et al., *Internal Review of Immunology* 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., *Nature Protocols*. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art. The p97 polypeptides described herein and known in the art may be used in the purification process in, for example, an affinity chromatography step.

These just-described techniques are, in and of themselves, known as such in the art. The skilled person will, however, be able to use such techniques to obtain antibodies or antigen-binding fragments thereof and to covalently couple them with p97 polypeptide sequences according to several embodiments of the invention described herein.

p97-Antibody Conjugates

Conjugation of a p97 polypeptide sequence and an antibody or binding fragment thereof can be carried out using standard chemical, biochemical and/or molecular techniques. Indeed, it will be apparent how to make a p97-antibody conjugate in light of the present disclosure using available art-recognized methodologies. Of course, it will generally be preferred when linking the primary components of a conjugate of the present invention that the conjugation techniques employed and the resulting linking chemistries do not substantially disturb the desired functionality or activity of the individual components of the conjugate.

In certain embodiments, conjugates of the invention may employ any suitable linking groups or types known in the art for joining a heterologous polypeptide sequence to an antibody or antigen-binding sequence. Preferably, the antigen (e.g., human Her-2/neu protein, human Her1/EGFR) binding ability and/or activity of conjugate is not substantially reduced as a result of the conjugation technique employed, for example, as compared to the unconjugated antibody, such as the unconjugated anti-Her2/neu antibody.

In certain embodiments, a p97 polypeptide sequence may be coupled (e.g., covalently linked) to a suitable antibody or binding fragment thereof (e.g., anti-Her2/neu monoclonal antibody) either directly or indirectly (e.g., via a linker group). A direct reaction between a p97 polypeptide sequence and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a p97 polypeptide sequence and an antibody or binding fragment thereof (e.g., anti-Her2/neu antibody or binding fragment thereof) via a linker group. A linker group can also function as a spacer to distance an antibody from the p97 polypeptide sequence in order to avoid interference with binding capabilities, targeting capabilities or other functionalities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

In some embodiments, it may be desirable to couple more than one p97 polypeptide sequence to an antibody (e.g., anti-Her2/neu antibody), or vice versa. For example, in certain embodiments, multiple p97 polypeptide sequences are coupled to one antibody molecule or binding fragment thereof. In one embodiment, multiple p97 polypeptide sequences are coupled to one anti-Her2/neu antibody molecule or binding fragment thereof. The p97 polypeptide sequences can be the same or different. Regardless of the particular embodiment, conjugates containing multiple p97 polypeptide sequences may be prepared in a variety of ways. For example, more than one polypeptide may be coupled directly to an antibody molecule, or linkers that provide multiple sites for attachment can be used. Any of a variety of known heterobifunctional crosslinking strategies can be employed for making conjugates of the invention. It will be understood that many of these embodiments can be achieved by controlling the stoichiometries of the materials used during the conjugation/crosslinking procedure.

In a more specific embodiment of the invention, an amine-to-sulfhydryl crosslinker is used for preparing a conjugate. In one preferred embodiment, for example, the crosslinker is succinimidyl-4-(N-maleimidomethyl)cyclohexane-1-carboxylate (SMCC) (Thermo Scientific), which is a sulfhydryl crosslinker containing NHS-ester and maleimide reactive groups at opposite ends of a medium-length cyclohexane-stabilized spacer arm (8.3 angstroms). SMCC is a non-cleavable and membrane permeable crosslinker that can be used to create sulfhydryl-reactive, maleimide-activated anti-Her2/neu antibodies or antigen-binding fragments for subsequent reaction with p97 polypeptide sequences. NHS esters react with primary amines at pH 7-9 to form stable amide bonds. Maleimides react with sulfhydryl groups at pH 6.5-7.5 to form stable thioether bonds. Thus, the amine reactive NHS ester of SMCC crosslinks rapidly with primary amines of an anti-Her2/neu antibody and the resulting sulfhydryl-reactive maleimide group is then available to react with cysteine residues of p97 to yield specific conjugates of interest.

In certain specific embodiments, the p97 polypeptide sequence is modified to contain exposed sulfhydryl groups to facilitate crosslinking, e.g., to facilitate crosslinking to a maleimide-activated antibody, such as an anti-Her2/neu antibody. In a more specific embodiment, the p97 polypeptide sequence is modified with a reagent which modifies primary amines to add protected thiol sulfhydryl groups. In an even more specific embodiment, the reagent N-succinimidyl-S-acetylthioacetate (SATA) (Thermo Scientific) is used to produce thiolated p97 polypeptides.

In other specific embodiments, a maleimide-activated antibody is reacted under suitable conditions with thiolated p97 polypeptides to produce a conjugate of the present invention. It will be understood that by manipulating the ratios of SMCC, SATA, antibody (e.g., anti-Her2/neu antibody) and p97 polypeptide in these reactions it is possible to produce conjugates having differing stoichiometries, molecular weights and properties.

The specific crosslinking strategy discussed above (and exemplified below) is but one of many examples of suitable conjugation strategies that may be employed in producing conjugates of the invention. It will be evident to those skilled in the art that a variety of other bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

In other illustrative embodiments, the conjugates include linking groups such as those disclosed in U.S. Pat. No. 5,208,020 or EP Patent 0 425 235 B1, and Chari et al., Cancer Research 52: 127-131 (1992). Illustrative linking groups include, for example, disufide groups, thioether groups, acid labile groups, photolabile groups, peptidase labile groups and esterase labile groups.

In still other illustrative embodiments, conjugates are made using bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

In other embodiments, non-proteinaceous polymers are used in a linker for coupling a p97 polypeptide sequence to an antibody, such as a Her2/neu antibody. These may include, for example, polyethylene glycol, polypropylene glycol, polyoxyalkylenes, or copolymers of polyethylene glycol, polypropylene glycol, and the like.

Where one component of a conjugate may be more potent when free from the conjugate, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

Certain embodiments may employ one or more aldehyde tags to facilitate conjugation between a p97 polypeptide and an antibody or antigen-binding fragment thereof (see U.S. Pat. Nos. 8,097,701 and 7,985,783, incorporated by reference). Here, enzymatic modification at a sulfatase motif of the aldehyde tag through action of a formylglycine generating enzyme (FGE) generates a formylglycine (FGly) residue. The aldehyde moiety of the FGly residue can then be exploited as a chemical handle for site-specific attachment of a moiety of interest to the polypeptide. In some aspects, the moiety of interest is another polypeptide, such as an antibody.

Particular embodiments thus include a p97 polypeptide or antibody or antigen-binding fragment (e.g., anti-Her2/neu antibody) that comprises 1, 2, 3, 4, 5, 6, 7, 8, 9, 10 or more heterologous sulfatase motifs, where the motif comprises the following structure:

$X_1Z_1X_2Z_2X_3$ (SEQ ID NO:6)

where $Z_1$ is cysteine or serine; $Z_2$ is a proline or alanine residue; $X_1$ is present or absent and, when present, is any amino acid, where $X_1$ is preferably present when the heterologous sulfatase motif is at an N-terminus of the aldehyde tagged polypeptide; and $X_2$ and $X_3$ are each independently any amino acid.

Polypeptides with the above-described motif can be modified by an FGE enzyme to generate a motif having a FGly residue, which, as noted above, can then be used for site-specific attachment of a second polypeptide, for instance, via a linker moiety. Such modifications can be performed, for example, by expressing the sulfatase motif-containing polypeptide (e.g., p97, antibody) in a mammalian, yeast, or bacterial cell that expresses an FGE enzyme or by in vitro modification of isolated polypeptide with an isolated FGE enzyme (see Wu et al., *PNAS.* 106:3000-3005, 2009; Rush and Bertozzi, *J. Am Chem Soc.* 130:12240-1, 2008; and Carlson et al., *J Biol Chem.* 283:20117-25, 2008).

Hence, some embodiments include a p97 polypeptide or antibody (or antigen-binding fragment) that comprises 1, 2, 3, 4, 5, 6, 7, 8, 9, 10 or more heterologous sulfatase motifs having a formylglycine residue, where the motif comprises the following structure:

$X_1(FGly)X_2Z_2X_3$ (SEQ ID NO:5)

where FGly is a formylglycine residue; $Z_2$ is a proline or alanine residue; $X_1$ is present or absent and, when present, is any amino acid, where $X_1$ is preferably present when the heterologous sulfatase motif is at an N-terminus of the aldehyde tagged polypeptide; and $X_2$ and $X_3$ are each independently any amino acid.

In particular embodiments, $X_1$, $X_2$, and $X_3$ are each independently an aliphatic amino acid, a sulfur-containing amino acid or a polar, uncharged amino acid. For instance, $X_1$ can be L, M, V, S or T; and $X_2$, and/or $X_3$ can be independently S, T, A, V, G or C.

In some embodiments, the heterologous sulfatase motif(s) can be (a) less than 16 amino acid residues in length, including about 4, 5, 6, 7, 8, 9, 10, 11, 12, 13, 14, or 15 residues in length, (b) positioned at the N-terminus of the polypeptide, (c) positioned at the C-terminus of the polypeptide, (d) positioned at an internal site of an amino acid sequence native to the polypeptide, (e) positioned in a terminal loop of the polypeptide, (f) positioned at a site of post-translational modification of the polypeptide (e.g., glycosylation site), or any combination thereof. In specific embodiments, the antibody that comprises one or more heterologous sulfatase motif(s) specifically binds to human Her2/neu (e.g., Trastuzumab).

Some embodiments relate to conjugates of (i) a sulfatase motif (or aldehyde tag)-containing p97 polypeptide, and (ii) an antibody or antigen-binding fragment thereof that is functionalized with an aldehyde reactive group, or vice versa, where (i) and (ii) are covalently linked via the FGly residue of the sulfatase motif and the aldehyde reactive group. Such conjugates can have one of the following general structures:

p97(FGly)-$R_1$-Ab or p97-$R_1$-(FGly)Ab where $R_1$ is at least one aldehyde reactive linkage; and FGly is a formylglycine residue within a heterologous sulfatase.

The non-aldehyde tag-containing protein (e.g., antibody, p97 polypeptide) can be functionalized with one or more aldehyde reactive groups such as aminooxy, hydrazide, and thiosemicarbazide, and then covalently linked to the aldehyde tag-containing polypeptide via the at least one FGly residue, to form an aldehyde reactive linkage. The attachment of an aminooxy functionalized protein creates an oxime linkage between the FGly residue and the functionalized protein; attachment of a hydrazide-functionalized protein creates a hydrazine linkage between the FGly residue and the functionalized protein; and attachment of a thiosemicarbazide-functionalized protein creates a hydrazine carbothiamide linkage between the FGly residue and the functionalized protein.

Certain embodiments include conjugates of (i) a sulfatase motif (or aldehyde tag)-containing p97 polypeptide and (ii) a sulfatase motif (or aldehyde tag)-containing antibody, where (i) and (ii) are covalently linked via their respective FGly residues, optionally by a bi-functionalized linker moiety. For instance, Certain p97-antibody conjugates may comprise the following structure:

p97(FGly)-$R_1$-L-$R_2$-(FGly)Ab where $R_1$ and $R_2$ are the same or different aldehyde reactive linkage; L is a linker moiety, p97(FGly) is a aldehyde-tag containing p97 polypeptide, and (FGly)Ab is an aldehyde tag-containing antibody, such as an antibody that specifically binds to human Her2/neu (e.g., Trastuzumab). Merely by way of illustration, in some embodiments, the at least one heterologous sulfatase motif can be at the C-terminus of the p97 polypeptide and the N-terminus of the antibody. In other embodiments, the at least one heterologous sulfatase motif can be at the N-terminus of the p97 polypeptide and the C-terminus of the antibody. In still other embodiments, the at least one heterologous sulfatase motif can be at the N-terminus of the p97 polypeptide and the N-terminus of the antibody. In further embodiments, the at least one heterologous sulfatase motif can be at the C-terminus of the p97 polypeptide an the C-terminus of the antibody. As noted above, the at least one heterologous motif can be at an internal position in the p97 polypeptide and/or the antibody. Persons skilled in the art will recognize that other combinations are possible.

The aldehyde reactive linkages of $R_1$ and $R_2$ can be independently formed by any aldehyde reactive group that will form a covalent bond between (i) the formylglycine (FGly) residue of the aldehyde tag and (ii) a linker moiety that is functionalized with said aldehyde reactive group (e.g., a bi-functionalized linker with two aldehyde reactive groups, which can be the same or different). Examples of aldehyde reactive groups include aminooxy, hydrazide, and thiosemicarbazide groups, which will form Schiff-base containing linkages with a FGly residue, including oxime linkages, hydrazine linkages, and hydrazine carbothiamide linkages, respectively. Hence, $R_1$ and $R_2$ can be independently a linkage that comprises a Schiff base, such as an oxime linkage, a hydrazine linkage, or a hydrazine carbothiamide linkage.

In some embodiments, the aldehyde tag-containing p97 polypeptide and the aldehyde tag-containing antibody are linked (e.g., covalently linked) via a multi-functionalized linker (e.g., bi-functionalized linker), the latter being functionalized with the same or different aldehyde reactive group(s). In these and related embodiments, the aldehyde reactive groups allow the linker to form a covalent bridge between the p97 polypeptide and the antibody via their respective FGly residues. Linker moieties include any moiety or chemical that can be functionalized and preferably bi- or multi-functionalized with one or more aldehyde reactive groups. Particular examples include peptides, water-soluble polymers, detectable labels, other therapeutic compounds (e.g., cytotoxic compounds), biotin/streptavidin moieties, and glycans (see Hudak et al., *J Am Chem Soc.* 133:16127-35, 2011). Specific examples of glycans (or glycosides) include aminooxy glycans, such as higher-order glycans composed of glycosyl N-pentenoyl hydroxamates intermediates (supra).

Peptide linkers (or spacers) are described below. Peptide linkers can be functionalized with aldehyde reactive groups according to routine techniques in the art (see, e.g., Carrico et al., *Nat Chem Biol.* 3:321-322, 2007).

A "water-soluble polymer" refers to a polymer that is soluble in water and is usually substantially non-immunogenic, and usually has an atomic molecular weight greater than about 1,000 Daltons. Attachment of two polypeptides via a water-soluble polymer can be desirable as such modification(s) can increase the therapeutic index by increasing serum half-life, for instance, by increasing proteolytic stability and/or decreasing renal clearance. Additionally, attachment via of one or more polymers can reduce the immunogenicity of protein pharmaceuticals.

In some embodiments, the water-soluble polymer has an effective hydrodynamic molecular weight of greater than about 10,000 Da, greater than about 20,000 to 500,000 Da, greater than about 40,000 Da to 300,000 Da, greater than about 50,000 Da to 70,000 Da, usually greater than about 60,000 Da. The "effective hydrodynamic molecular weight" refers to the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of between about 200 Da and about 80,000 Da, or between about 1,500 Da and about 42,000 Da, with 2,000 to about 20,000 Da being of particular interest. Linear, branched, and terminally charged water soluble polymers are also included.

Polymers useful as linkers between aldehyde tagged polypeptides can have a wide range of molecular weights, and polymer subunits. These, subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol (PEG), methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrolidone, aspartamide, and polyoxyethylated polyols, with the dextran and dextran derivatives, dextrine and dextrine derivatives. It will be appreciated that various derivatives of the specifically described water-soluble polymers are also included.

Water-soluble polymers are known in the art, particularly the polyalkylene oxide-based polymers such as polyethylene glycol "PEG" (see Poly(ethylene glycol) Chemistry: Biotechnical and Biomedical Applications, J. M. Harris, Ed., Plenum Press, New York, N.Y. (1992); and Poly(ethylene glycol) Chemistry and Biological Applications, J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100, 992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,072,662; 5,637,749; 5,643,575; 5,650,388; 5,681,567; 5,686,110; 5,730,990; 5,739,208; 5,156,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966, incorporated by reference).

Exemplary polymers of interest include those containing a polyalkylene oxide, polyamide alkylene oxide, or derivatives thereof, including polyallkylene oxide and polyamide alkylene oxide comprising an ethylene oxide repeat unit of the formula —$(CH_2—CH^2—O)$—. Further exemplary polymers of interest include a polyamide having a molecular weight greater than about 1,000 Daltons of the formula —[C(O)—X—C(O)—NH—Y—NH]$_n$— or —[NH—Y—NH—C(O)—X—C(O)]$_n$—, where X and Y are divalent radicals that may be the same or different and may be branched or linear, and n is a discrete integer from 2-100, usually from 2 to 50, and where either or both of X and Y comprises a biocompatible, substantially non-antigenic water-soluble repeat unit that may be linear or branched.

Further exemplary water-soluble repeat units comprise on ethylene oxide of the formula —$(CH_2—CH_2—O)$— or —$(CH_2—CH_2—O)$—. The number of such water-soluble repeat units can vary significantly, with the usual number of such units being from 2 to 500, 2 to 400, 2 to 300, 2 to 200, 2 to 100, and most usually 2 to 50. An exemplary embodiment is one in which one or both of X and Y is selected from: —$((CH_2)_{n1}—(CH_2—CH_2—O)_{n2}—(CH_2)$— or —$((CH_2)_{n1}—(O—CH_2—CH_2)_{n2}—(CH_2)_{n1}—)$, where n1 is 1 to 6, 1 to 5, 1 to 4 and most usually 1 to 3, and where n2 is 2 to 50, 2 to 25, 2 to 15, 2 to 10, 2 to 8, and most usually 2 to 5. A further exemplary embodiment is one in which X is —$(CH_2—CH_2)$—, and where Y is —$(CH_2—(CH_2—CH_2—O)_3—CH_2—CH_2—CH_2)$— or —$(CH_2—CH_2—CH_2—(O—CH_2—CH_2)_3—CH_2)$—, among other variations.

For biotin/streptavidin (or avidin) moieties, the aldehyde tag(s)-containing p97 polypeptide can be covalently attached via a FGly residue to a biotin molecule that is functionalized with an aldehyde reactive group, and the aldehyde tag(s)-containing antibody can be covalently attached via a FGly residue to a streptavidin molecule that is functionalized with an aldehyde reactive group, or vice versa. The p97-biotin (or streptavidin) can then be mixed with the antibody-streptavidin (or biotin) to form a p97-antibody conjugate via the strong interaction between biotin and streptavidin.

p97-antibody conjugates can also be prepared by a various "click chemistry" techniques, including reactions that are modular, wide in scope, give very high yields, generate mainly inoffensive byproducts that can be removed by non-chromatographic methods, and can be stereospecific but not necessarily enantioselective (see Kolb et al., *Angew Chem Int Ed Engl.* 40:2004-2021, 2001). Particular examples include conjugation techniques that employ the Huisgen 1,3-dipolar cycloaddition of azides and alkynes, also referred to as "azide-alkyne cycloaddition" reactions (see Hein at al., *Pharm Res.* 25:2216-2230, 2008). Non-limiting examples of azide-alkyne cycloaddition reactions include copper-catalyzed azide-alkyne cycloaddition (CuAAC) reactions and ruthenium-catalyzed azide-alkyne cycloaddition (RuAAC) reactions.

CuAAC works over a broad temperature range, is insensitive to aqueous conditions and a pH range over 4 to 12, and tolerates a broad range of functional groups (see Himo et al, *J Am Chem Soc.* 127:210-216, 2005). The active Cu(I) catalyst can be generated, for example, from Cu(I) salts or Cu(II) salts using sodium ascorbate as the reducing agent. This reaction forms 1,4-substituted products, making i region-specific (see Hein et al., supra).

RuAAC utilizes pentamethylcyclopentadienyl ruthenium chloride [Cp*RuCl] complexes that are able to catalyze the cycloaddition of azides to terminal alkynes, regioselectively leading to 1,5-disubstituted 1,2,3-triazoles (see Rasmussen et al., *Org. Lett.* 9:5337-5339, 2007). Further, and in contrast to CuAAC, RuAAC Can also be used with internal alkynes to provide fully substituted 1,2,3-triazoles.

Certain embodiments thus include p97 polypeptides that comprise at least one unnatural amino acid with an azide side-chain or an alkyne side-chain, including internal and terminal unnatural amino acids (e.g., N-terminal, C-terminal). Certain of these p97 polypeptides can be formed by in vivo or in vitro (e.g., cell-free systems) incorporation of unnatural amino acids that contain azide side-chains or alkyne side-chains. Exemplary in vivo techniques include cell culture techniques, for instance, using modified *E. coli* (see Travis and Schultz, *The Journal of Biological Chemistry.* 285:11039-44, 2010; and Deiters and Schultz, *Bioorganic & Medicinal Chemistry Letters.* 15:1521-1524, 2005), and exemplary in vitro techniques include cell-free systems (see Bundy, *Bioconjug Chem.* 21:255-63, 2010).

In some embodiments, a p97 polypeptide that comprises at least one unnatural amino acid with an azide side-chain is conjugated by azide-alkyne cycloaddition to an antibody that comprises at least one unnatural amino acid with an alkyne side-chain. In other embodiments, a p97 polypeptide that comprises at least one unnatural amino acid with an alkyne side-chain is conjugated by azide-alkyne cycloaddition to an antibody that comprises at least one unnatural amino acid with an azide side-chain. Hence, certain embodiments include conjugates that comprise a p97 polypeptide covalently linked to an antibody via a 1,2,3-triazole linkage. In specific embodiments, the antibody is an anti-Her2/neu antibody such as Trastuzumab.

Specific p97-antibody conjugates can be formed by the following CuAAC-based or RuAAC-based reactions, to comprise the following respective structures (I) or (II):

where R is a p97 polypeptide and R' is an antibody or antigen-binding fragment thereof; or where R is an antibody or antigen-binding fragment thereof and R' is a p97 polypeptide.

As noted above, in some embodiments the unnatural amino acid with the azide side-chain and/or the unnatural amino acid with alkyne side-chain are terminal amino acids (N-terminal, C-terminal). In certain embodiments, one or more of the unnatural amino acids are internal. Specific embodiments include a p97 polypeptide that comprises an N-terminal unnatural amino acid with an azide side-chain conjugated to an antibody that comprises an N-terminal unnatural amino acid with an alkyne side-chain. Other embodiments include a p97 polypeptide that comprises a C-terminal unnatural amino acid with an azide side-chain conjugated to an antibody that comprises a C-terminal unnatural amino acid with an alkyne side-chain. Still other embodiments include a p97 polypeptide that comprises an N-terminal unnatural amino acid with an azide side-chain conjugated to an antibody that comprises a C-terminal unnatural amino acid with an alkyne side-chain. Further embodiments include a p97 polypeptide that comprises a C-terminal unnatural amino acid with an azide side-chain conjugated to an antibody that comprises an N-terminal unnatural amino acid with an alkyne side-chain.

Other embodiments include a p97 polypeptide that comprises an N-terminal unnatural amino acid with an alkyne side-chain conjugated to an antibody that comprises an N-terminal unnatural amino acid with an azide side-chain. Still further embodiments include a p97 polypeptide that comprises a C-terminal unnatural amino acid with an alkyne side-chain conjugated to an antibody that comprises a C-terminal unnatural amino acid with an azide side-chain. Additional embodiments include a p97 polypeptide that comprises an N-terminal unnatural amino acid with an alkyne side-chain conjugated to an antibody that comprises a C-terminal unnatural amino acid with an azide side-chain. Still further embodiments include a p97 polypeptide that comprises a C-terminal unnatural amino acid with an alkyne side-chain conjugated to an antibody that comprises an N-terminal unnatural amino acid with an azide side-chain.

Also included are methods of producing a p97-antibody conjugate, comprising: (a) performing an azide-alkyne cycloaddition reaction between (i) a p97 polypeptide that comprises at least one unnatural amino acid with an azide side-chain and an antibody or antigen-binding fragment thereof that comprises at least one unnatural amino acid with an alkyne side-chain; or (ii) a p97 polypeptide that comprises at least one unnatural amino acid with an alkyne side-chain and an antibody or antigen-binding fragment thereof that comprises at least one unnatural amino acid with an azide side-chain; and (b) isolating a p97-antibody conjugate from the reaction, thereby producing a p97-antibody conjugate.

In the case where the p97-antibody conjugate is a fusion polypeptide, the fusion polypeptide may generally be prepared using standard techniques, including chemical conjugation. Preferably, however, a fusion polypeptide is expressed as a recombinant polypeptide in an expression system, as described below. Fusion polypeptides of the invention can contain one or multiple copies of a p97 polypeptide sequence and may contain one or multiple copies of an antibody or antigen-binding fragment thereof (e.g., anti-Her2/neu antibody or antigen-binding fragment thereof), present in any desired arrangement.

A peptide linker sequence may be employed to separate first and second polypeptide components by a distance sufficient to ensure that each polypeptide folds into its secondary and tertiary structures. Such a peptide linker sequence May be

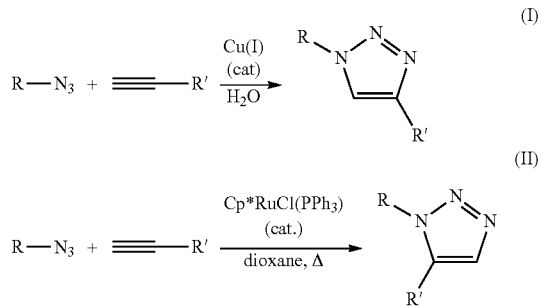

incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide spacer comprises about 1, 5, 10, 15, 20, 25, 30, 35, 40, 45, 50 or more amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., Gene 40:39-46, 1985; Murphy et al., PNAS USA. 83:8258-8262, 1986; U.S. Pat. No. 4,935,233 and U.S. Pat. No. 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: $[G]_x$, $[S]_x$, $[N]_x$, $[GS]_x$, $[GGS]_x$, $[GSS]_x$, $[GSGS]_x$ (SEQ ID NO:7), $[GGSG]_x$ (SEQ ID NO:8), $[GGGS]_x$ (SEQ ID NO:9), $[GGGGS]_x$ (SEQ ID NO:10), $[GN]_x$, $[GGN]_x$, $[GNN]_x$, $[GNGN]_x$ (SEQ ID NO:11), $[GGNG]_x$ (SEQ ID NO:12), $[GGGN]_x$ (SEQ ID NO:13), $[GGGGN]_x$ (SEQ ID NO:14) linkers, where $x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art.

In specific embodiments, the linker sequence comprises a Gly3 linker sequence, which includes three glycine residues. In particular embodiments, flexible linkers can be rationally designed using a computer program capable Of modeling both DNA-binding sites and the peptides themselves (Desjarlais & Berg, PNAS. 90:2256-2260, 1993; and PNAS. 91:11099-11103, 1994) or by phage display methods.

The peptide linkers may be physiologically stable or may include a releasable linker such as a physiologically degradable or enzymatically cleavable linker (e.g., protealytically cleavable linker). In certain embodiments, one or more releasable linkers can result in a shorter half-life and more rapid clearance of the conjugate. These and related embodiments can be used, for example, to enhance the solubility and blood circulation lifetime of p97-antibody conjugates in the bloodstream, while also delivering an antibody into the bloodstream (or across the BBB) that, subsequent to linker degradation, is substantially free of the p97 sequence. These aspects are especially useful in those cases where antibodies, when permanently conjugated to a p97 sequence, demonstrate reduced activity. By using the linkers as provided herein, such antibodies can maintain their therapeutic activity when in conjugated form. In these and other ways, the properties of the p97-antibody conjugates can be more effectively tailored to balance the bioactivity and circulating half-life of the antibodies over time.

In particular embodiments, a releasable linker has a half life at pH 7.4, 25° C., e.g., a physiological pH, human body temperature (e.g., in vivo, in serum, in a given tissue), of about 30 minutes, about 1 hour, about 2 hours, about 3 hours, about 4 hours, about 5 hours, about 6 hours, about 12 hours, about 18 hours, about 24 hours, about 36 hours, about 48 hours, about 72 hours, or about 96 hours or more or any intervening half-life. One having skill in the art would appreciate that the half life of a p97-antibody conjugate can be finely tailored by using a particular releasable linker.

In certain embodiments, however, any one or more of the peptide linkers are optional. For instance, linker sequences may not required when the first and second polypeptides have non-essential N-terminal and/or C-terminal amino acid regions that can be used to separate the functional domains and prevent steric interference.

In other embodiments, a p97 antibody conjugate as described herein may be further conjugated or operably linked to another therapeutic compound. The conjugate may include, for example, a cytotoxic agent, a chemotherapeutic agent, a cytokine, an anti-angiogenic agent, a tyrosine kinase inhibitor, a toxin, a radioisotope, or other therapeutically active agent.

Fusion Polynucleotides, Host Cells and Recombinant Production

The present invention further provides in certain embodiments isolated polynucleotides encoding p97 polypeptides and 97-antibody conjugates of the invention, such as a fusion polypeptide comprising an anti-Her2/neu antibody or antigen binding fragment and a p97 polypeptide sequence or fragment or derivative thereof. Also included are isolated or recombinant polynucleotides that encode aldehyde-tag containing p97 polypeptides and antibodies, and p97 polypeptides and antibodies that comprise at least one unnatural amino acid, for instance, unnatural amino acids with an azide side-chain or alkyne side-chain, and related host cells. These and related embodiments can be used for the recombinant production of the p97-antibody fusion proteins and non-fusion conjugates described herein.

For fusion proteins, DNA sequences encoding the p97 and antibody (e.g., anti-Her2/neu antibody) components may be assembled separately, and then ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding, the second polypeptide. This permits translation into a single fusion polypeptide that retains the biological activity of both component polypeptides.

Similar techniques, mainly the arrangement of regulatory elements such as promoters, stop codons, and transcription termination signals, can be applied to the recombinant production of non-fusion proteins, for instance, p97 polypeptides and antibodies for the production of non-fusion conjugates.

Polynucleotides and fusion polynucleotides of the invention can contain one or multiple copies of a nucleic acid encoding a p97 polypeptide sequence, and/or may contain one or multiple copies of a nucleic acid encoding an antibody or antigen-binding fragment thereof.

In some embodiments, a nucleic acids encoding a subject p97 polypeptide, antibody, and/or p97-antibody fusion are introduced directly into a host cell, and the cell incubated under conditions sufficient to induce expression of the encoded polypeptide(s). The polypeptide sequences of this disclosure may be prepared using standard techniques well known to those of skill in the art in combination with the polypeptide and nucleic acid sequences provided herein.

Therefore, according to certain related embodiments, there is provided a recombinant host cell which comprises a polynucleotide or a fusion polynucleotide as described herein. Expression of a p97 polypeptide, antibody, or p97-antibody fusion in the host cell may conveniently be achieved by culturing under appropriate conditions recombinant host cells containing the polynucleotide. Following production by expression, the polypeptide(s) may be isolated and/or purified using any suitable technique, and then used as desired.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, HEK-293 cells, NSO mouse melanoma cells and many others. A common, preferred bacterial host is *E. coli*.

The expression of antibodies and antigen-binding fragments in prokaryotic cells such as *E. coli* is well established in the art. For a review, see for example Pluckthun, A. Bio/Technology. 9:545-551 (1991). Expression in eukaryotic cells in culture is also available to those skilled in the art as an option for production of antibodies or antigen-binding fragments thereof, see recent reviews, for example Ref, M. E. (1993) *Curr. Opinion Biotech.* 4: 573-576; Trill J. J. et al. (1995) *Curr. Opinion Biotech* 6: 553-560.

Suitable vectors can be chosen or constructed, containing appropriate regulatory sequences, including promoter sequences, terminator sequences, polyadenylation sequences, enhancer sequences, marker genes and Other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described polypeptides, and which further expresses or is capable of expressing a selected gene of interest, such as a gene encoding any herein described polypeptide. The term includes the progeny of the parent cell, whether or not the progeny are identical in morphology or in genetic make-up to the original parent, so long as the selected gene is present. Host cells may be chosen for Certain characteristics, for instance, the expression of a formylglycine generating enzyme (FGE) to convert a cysteine or serine residue within a sulfatase motif into a formylglycine (FGly) residue, or the expression of aminoacyl tRNA synthetase(s) that can incorporate unnatural amino acids into the polypeptide, including unnatural amino acids with an azide side-chain, alkyne side-chain, or other desired side-chain, to facilitate conjugation.

Accordingly there is also contemplated a method comprising introducing such nucleic acid(s) into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide, such as a p97 polypeptide, antibody, or p97-antibody fusion protein as described herein.

Illustratively, a peptide linker/spacer sequence may be employed to separate the components of a p97-antibody fusion protein by a distance sufficient to ensure that each polypeptide folds into its secondary and/or tertiary structures, if desired. Such a peptide linker sequence can be incorporated into a fusion polypeptide using standard techniques well known in the art.

Compositions and Methods of Use

The present disclosure also provides compositions comprising the p97-antibody conjugates and compositions of the invention and administration of such compositions for therapeutic purposes.

Administration of the conjugates described herein, in pure form or in an appropriate pharmaceutical composition, can be carried out via any of the accepted modes of administration of agents for serving similar utilities. The pharmaceutical compositions can be prepared by combining a conjugate or conjugate-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

Carriers can include, for example, pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxameri (PLURONICS™), and the like.

The present invention provides therapeutic compositions comprising a p97 polypeptide sequence and any therapeutic and/or diagnostic antibody or antigen-binding fragment thereof (e.g., an antibody or fragment that specifically binds the human Her2/neu protein or other antibody described herein).

In certain aspects, the p97 polypeptide sequence and the antibody or fragment thereof are each, individually or as a pre-existing conjugate, bound to or encapsulated within a particle, e.g., a nanoparticle, bead, lipid formulation, lipid particle, or liposome, e.g., immunoliposome. For instance, in particular embodiments, the p97 polypeptide sequence is bound to the surface of a particle, and the antibody or fragment thereof is bound to the surface of the particle and/or encapsulated within the particle. In certain of these and related embodiments, the p97 polypeptide and the antibody are covalently or operatively linked to each other only via the particle itself (e.g., nanoparticle, liposome), and are not covalently linked to each other in any other way; that is, they are bound individually to the same particle. In other embodiments, the p97 polypeptide and the antibody are first covalently conjugated to each other, as described herein (e.g., via a linker molecule), and are then bound to or encapsulated within a particle (e.g., immunoliposome, nanoparticle). In specific embodiments, the particle is a liposome, and the composition comprises one or more p97 polypeptides, one or more antibodies or antigen-binding fragments thereof, and a mixture of lipids to form a liposome (e.g., phospholipids, mixed lipid chains with surfactant properties). In some aspects, the p97 polypeptide and the antibody (or antigen-binding fragment) are individually mixed with the lipid/liposome mixture, such that the formation of liposome structures operatively links the p97 polypeptide and antibody without the need for covalent conjugation. In other aspects, the p97 polypeptide and the antibody (or antigen-binding fragment) are first covalently conjugated to each other, as described herein, and then mixed with lipids to form a liposome. The p97 polypeptide, the antibody, or the p97 antibody-conjugate may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other cytotoxic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The conjugate-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described conjugate in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a conjugate of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a conjugate as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a conjugate as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., conjugate) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the conjugates of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising conjugates of the invention and each active agent in its own separate pharmaceutical dosage formulation. For example, a conjugate as described herein and the other active agent can be administered to the patient together in a single oral dosage composition such as a tablet or capsule, or each agent administered in separate oral dosage formulations. Similarly, a conjugate as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising conjugates and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of conjugate compositions of this disclosure in combination with one or More other therapeutic agents. Such therapeutic agents may be accepted in the art as a standard treatment for a particular disease state as described herein, such as rheumatoid arthritis, inflammation or cancer. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the conjugates disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the conjugates described herein. In one embodiment, the conjugate is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

The compositions may be administered to an individual afflicted with a disease as described herein, including, but not limited to neoplastic diseases, metabolic diseases, neurological diseases, infections, cardiovascular diseases, inflammatory diseases, autoimmune diseases, and diseases associated with abnormal angiogenesis. Particular diseases include Her2/neu-expressing disorders, such as Her2/neu-expressing cancers.

Certain embodiments include methods of treating cancer in a subject, comprising administering to the subject a p97-antibody conjugate described herein, or a composition comprising a p97-antibody conjugate and a pharmaceutically acceptable carrier or excipient. "Cancer" relates generally to a class of diseases or conditions in which a group of cells display one or more of uncontrolled growth (i.e., division beyond normal limits), invasion (i.e., intrusion on and destruction of adjacent tissues), and/or metastasis (i.e., spread to other locations in the body via lymph or blood). These malignant properties of cancers differentiate them from benign cancers, which are self-limited, and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form solid tumors, but some, e.g., leukemia, do not necessarily form tumors. For those cancers that form tumors, the terms cancer (cell) and tumor (cell) are used interchangeably. General examples include primary and metastatic cancers. Particular examples of primary or metastatic cancers include, without limitation, prostate cancers, breast cancers, gastrointestinal cancers (e.g., colon cancers, colorectal carcinoma, rectal cancers), lung cancers (e.g., small lung cell cancers, non-small lung cell carcinomas), ovarian cancers, testicular cancers, head and neck cancers, stomach cancers, bladder Cancers (e.g., urinary bladder carcinomas), pancreatic cancers, liver cancers, kidney, cancers (e.g., renal cell carcinomas), squamous cell carcinomas, primary and metastatic CNS or brain cancers (e.g., neuroblastomas, glioblastomas), melanomas such as malignant melanomas, non-melanoma skin cancers, thyroid cancers (e.g., medullary thyroid cancers (MTCs)), endometrial cancers, epithelial tumors bone cancers, and hematopoietic cancers, such as lymphomas (e.g., T-cell lymphomas such as cutaneous T-cell lymphoma (CTCL), B-cell lymphomas, small lymphocytic lymphoma, mangle cell lymphoma, anaplastic large cell lymphoma (ALCL), follicular lymphoma), leukemias (e.g., chronic lymphocytic leukemia (CLL), hairy cell leukemia, acute lymphoblastic leukemia, myelocytic leukemia, acute myeloid or myelogenous leukemia), multiple myeloma, Hodgkin's lymphoma, and non-Hodgkin's lymphoma. Hence, in certain embodiments, a subject has one or more of the above-described cancers.

Certain embodiments relate to methods for treating a cancer of the central nervous system (CNS), optionally the brain. In some embodiments, the cancer is a primary cancer of the CNS, such as a primary cancer of the brain. For instance, the methods can be for treating a glioma, meningioma, pituitary adenoma, vestibular schwannoma, primary CNS lymphoma, or primitive neuroectodermal tumor (medulloblastoma). In some embodiments, the glioma is an astrocytoma, oligodendroglioma, ependymoma, or a choroid plexus papilloma. In certain embodiments, the primary CNS or brain cancer is glioblastoma multiforme, such as a giant cell gliobastoma or a gliosarcoma.

In particular embodiments, the cancer is a metastatic cancer of the CNS, for instance, a cancer that has metastasized to the brain. Examples of such cancers include, without limitation, breast cancers, lung cancers, genitourinary tract cancers, gastrointestinal tract cancers (e.g., colorectal cancers, pancreatic carcinomas), osteosarcomas, melanomas, head and neck cancers, prostate cancers (e.g., prostatic adenocarcinomas), and hematopoietic cancers such as lymphomas. Certain embodiments thus include methods for treating, inhibiting or preventing metastasis of a cancer by administering to a patient a therapeutically effective amount of a p97-antibody conjugate described herein (e.g., in an amount that, following administration, inhibits, prevents or delays metastasis of an antibody-resistant cancer in a statistically significant manner, i.e., relative to an appropriate control as will be known to those skilled in the art). In particular embodiments, the subject has a cancer that has not yet metastasized to the central nervous system, including one or more of the above-described cancers, among others known in the art.

In some aspects, the cancer or cancer cell is associated with expression of at least one of Her2/neu, Her1/EGF receptor, Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein, alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), or mesothelin. In specific aspects, the monoclonal antibody-portion of the p97-antibody conjugate specifically binds to one or more of the foregoing cancer-associated antigens, or cancer antigens.

Particular aspects relate to the treatment of cancers associated with the expression of Her2/neu. For example, one embodiment of the invention provides a method for treating, inhibiting or preventing a cancer including, but not limited to, Her2/neu-expressing breast cancer and metastatic breast cancer, by administering to a patient a therapeutically effective amount of a herein disclosed conjugate. An amount that, following administration, inhibits, prevents or delays the progression and/or metastasis of a cancer in a statistically significant manner (i.e., relative to an appropriate control as will be known to those skilled in the art) is considered effective.

Another embodiment provides a method for treating, inhibiting or preventing metastasis of a Her2/neu-expressing breast cancer by administering to a patient a therapeutically effective amount of a herein disclosed conjugate (e.g., in an amount that, following administration, inhibits, prevents or delays metastasis of a cancer in a statistically significant manner, i.e., relative to an appropriate control as will be known to those skilled in the art).

Particular aspects include the use of p97-trastuzumab for the treatment of patients with metastatic breast cancer whose tumors overexpress the Her2 protein and have received one or more chemotherapy regiments for their metastatic disease. Some aspects include p97-trastuzumab in combination with paclitaxel for the treatment of patients with metastatic breast cancer whose tumors overexpress the Her2 protein and who have not received chemotherapy for their metastatic disease.

Specific aspects relate to the treatment of cancers associated with the expression of Her1/EGFR. For instance, certain aspects include treatment of a metastatic colorectal cancer or a head and neck cancer, where the p97-antibody conjugate specifically binds to Her1/EGFR and is an EGFR antagonist. In some aspects, the cancer is an EGFR-expressing metastatic colorectal cancer, and is optionally KRAS wild-type. In particular aspects, the p97-antibody conjugate is administered to a subject with EGFR-expressing metastatic colorectal cancer after failure of both irinotecan- and oxiplatin-based regimens. In some aspects, the subject with metastatic colorectal cancer is intolerant to irinotecan-based regimens or is refractory to irinotecan-based chemotherapy. In other aspects, the cancer is a locally or regionally advanced squamous cell carcinoma of the head and neck, a recurrent locoregional disease or metastatic squamous cell carcinoma of the head and neck, or a recurrent or metastatic squamous cell carcinoma of the head and neck progressing after platinum-based therapy. In certain of these and related embodiments, the antibody portion of the p97-antibody conjugate is cetuximab, or an antigen-binding fragment thereof.

In specific embodiments, the p97-antibody conjugate comprises an antibody that specifically binds to human Her-2/neu, such as trastuzumab, and the subject optionally has breast cancer or metastatic breast cancer, or a (metastatic) cancer of the CNS, as described herein. In other embodiments, the p97-antibody conjugate comprises an antibody that specifically binds to GD2, such as 3F8, and the subject optionally has a neuroblastoma. In certain embodiments, the p97-antibody conjugate comprises an antibody that specifically binds to CA-125, such as abagovomab, and the subject optionally has an ovarian cancer.

In particular embodiments, the p97-antibody conjugate comprises an antibody that specifically binds to EpCAM, such as adecatumumab, and the subject optionally has a prostate cancer or breast cancer. In specific embodiments, the p97-antibody conjugate comprises an antibody that specifically binds to CD20, such as afutuzumab, and the subject optionally has a lymphoma. In specific embodiments, the p97-antibody conjugate comprises an antibody that specifically binds to CD52, such as alemtuzumab, and the subject optionally has chronic lymphocytic leukemia (CLL) or CTCL.

In specific embodiments, the p97-antibody conjugate comprises an antibody that specifically binds to VEGF-R2, such as alacizumab (pegol). In specific embodiments, the p97-antibody conjugate comprises an antibody that Specifically binds to HLA-DR, such as apolizumab, and the subject optionally has a hematological cancer. In specific embodiments, the p97-antibody conjugate comprises an antibody that specifically binds to BAFF, such as belimumab, and the subject optionally has a hematopoietic cancer such as Non-Hodgkin's lymphoma.

In specific embodiments, the p97-antibody conjugate comprises an antibody that specifically binds to VEGF-A, such as bevacizumab, and the subject optionally has a metastatic cancer or colorectal cancer. In specific embodiments, the p97-antibody conjugate comprises an antibody that specifically binds to CD44, such as bivatuzumab (mertansine), and the subject optionally has a squamous cell carcinoma. In specific embodiments, the p97-antibody conjugate comprises an antibody that specifically binds to CD30, such as brentuximab vedotin, and the subject optionally has a hematological cancer such as anaplastic large cell lymphoma (ALCL) or Hodgkin's lymphoma.

In specific embodiments, the p97-antibody conjugate comprises an antibody that specifically binds to mucin, such as cantuzumab (mertansine), and the subject optionally has a colorectal cancer. In specific embodiments, the p97-antibody conjugate comprises an antibody that specifically binds to PSMA, such as capromab, and the subject optionally has a prostate cancer. In specific embodiments, the p97-antibody conjugate comprises an antibody that specifically binds to EpCAM and optionally CD3, such as cetuximab, and the subject optionally has a (metastatic) colorectal cancer or a head and neck cancer.

In certain embodiments, the p97-antibody conjugate comprises an antibody that specifically binds to EpCAM, such as citatuzumab (bogatox), and the subject optionally has a solid tumor such as ovarian cancer. In particular embodiments, the p97-antibody conjugate comprises an antibody that specifically binds to the IGF-1 receptor, such as cixutumumab, and the subject optionally has a solid tumor. In specific embodiments, the p97-antibody conjugate comprises an antibody that specifically binds to MUC1, such as clivatuzumab (tetraxetan), and the subject optionally has a pancreatic cancer.

In specific embodiments, the p97-antibody conjugate comprises an antibody that specifically binds to CD40, such as dacetuzumab, and the subject optionally has a hematologic cancer. In some embodiments, the p97-antibody conjugate comprises an antibody that specifically binds to GD3 ganglioside, such as ecromeximab, and the subject optionally has a malignant melanoma. In specific embodiments, the p97-antibody conjugate comprises an antibody that specifically binds to EpCAM, such as edrecolomab, and the subject optionally has a colorectal carcinoma.

In specific embodiments, the p97-antibody conjugate comprises an antibody that specifically binds to SLAMF7, such as elotuzumab, and the subject optionally has a multiple myeloma. In specific embodiments, the p97-antibody conjugate comprises an antibody that specifically binds to integrin $\alpha_v\beta_3$, such as etaracizumab, and the subject optionally has a melanoma, prostate cancer, ovarian cancer, or other solid tumor. In certain embodiments, the p97-antibody conjugate comprise an antibody that specifically binds to folate receptor 1, such as farletuzumab, and the subject optionally has an ovarian cancer.

In specific embodiments, the p97-antibody conjugate comprises an antibody that specifically binds to the IGF-1 receptor, such as figitumumab, and the subject optionally has adrenocortical carcinoma or non-small cell lung carcinoma. In specific embodiments, the p97-antibody conjugate comprises an antibody that specifically binds to glycoprotein 75, such as flanvotumab, and the subject optionally has a melanoma. In specific embodiments, the p97-antibody conjugate comprises an antibody that specifically binds to CD80, such as galiximab, and the subject optionally has a B-cell lymphoma.

In particular embodiments, the p97-antibody conjugate comprises an antibody that specifically binds to CD33, such as gemtuzumab (ozogamicin), and the subject optionally has a myelogenous leukemia. In specific embodiments, the p97-antibody conjugate comprises an antibody that specifically binds to CA-IX such as girentuximab, and the subject optionally has a renal cell carcinoma. In further embodiments, the p97-antibody conjugate comprises an antibody that specifically binds to GPMNB, such as glembatumumab (vedotin), and the subject optionally has a melanoma or breast cancer.

In specific embodiments, the p97-antibody conjugate comprises an antibody that specifically binds to CD20, such as ibritumomab tiuxetan, and the subject optionally has a hematopoietic cancer such as non-Hodgkin's lymphoma. In some embodiments, the p97-antibody conjugate comprises an antibody that specifically binds to CTLA-4, such as ipilimumab (MDX-101), and the subject optionally has a solid tumor such as a melanoma. In specific embodiments, the p97-antibody conjugate comprises an antibody that specifically binds to CD51, such as intetumumab, and the subject optionally has a solid tumor such as prostate cancer or melanoma.

In particular embodiments, the p97-antibody conjugate comprises an antibody that specifically binds to CD30, such as iratumumab, and the subject optionally has a hematopoietic cancer such as Hodgkin's lymphoma. In specific embodiments, the p97-antibody conjugate comprises an antibody that specifically binds to CEA, such as labetuzumab, and the subject optionally has a colorectal cancer. In specific embodiments, the p97-antibody conjugate comprises an antibody that specifically binds to CD40, such as lucatumumab, and the subject optionally has a hemotopoietic cancer such as multiple myeloma, non-Hodgkin's lymphoma, or Hodgkin's lymphoma.

In certain embodiments, the p97-antibody conjugate comprises an antibody that specifically binds to CD23, such as lumiliximab, and the subject optionally has CLL. In specific embodiments, the p97-antibody conjugate comprises an antibody that specifically binds to EGFR, such as matuzumab, and the subject optionally has a colorectal, lung, or stomach cancer. In specific embodiments, the p97-antibody conjugate comprises an antibody that specifically binds to CD74, such as milatuzumab, and the subject optionally has a hematological cancer such as multiple myeloma.

In some embodiments, the p97-antibody conjugate comprises an antibody that specifically binds to GD3 ganglioside, such as mitumomab, and the subject optionally has a small cell lung carcinoma. In specific embodiments, the p97-antibody conjugate comprises an antibody that specifically binds to 5T4, such as naptumomab (estafenatox), and the subject optionally has a non-small cell lung carcinoma or renal cell carcinoma. In specific embodiments, the p97-antibody conjugate comprises an antibody that specifically binds to EGFR, such as necitumumab, and the subject optionally has a non-small cell lung carcinoma.

In particular embodiments, the p97-antibody conjugate comprises an antibody that specifically binds to EGFR, such as nimotuzumab, and the subject optionally has a squamous cell carcinoma, head and neck cancer, nasopharyngeal cancer, or glioma. In specific embodiments, the p97-antibody conjugate comprises an antibody that specifically binds to CD20, such as ofatumumab, and the subject optionally has a hematopoietic cancer such as CLL. In specific embodiments, the p97-antibody conjugate comprises an antibody that specifically binds to CA-125, such as oregovomab, and the subject optionally has an ovarian cancer.

In specific embodiments, the p97-antibody conjugate comprises an antibody that specifically binds to EGFR, such as panitumumab, and the subject optionally has a colorectal cancer. In some embodiments, the p97-antibody conjugate comprises an antibody that specifically binds to vimentin, such as pritumumab, and the subject optionally has a brain cancer. In specific embodiments, the p97-antibody conjugate comprises an antibody that specifically binds to CD20, such as rituximab, and the subject optionally has a hematopoietic cancer such as a lymphoma or leukemia.

In certain embodiments, the p97-antibody conjugate comprises an antibody that specifically binds to CD20, such as tositumomab, and the subject optionally has a lymphoma such as follicular lymphoma. In specific embodiments, the p97-antibody conjugate comprises an antibody that specifically binds to GD2, such as TRBS07, and the subject optionally has a melanoma. In specific embodiments, the p97-antibody conjugate comprises an antibody that specifically binds to integrin $\alpha_5\beta_1$, such as volociximab, and the subject optionally has a solid tumor.

In particular embodiments, the p97-antibody conjugate comprises an antibody that specifically binds to tumor antigen CTAA16.88, such as votumumab, and the subject optionally has a colorectal tumor. In specific embodiments, the p97-antibody conjugate comprises an antibody that specifically binds to EGFR, such as zalutumumab, and the subject optionally has a squamous cell carcinoma of the head and neck.

As noted above, the use of p97-antibody conjugates for treating cancers can be combined with other therapeutic modalities. For example, a composition comprising a p97-antibody conjugate can be administered to a subject before, during, or after other therapeutic interventions, including symptomatic care, radiotherapy, surgery, transplantation, immunotherapy, hormone therapy, photodynamic therapy, chemotherapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

In specific combination therapies, the antibody portion of the p97-antibody conjugate comprises cetuximab, and the p97-cetuximab conjugate is Used for treating a subject with locally or regionally advanced squamous cell carcinoma of the head and neck in combination with radiation therapy. In other aspects, the p97-cetuximab conjugate is used for treating a subject with recurrent locoregional disease or metastatic squamous cell carcinoma of the head and neck in combination with platinum-based therapy with 5-fluorouracil (5-FU). In some aspects, the p97-cetuximab conjugate is used in combination with irinotecan for treating a subject with EGFR-expressing colorectal cancer and that is refractory to irinotecan-based chemotherapy.

Methods for identifying subjects with one or more of the diseases or conditions described herein are known in the art.

For in vivo use for the treatment of human disease, the conjugates described herein are generally incorporated into a pharmaceutical composition prior to administration. A pharmaceutical composition comprises one or more of the conjugates described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising conjugates as described herein may be prepared with carriers that protect the conjugates against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The following Examples are offered by way of illustration and not by way of limitation.

EXAMPLES

Example 1

Conjugation of p97 to Anti-Her2/Neu Antibodies

Trastuzumab, a humanized monoclonal antibody specific for the Her2/neu protein and used clinically in the treatment of HER2+ breast cancer, was chemically linked to a p97 delivery vector (Transcend; BiOasis), as described below.
Initial Preparation of Antibody
1. Approximately 100 mg (formulated weight including excipients, etc.) of "BTA" antibody (Roche), which specifically binds to the human Her2/neu protein, was dissolved in 1.5 ml of deionized water and buffer-exchanged into 0.1 M potassium phosphate buffer pH 7.5 on a single PD10 column (GE 170851-01), yielding 3.0 ml of an antibody solution at 18.10 mg/ml as indicated by UV-visible spectrophotometry at 280 nm, and assuming an absorbance of 1.40 at this wavelength for a 1 mg/ml solution of antibody (Antibody A).

2. Approximately 100 mg (formulated weight including excipients, etc.) of "BTA" antibody (Roche) was dissolved in 4.0 ml of deionised water and buffer-exchanged into 0.1 M potassium phosphate buffer pH 7.5 on three PD10 columns (GE 170851-01), yielding 8.1 ml of an antibody solution at 6.50 mg/ml as indicated by UV-visible spectrophotometry at 280 nm, and assuming an absorbance of 1.40 at this wavelength for a 1 mg/ml solution of antibody (Antibody B).

Cy5.5 Labeling of Antibody

3. To 53.4 mg (2.95 ml) of Antibody B was added 1.89 mg (189 ul) of a 10.0 mg/ml solution of Cy5.5 NHS ester (Lumiprobe 24020) in DMSO, equivalent to a 7:1 Cy5.5: antibody excess.

4. The dye-antibody reaction was allowed to continue for 60 minutes at 20° C.

5. The crude antibody-dye conjugate was purified using size exclusion chromatography on two PD10 columns, using 0.1 M potassium phosphate pH 7.5 as eluent, to remove low-molecular weight by-products. This yielded a solution of dye-labelled antibody with an antibody concentration of 9.45 mg/ml and with an apparent incorporation of 2.01 dye molecules per antibody molecule as indicated by UV-visible spectrophotometry at 280 nm and 673 nm, and assuming an absorbance of 1.40 at this wavelength for a 1 mg/ml solution of antibody and a molar extinction coefficient of 133,000 $M^{-1}$ $cm^{-1}$ at 673 nm for Cy5.5 (Dye-Labelled Antibody B)

Incorporation of Maleimides into Unlabelled Antibody

6. To 40 mg (6.15 ml) of Antibody A was added 0.31 mg (62 ul) of a 5.0 mg/ml solution of 4[N-maleimidomethyl]cyclohexane-1-carboxylate (SMCC, Thermo 22360) in DMSO, equivalent to an SMCC: antibody excess of 3.5:1.

7. The antibody activation reaction was allowed to continue for 60 minutes at 20° C.

8. The crude maleimide-activated unlabelled antibody was purified using size exclusion chromatography on four PD10 columns to remove low-molecular weight by-products, using 50 mM potassium phosphate, 150 mM sodium chloride, 5 mM EDTA buffer pH 7.0 buffer as eluent. This yielded a solution of maleimide-activated, unlabelled antibody with an antibody concentration of 3.34 mg/ml assuming an absorbance of 1.40 at this wavelength for a 1 mg/ml solution of antibody. (Maleimide-Activated Unlabelled Antibody A1)

9. To 5 mg (769 ul) of Antibody A was added 0.17 mg (33 ul) of a 5.0 mg/ml solution of 4-[N-maleimidomethyl]cyclohexane-1-carboxylate (SMCC, Thermo 22360) in DMSO, equivalent to an SMCC: antibody excess of 15:1.

10. The antibody activation reaction was allowed to continue for 60 minutes at 20° C.

11. The crude maleimide-activated, unlabelled antibody was purified using size exclusion chromatography on a single PD10 column to remove low-molecular weight by-products, using 50 mM potassium phosphate, 150 mM sodium chloride, 5 mM EDTA buffer pH 7.0 buffer as eluent. This yielded a solution of maleimide-activated, unlabelled antibody with an antibody concentration of 2.36 mg/ml assuming an absorbance of 1.40 at this wavelength for a 1 mg/ml solution of antibody. (Maleimide-Activated Unlabelled Antibody A2)

Incorporation of Maleimides into Cy5.5-Labelled Antibody

12. To 40 mg (4.23 ml) of Dye-Labelled Antibody B was added 0.45 mg (89 ul) of a 5.0 mg/ml solution of 4[N-maleimidomethyl]cyclohexane-1-carboxylate (SMCC, Thermo 22360) in DMSO, equivalent to an SMCC: antibody excess of 5:1.

13. The antibody activation reaction was allowed to continue for 60 minutes at 20° C.

14. The crude maleimide-activated, dye-labelled antibody was purified using size exclusion chromatography on three PD10 columns to remove low-molecular weight by-products, using 50 mM potassium phosphate, 150 mM sodium chloride, 5 mM EDTA buffer pH 7.0 buffer as eluent. This yielded a solution of maleimide-activated, dye-labelled antibody with an antibody concentration of 4.46 mg/ml and with an apparent incorporation of 1.05 dye molecules per antibody molecule as indicated by UV-visible spectrophotometry at 280 nm and 673 nm, and assuming an absorbance of 1.40 at this wavelength for a 1 mg/ml solution of antibody and a molar extinction coefficient of 133,000 $M^{-1}$ $cm^{-1}$ at 673 nm for Cy5.5. (Maleimide-Activated Dye-Labelled Antibody B1)

15. To 5 mg (529 ul) of Dye-Labelled Antibody B was added 0.20 mg (40 ul) of a 5.0 mg/ml solution of 4-[N-maleimidomethyl]cyclohexane-1-carboxylate (SMCC, Thermo 22360) in DMSO, equivalent to an 18:1 SMCC: antibody excess.

16. The antibody activation reaction was allowed to continue for 60 minutes at 20° C.

17. The crude maleimide-activated, dye-labelled antibody was purified using size exclusion chromatography on a single PD10 column to remove low-molecular weight by-products, using 50 mM potassium phosphate, 150 mM sodium chloride, 5 mM EDTA buffer pH 7.0 buffer as eluent. This yielded a solution of maleimide-activated, dye-labelled antibody with an antibody concentration of 1.85 mg/ml and with an apparent incorporation of 0.66 dye molecules per antibody molecule as indicated by UV-visible spectrophotometry at 280 nm and 673 nm, and assuming an absorbance of 1.40 at this wavelength for a 1 mg/ml solution of antibody and a molar extinction coefficient of 133,000 $M^{-1}$ $cm^{-1}$ at 673 nm for Cy5.5. (Maleimide-Activated Dye-Labelled Antibody B2)

Initial Preparation of p97

18. In parallel with steps 1-17, approximately 70 mg of p97 (BioAsis) was buffer-exchanged into 0.1 M potassium phosphate buffer pH 7.5 on three PD10 columns, yielding 11.2 ml of a p97 solution at 6.37 mg/ml as indicated by UV-visible spectrophotometry at 280 nm, and assuming an absorbance of 1.19 at this wavelength for a 1 mg/ml solution of p97.

Thiolation of p97

19. To 54 mg (8.48 ml) of the buffer-exchanged p97 was added 0.41 mg (82 ul) of a 5.0 mg/ml solution of S-acetylthioacetic acid, succinimidyl ester (SATA, Thermo 26102) in DMSO, equivalent to a SATA:p97 ratio of 3.2:1.

20. The S-acetylthiolation reaction was allowed to proceed for 55 minutes at 20° C.

21. 848 ul of an aqueous solution of 0.05M EDTA disodium salt and 2.5M hydroxylamine hydrochloride, pH 7.0, was added to deprotect the thiols, the deprotection reaction being allowed to proceed for 17 minutes at 20° C.

22. The crude thiolated p97 was purified using size exclusion chromatography on five PD10 columns to remove low-molecular weight by-products, using 50 mM potassium phosphate, 150 mM sodium chloride, 5 mM EDTA buffer pH 7.0 buffer as eluent. This yielded a solution of thiolated p97 with a p97 concentration of 3.65 mg/ml as indicated by UV-visible spectrophotometry at 280 nm, and assuming ah absorbance of 1.19 at this wavelength for a 1 mg/ml solution of p97. A sample was assayed for thiol content using Ellman's Reagent, indicating an incorporation of 0.9 thiol groups per p97 molecule. (Thiolated p97 C1)

23. To 8 mg (1.26 ml) of the buffer-exchanged p97 Was added 0.29 mg (57 ul) of a 5.0 mg/ml solution of S-acetylthioacetic acid, succinimidyl ester (SATA, Thermo 26102) in DMSO, equivalent to a SATA:p97 ratio of 15:1.

24. The S-acetylthiolation reaction was allowed to proceed for 55 minutes at 20° C.

25. 126 ul of an aqueous solution of 0.05M EDTA disodium salt and 2.5M hydroxylamine hydrochloride, pH 7.0, was added to deprotect the thiols, the deprotection reaction being allowed to proceed for 17 minutes at 20° C.

26. The crude thiolated p97 was purified using size exclusion chromatography on a single PD10 column to remove low-molecular weight by-products, using 50 mM potassium phosphate, 150 mM sodium chloride, 5 mM EDTA buffer pH 7.0 buffer as eluent. This yielded a solution of thiolated p97 with a p97 concentration of 2.83 mg/ml as indicated by UV-visible spectrophotometry at 280 nm, and assuming an absorbance of 1.19 at this wavelength for a 1 mg/ml solution of p97. A sample was assayed for thiol content using Ellman's Reagent, indicating an incorporation of 3.8 thiol groups per p97 molecule. (Thiolated p97 C2)

p97-Antibody Conjugations 27. (BOA2/1) 5.0 mg (1.50 ml) of Maleimide-Activated Unlabelled Antibody A1 and 12.93 mg (3.55 ml) of Thiolated p97 C1, equivalent to a p97:antibody ratio of 4.0:1, were allowed to react together for 18 hours at 20° C.

28. (BOA2/2) 5.0 mg (1.12 ml) of Maleimide-Activated Dye-Labelled Antibody B1 and 12.93 mg (3.55 ml) of Thiolated p97 C1, equivalent to a p97:antibody ratio of 4.0:1, were allowed to react together for 18 hours at 20° C.

29. (BOA2/3) 2.5 mg (1.06 ml) of Maleimide-Activated Unlabelled Antibody A2 and 12.93 mg (3.55 ml) of Thiolated p97 C1, equivalent to a p97:antibody ratio of 8.0:1, were allowed to react together for 18 hours at 20° C.

30. (BOA2/4) 2.5 mg (1.35 ml) of Maleimide-Activated Dye-Labelled Antibody 82 and 12.93 mg (3.55 ml) of Thiolated p97 C1, equivalent to a p97:antibody ratio of 8.0:1, were allowed to react together for 18 hours at 20° C.

31. (BOA2/5) 23.0 mg (6.89 ml) of Maleimide-Activated Unlabelled Antibody A1 and 2.47 mg (0.87 ml) of Thiolated p97 C2, equivalent to a p97:antibody ratio of 1:6.0, were allowed to react together for 18 hours at 20° C.

32. (BOA2/6) 23.0 mg (5.16 ml) of Maleimide-Activated Dye-Labelled Antibody B1 and 2.47 mg (0.87 ml) of Thiolated p97 C2, equivalent to a p97:antibody ratio of 1:6.0, were allowed to react together for 18 hours at 20° C. 33. The six crude antibody-p97 and antibody-Cy5.5-p97 conjugates from steps 27-32 were concentrated to 1-1.5 ml using Vivaspin 6 (30 kDa cut-off) spin filters and purified by high-resolution size exclusion chromatography, using a 1.6×36 cm Superdex 200PG column at 2.0 ml/min with 50 mM potassium phosphate buffer+150 mM sodium chloride, pH 6.7, as the eluent.

34. This yielded conjugates with approximate p97:antibody ratios shown below, as indicated by UV-spectrophotometric and size-exclusion chromatography data.

TABLE 2

| Conjugate | P97:antibody ratio |
|---|---|
| (BOA2/1) | 1.3:1 |
| (BOA2/2) | 1.5:1 |
| (BOA2/3) | 3:1 |
| (BOA2/4) | 3:1 |
| (BOA2/5) | 1:2.5 |
| (BOA2/6) | 1:2.5 |

Example 2 p97-Her2/Neu Antibody Conjugates Enhance Cell Death of Breast Cancer Cells

This example demonstrates that p97-Her2/neu antibody conjugates of the invention have enhanced activity against breast cancer cells compared with anti-Her2/neu antibodies that are not conjugated with p97.

The compounds noted below were tested against the breast cancer cell lines MCF-7 vector, MCF-7/Her2, BT474, and SKBr3, as further described below. Vehicle was PBS, pH 6.7.

TABLE 3

| Compound # | Molecular Weight (g/mol) |
|---|---|
| Trastuzumab | 145,531.50 |
| BOA2/1 | 250,000.00 |
| BOA2/3 | 760,000.00 |
| BOA2/5 | 530,000.00 |
| hMTF (p97) | 76,000.00 |

Materials & Methods

Cell Lines

The MCF-7 vector (human breast cancer) cell line was maintained under the following conditions: RPMI 1640 media, 2 mM L-glutamine, 10% FBS, 500 µg/mL G418. The MCF-7 HER2 (human breast cancer, transfected) cell line was maintained under the following conditions: RPMI 1640 media, 2 mM L-glutamine, 10% FBS, 500 µg/mL G418. The SKBR3 (human breast cancer) cell lline was maintained under the following conditions: McCoys 5A media, 1.5 mM L-glutamine, 10% FBS. The BT474 (human breast cancer) cell line was maintained under the following conditions: DMEM media, 2 mM L-glutamine, 10% FBS Cell Growth Optimization A cell growth optimization study is performed prior to the drug screening study. The objective of the cell growth study is to determine the optimal seeding density for each cell line to ensure that 95-100% confluency is reached after 96 hour incubation (in both low and high serum conditions) and to determine the optimal staining conditions for Hoechst 33342 (H33342). The following cell densities are tested: 500, 1000, 1500, 2000 2500 and 3000 cells/well in 50 µL in normal serum conditions (Table 4) and 2000, 4000, 6000, 8000, 10000 and 12000 cells/well in 50 µL in low (1%) serum conditions (Table 5). Cells are diluted to different concentration in a 2 mL 96-well deep block based on the following tables:

TABLE 4

Normal Serum Conditions

| Number of Cells (50 µL) | Volume of cell culture media for dilution (mL) | Volume of stock cell solution (mL) (stock = 60,000 cells/mL) | Final Cell Concentration (cells/mL) |
|---|---|---|---|
| 3,000 | 0.000 | 2.000 | 60000 |
| 2,500 | 0.333 | 1.667 | 50000 |
| 2,000 | 0.667 | 1.333 | 40000 |
| 1,500 | 1.000 | 1.000 | 30000 |
| 1,000 | 1.333 | 0.667 | 20000 |
| 500 | 1.667 | 0.333 | 10000 |

TABLE 5

Low Serum Conditions

| Number of Cells (50 µL) | Volume of cell culture media for dilution (mL) | Volume of stock cell solution (mL) (*stock = 240,000 cells/mL) | Final Cell Concentration (cells/mL) |
|---|---|---|---|
| 12,000 | 0.000 | 2.000 | 240,000 |
| 10,000 | 0.333 | 1.667 | 200,000 |
| 8,000 | 0.667 | 1.333 | 160,000 |

TABLE 5-continued

Low Serum Conditions

| Number of Cells (50 µL) | Volume of cell culture media for dilution (mL) | Volume of stock cell solution (mL) (*stock = 240,000 cells/mL) | Final Cell Concentration (cells/mL) |
|---|---|---|---|
| 6000 | 1.000 | 1.000 | 120,000 |
| 4,000 | 1.333 | 0.667 | 80,000 |
| 2,000 | 1.667 | 0.333 | 40,000 |

*Take 60,000/25 mL stock solution of cells and spin down and add 6.5 mL media

Plating is done with the Hydra by transferring from the 96 well deep block to 4 quadrant wells in corresponding Grenier Bio or with a multi-channel pipette. Each well of the 384-well plate has 50 µL added and this is repeated. After 24 hours, the media is aspirated and replaced with media containing normal serum or no serum. During the aspiration step, approximately 45 µL of media is removed and replaced with new media. Staining is performed daily on 1 plate which will be imaged. Images are compared over the time course for each cell line to determine optimal seeding density.

Hoechst 33342 Staining Optimization

Optimization of the Hoechst 33342 is important to give the strongest signal-to-noise ratio without precipitating the dye or killing the cells. Hoechst 33342 is a cell permeable dye which labels the cell nuclei allowing for efficient image-based segmentation and counting. Four different concentrations of Hoechst 33342 are tested (0.5, 1, 5, 10 µM) for effectiveness. EthD1 is a membrane impermeable nucleic acid dye that binds to DNA in the nucleus of cells with compromised cell membranes (i.e. dead cells). EthD1 is used at a final concentration of 1 µM. The two stains Provide a systematic way of identifying live/dead cells for efficient cell counting. Using 1 plate, Hoechst 33342 are diluted in cell culture media to the working concentrations indicated in the following table:

TABLE 6

| Final concentration H33342 (µM) | Intermediate concentration H33342 (µM) | stock dye (1 mM) | diluting media (µL) | final volume (µL) |
|---|---|---|---|---|
| 0.5 | 4 | 1.2 | 298.8 | 300 |
| 1 | 8 | 2.4 | 297.6 | 300 |
| 5 | 40 | 12 | 288.0 | 300 |
| 10 | 80 | 24 | 276.0 | 300 |

10 µL of the staining solution is added to each well and incubated for 30 minutes at 37° C., 5% $CO_2$ to allow for uptake of the dye. Image optimization is achieved on the InCell Analyzer 1000 machine.

Drug Screening Protocol:

Day 0: Cell Plating-384 Well Plates:

Cells are harvested and plated in two 384 well Grenier Bio One TC treated µClear 384 plates based on the optimal cell numbers in the cell growth optimization study. 50 µL from the stock cell solution is added to the assay plate according to the Assay Plate Layout (120 wells/cell line)

Figure 13:
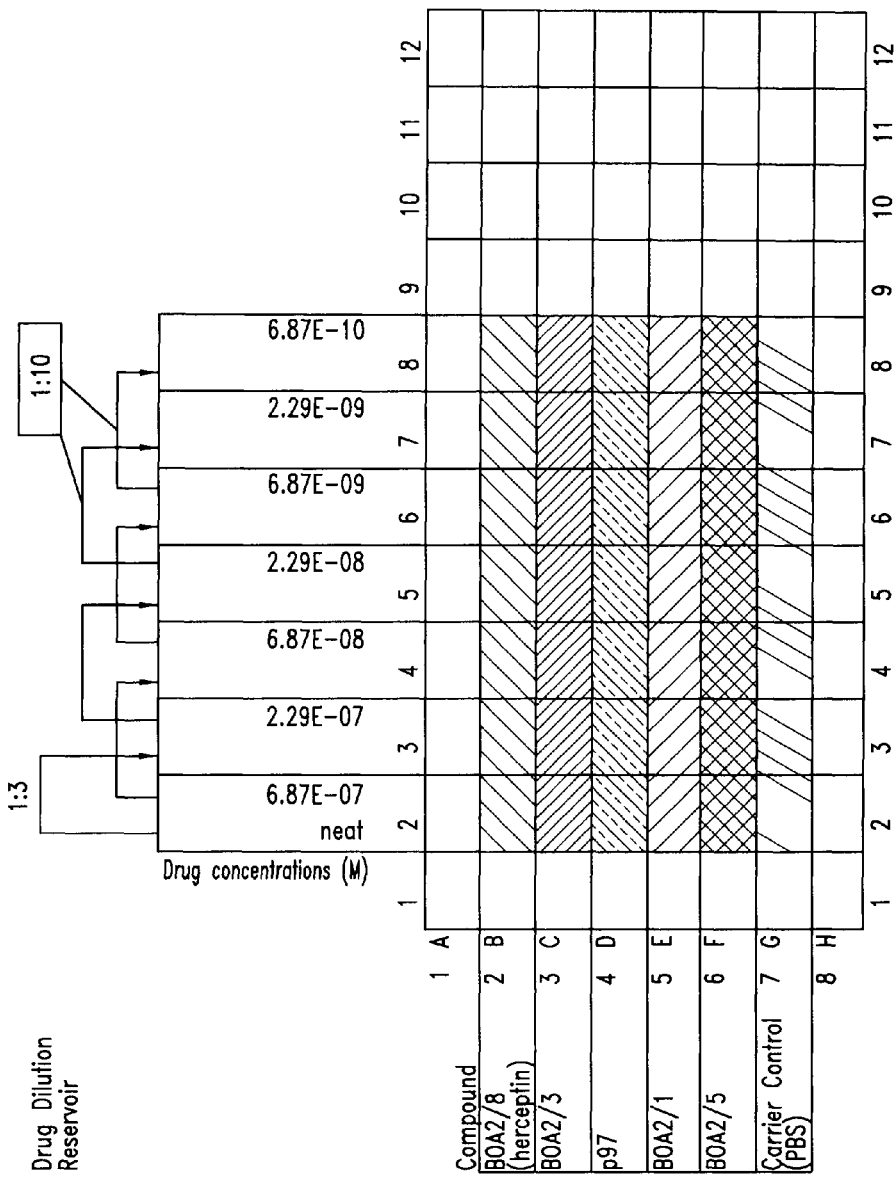
FIG. 13 is an Assay Plate Layout that shows the dilutions of Test and Control Articles (see Example 2).

Day 1: Drug Treatment:

Serial dilutions of Test Articles are performed in 96 well plates. Following dilutions of Test and Control Articles, 20 µL/well x 2 wells per drug concentration are added according to the Assay Plate Layout shown in FIG. 13.

The Table below shows illustrative dilutions of stocks to give desired working solutions.

TABLE 7

Dilutions of stocks to give a working solution. Doses based on Clin Cancer Res 2004;10:2512-2524. Published online April 8, 2004.

| Test Material | Stock Conc (moles/uL) | Stock Vol (uL) | Media (uL) | Total Vol (uL) | Final Molar Conc | Final Conc (ug/ml) |
|---|---|---|---|---|---|---|
| Herceptin | 3.96E-11 | 17 | 983 | 1000 | 6.87E-07 | 100 |
| BOA2/1 | 2.72E-12 | 253 | 747 | 1000 | 6.87E-07 | 172 |
| BOA2/3 | 1.12E-12 | 614 | 386 | 1000 | 6.87E-07 | 522 |
| BOA2/5 | 1.72E-12 | 400 | 600 | 1000 | 6.87E-07 | 364 |
| p97 | 1.32E-10 | 5 | 995 | 1000 | 6.87E-07 | 50 |

*These are dilutions to give 1 mL of material. A 1 in 10 dilution of this gives 10 µg/mL equivalent.

The dilution scheme used in the plate is that outlined above in "Exemplary Drug Dilution Reservoir."

TABLE 8

| Dilution | Final Molar Conc (M) | Final Conc (ug/ml) herceptin equivalents |
|---|---|---|
| neat | 6.87E-07 | 100 |
| 1:10 | 6.87E-08 | 10 |
| 1:100 | 6.87E-09 | 1 |
| 1:1000 | 6.87E-10 | 0.1 |
| 1:3.3 | 2.29E-07 | 30 |
| 1:33 | 2.29E-08 | 3 |
| 1:333 | 2.29E-09 | 0.3 |

Day 2-3: Incubation:

Cells are incubated with drug for 72 hours at 37° C., $%$ $CO_2$, humidified incubator.

Day 4: Imaging:

Plates are stained with Hoechst 33342 (total cells) based on staining optimization study, and Ethidium Homodimer (dead cells) to determine viable cell counts. Plates are imaged with GE InCell 1000 Cellular Imaging and Analysis System.

Results

Using procedures substantially as described above, various conjugates of the invention were tested for activity against breast cancer cell lines in comparison with an unconjugated anti-Her2/neu antibody. Results of cell viability assays are summarized in FIGS. 1-4. Surprisingly, in some HER2+ breast cancer cell lines, p97-antibody conjugates demonstrated a significant improvement in cancer killing activity compared to trastuzumab alone. For example, for the BT474 cell line (FIG. 1), conjugates BOA2/1 and BOA2/5 showed a profound effect on cell death at 229 nM. The effect of these conjugates on cell viability was much more pronounced than the effect observed for cells treated with trastuzumab-alone (BOA2/8).

In addition, the results of other experiments confirmed that trastuzumab does not enter human brain endothelial (HBE) cells in culture nor does it cross the intact blood brain barrier in animals. However, p97-antibody conjugates showed a marked transport into HBE cells, suggesting that the conjugates have the potential to cross the blood-brain barrier and enter brain tissue.

In light of these findings, it is clear that the conjugates of the present invention can improve the therapeutic potential of anti-Her2/neu antibodies by improving the activity of the antibodies and/or allowing the antibodies to access Her2/neu-expressing metastatic cancer cells in the CNS.

Example 3

Distribution of p97-Trastuzumab Conjugates in Brain Tissue

Experiments were performed to evaluate distribution of p97-trastuzumab (Herceptin®) conjugates in brain tissue compartments. First, the following rhodamine-labeled proteins were injected intravenously into mice about 23 grams in size: 100 μg p97-rhodamine at about 4.35 mg/kg; 195 μg p97-rhodamine at about 8.47 mg/kg; 375 μg p97-BTA-rhodamine at about 16.3 mg/kg; and rhodamine alone.

For labeled proteins, three 20 μm sections and three 50 μm sections were collected at 2 hours post-IV injection, and two 20 μm sections and two 50 μm sections were collected at 24 hours post-IV injection. For rhodamine alone, four 20 μm sections and two 50 μm sections were collected at 2 hours post-IV injection. These sections were sent to iCapture Imaging Facility for confocal analysis.

The number of voxels were measured in the 20 micron sections of the vascular compartment (capillaries) and the brain parenchyma (all tissue except the vascular compartment). A voxel is a three dimensional pixel taken from confocal imaging of a tissue section. The number of fluorescent voxels in the brain parenchyma was divided by the total number of voxels to give the volume fraction of a given conjugate in the parenchyma. The number of fluorescent voxels in the brain capillaries was divided by the total number of voxels to give the volume fraction of a conjugate in the vasculature (capillaries).

Figure 5B:
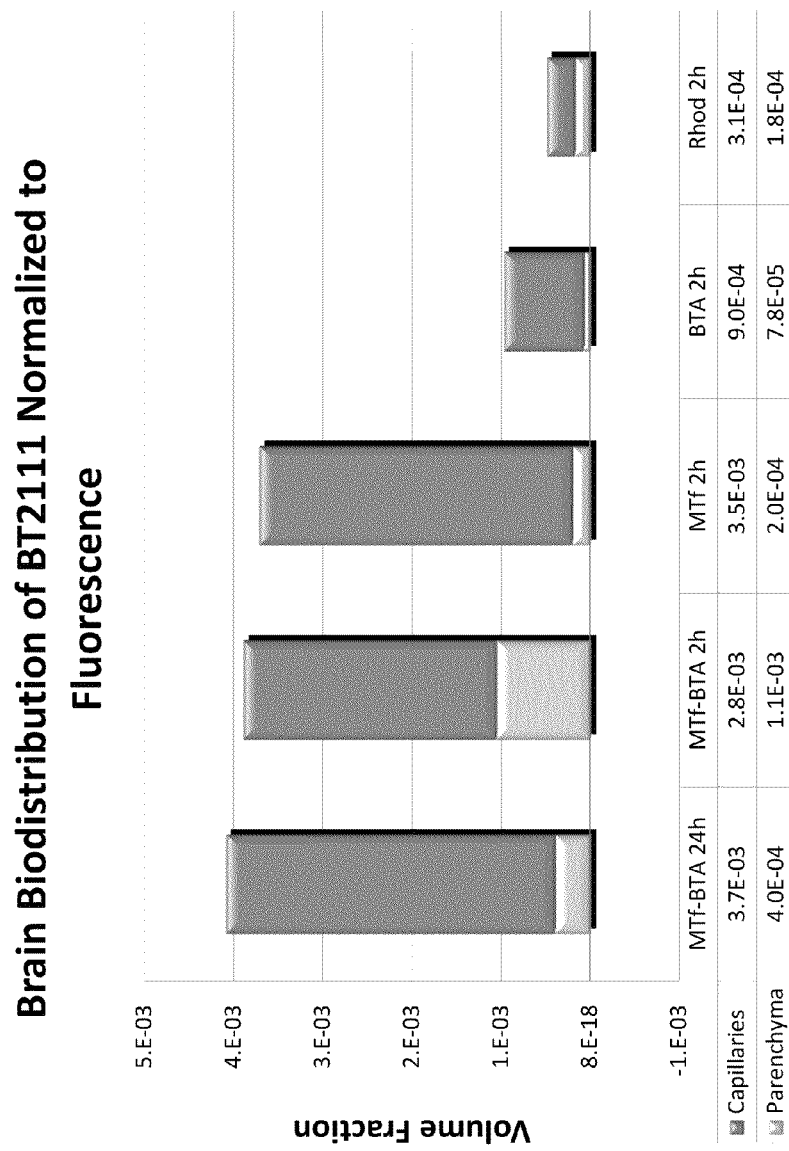
Figure 5C:
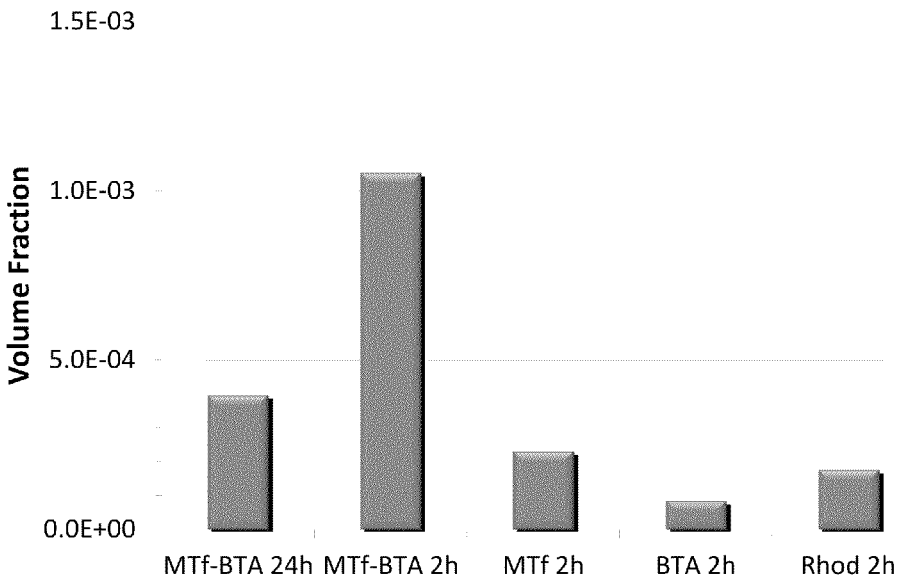
Figure 5D:
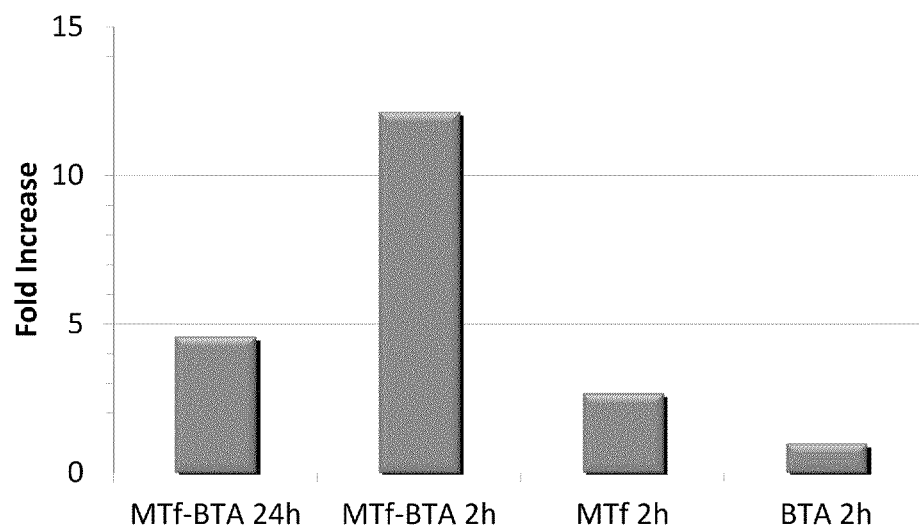

The results are shown in FIGS. 5A-5D. In these figures "MTf" is p97 and "BTA" is trastuzumab. FIG. 5A shows the distribution of p97-trastuzumab (BT2111; MTf-BTA) in brain tissue when normalized to injected dose, and FIG. 5B shows the same when normalized to fluorescence. Here, most of the fluorescent proteins are found in the capillaries, but relative to p97 alone or trastuzumab alone, the p97-trastuzumab conjugate selectively distributes to the parenchyma, especially at the 2 hour time-point. This result is further illustrated in FIG. 5C, which shows significantly increased fluorescence localized to the brain parenchyma for p97-trastuzumab conjugate, and FIG. 5D, which shows that the parenchymal levels of the p97-trastuzumab conjugate are 12-fold greater than trastuzumab alone and 4-fold greater than p97 alone.

These findings suggest that the combination of p97 and trastuzumab as a protein conjugate synergistically increases delivery to parenchymal brain tissues across the blood brain barrier, relative to the delivery of each protein alone.

Example 4

Distribution of p97-Trastuzumab Conjugates in Brain Metastases

Experiments were performed to evaluate the distribution of $^{25}$I-labeled p97-trastuzumab conjugate in normal brain tissue and brain metastases, relative to trastuzumab alone. The relative distribution in systemic tissues was also examined.

Intravenous drug administration of radio-labeled p97, trastuzumab, and p97-trastuzumab was performed on mice having experimental brain metastases of breast cancer. Specifically, these tumor experiments utilized immune compromised NuNu mice (Charles River Labs) that were implanted via intracardiac injection with, eGFP-expressing MDA-MB-231 BR High Her-2 human breast cancer cells. The tumor cells were allowed to implant in the brain and form brain metastases over a period of about 3-6 weeks.

Test drugs were administered once the animals start exhibiting symptoms of tumor growth. Monitoring for tissue distribution then was performed by radioactive, fluorescent, and quantitative autoradiography analysis. These experiments were performed using $^{125}$I-labeled p97, trastuzumab, and p97-trastuzumab proteins at a purity of >99%, as measured by HPLC.

Uptake of radio-labeled proteins was examined at two, eight, and 24 hour time points. Texas red-dextran was also administered (i.v.) at about 10 min-2 hr prior to euthanasia to measure blood-tumor barrier passive permeability. Brains were perfused with 2.7% albumin and iodocyanine green for about 30-60 seconds after euthanasia to map the distribution of blood vessels within the brain and brain metastases, and to remove intravascular labeled protein. Brains were snap-frozen immediately poet-perfusion washout and were cut into 20 μm coronal sections using a cryostat. The sections were analyzed for green, red, and near infrared fluorescence, to respectively map brain distribution of tumor cells, quantitate blood-tumor barrier permeability, and localize vasculature within tumors. In matching tissue sections, the distribution of $^{125}$I-protein in brain was measured by phosphorescence imaging along with radioactive standards. After analysis, tissue sections were stained to confirm tumor cell distribution. Dissection was also performed to measure and compare the level/distribution of $^{125}$I-protein (dpm/g) in other tissues, including the liver, kidneys, lung, heart, spleen, muscle, and fat.

Image analysis was used to determine the level of $^{125}$I-labeled protein in selected brain metastases and surrounding normal brain, and to obtain autoradiographic images expressed in units of nCi/g tissue or ng protein/g tissue. The uptake of labeled proteins in brain metastasis was analyzed in relation to metastasis size, blood-tumor barrier permeability, and time of circulation. Calculations were also performed to measure the percentage dose/g or ml of intact drug to brain, brain metastasis, blood and other tissues.

Figures 6A, 6B, 6C:
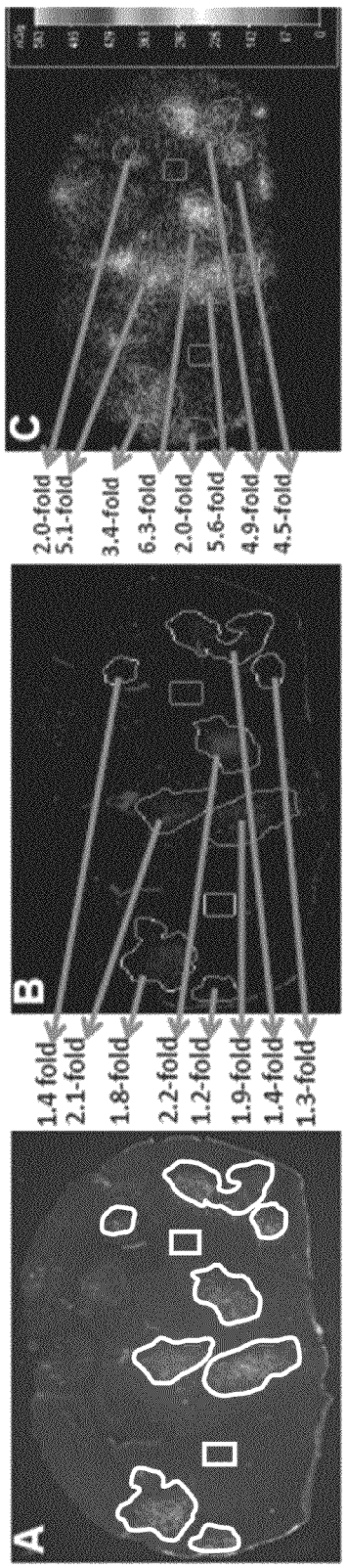
FIGS. 6A-6F show the distribution of $^{125}$I-labeled trastuzumab in the mouse brain at 24 hours post-intravenous administration.
Figure 6D:
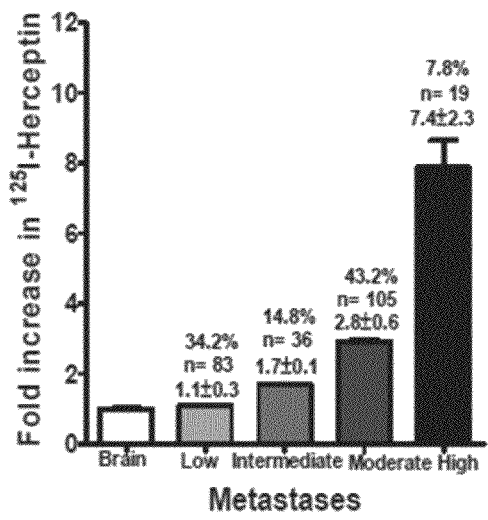
Figure 6E:
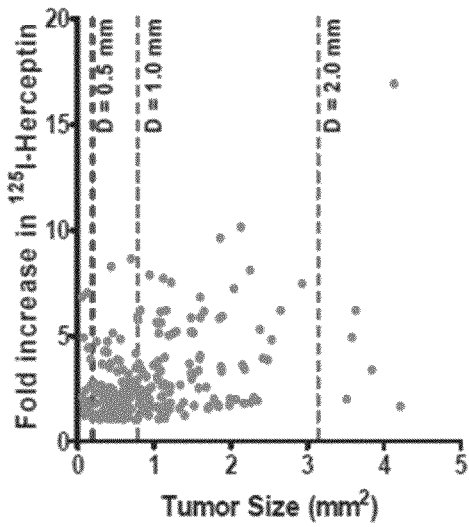
Figure 6F:
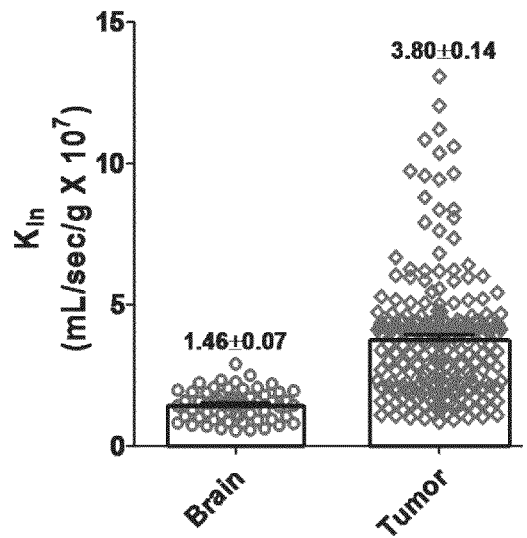
Figure 7D:
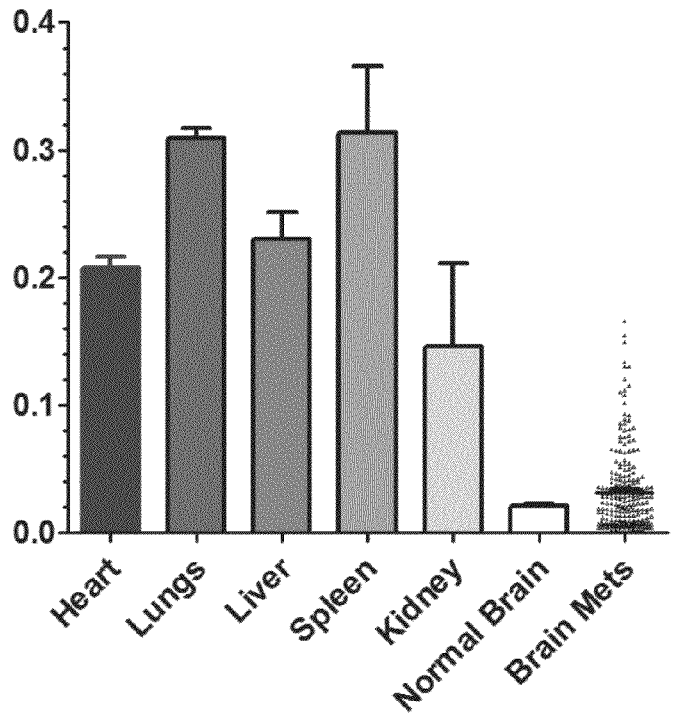
Figure 7E:
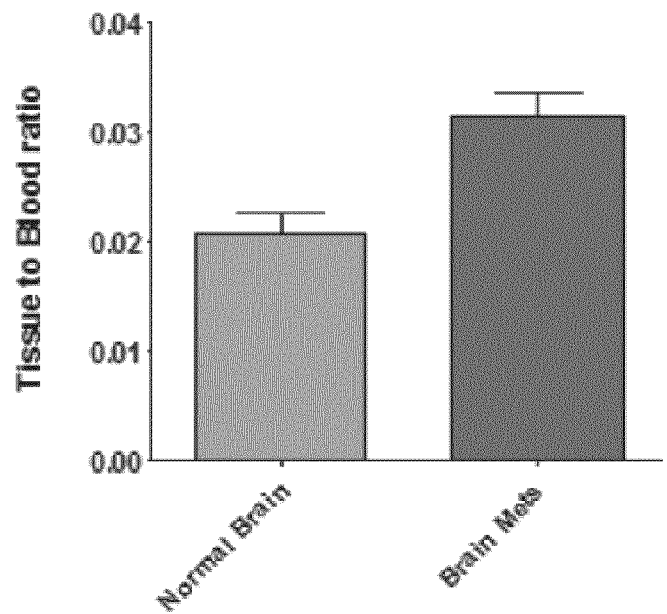

The results are shown in FIGS. 6-10. FIGS. 6 and 7 show the results for $^{125}$I-labeled trastuzumab, and FIGS. 8-10 show the results for $^{125}$I-labeled p97-trastuzumab conjugate.

FIGS. 6A-6F show the distribution of $^{125}$I-labeled trastuzumab in the mouse brain at 24 hours post-intravenous administration. FIG. 6A shows brain metastases of heterogenous size within the regions outlined in red, and FIG. 6B shows Texas Red-Dextran staining of the metastases. FIG. 6C shows an autoradiogram of $^{125}$I-labeled trastuzumab, and indicates the fold increase in antibody relative to the surrounding normal brain tissue. Here, the $^{125}$I-labeled trastuzumab is at the limit of detection. As shown in FIG. 6F, the $K_{in}$ values for trastuzumab alone are about $1.46 \times 10^{-7}$ mL/sec/g in normal brain tissue and about $3.8 \times 10^{-7}$ mL/sec/g in brain metastases, relatively low $K_{in}$ values for a protein and about ~1000 lower than the $K_{in}$ values for p97-trastuzumab conjugate.

FIGS. 7A-7D show the distribution of $^{125}$I-labeled trastuzumab in the mouse brain and other tissues at 24 hours post-intravenous administration. FIG. 7A shows brain metastases of heterogenous size within the regions outlined in red, and FIG. 7B shows Texas Red-Dextran staining of the metastases. FIG. 7C shows the autoradiogram of $^{125}$I-labeled trastuzumab, and indicates the fold increase in antibody relative to the surrounding normal brain tissue. FIG. 7D shows the tissue to blood ratio of $^{125}$I-labeled trastuzumab in various tissues. Here, trastuzumab is distributed in organs with a ratio tissue to blood of about 0.2 to 0.3 for lungs and spleen, and distribution in the heart is fairly high relative to the liver. The distribution in normal brain tissue and brain metastases is comparatively low (see the inset in FIG. 7D). The ratio of 0.02 for brain/blood is very low and only marginally superior to that found in the vascular space (i.e., the amount of trastuzumab found in the brain vasculature, which is between about 0.01 and 0.02). Very little uptake is observed in brain metastases even though these metastases demonstrate significant leakiness (see FIG. 7B).

Figures 8A, 8B, 8C:
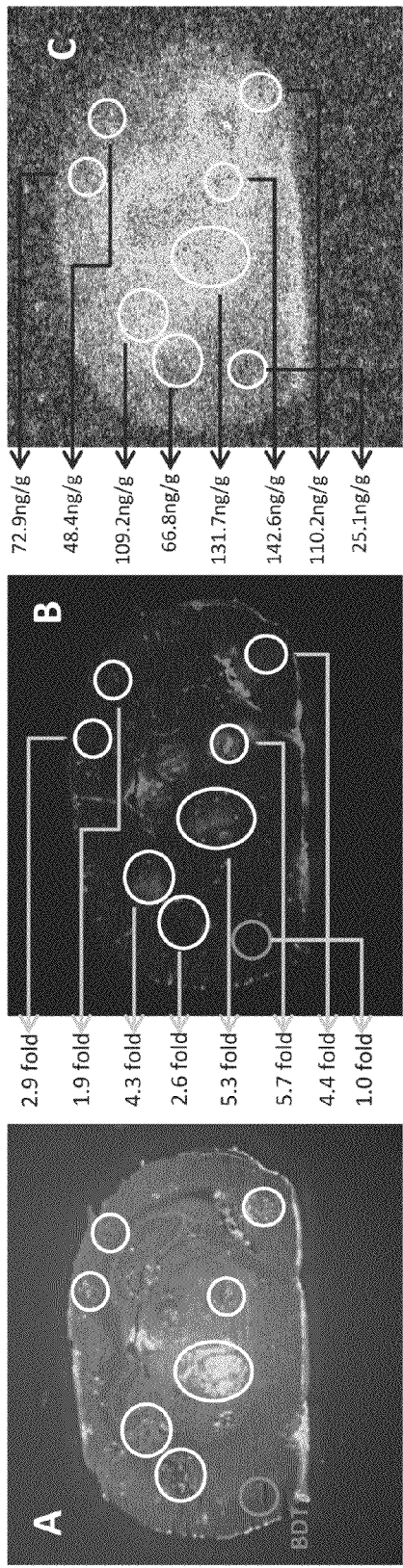
FIGS. 8A-8F show the distribution of $^{125}$I-labeled p97-trastuzumab in the mouse brain and other tissues at two hours post-intravenous administration.
Figure 8D:
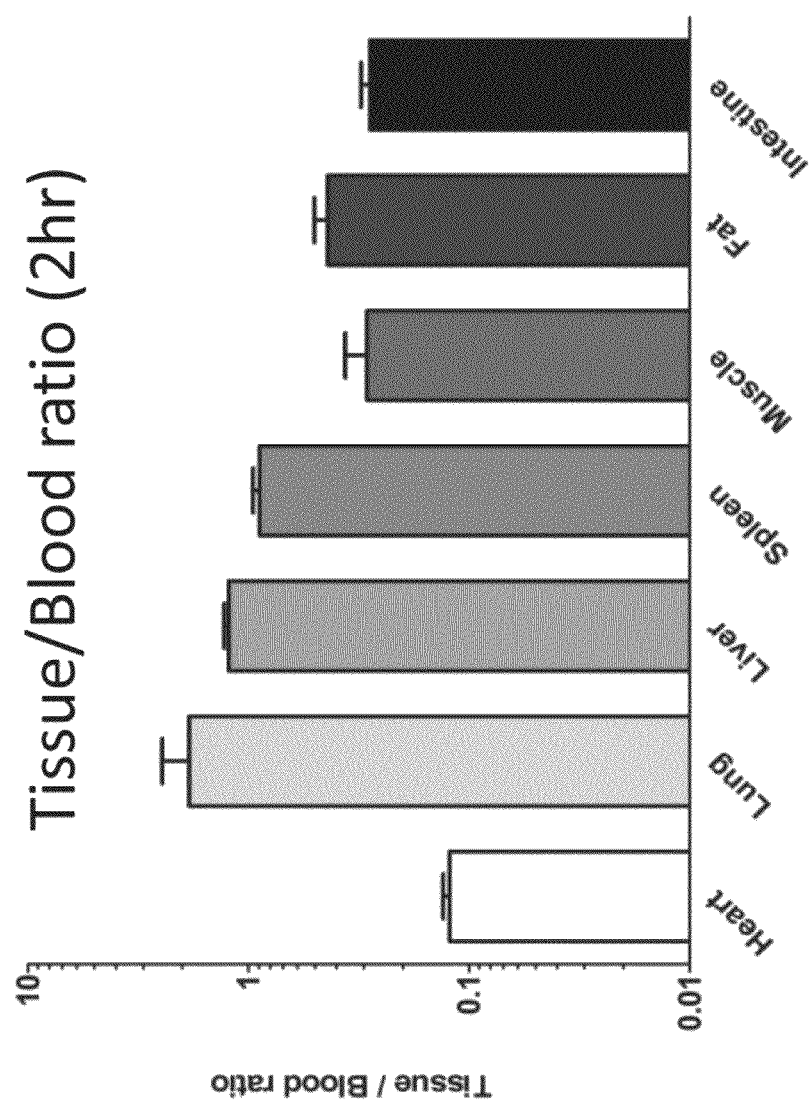
Figure 8E:
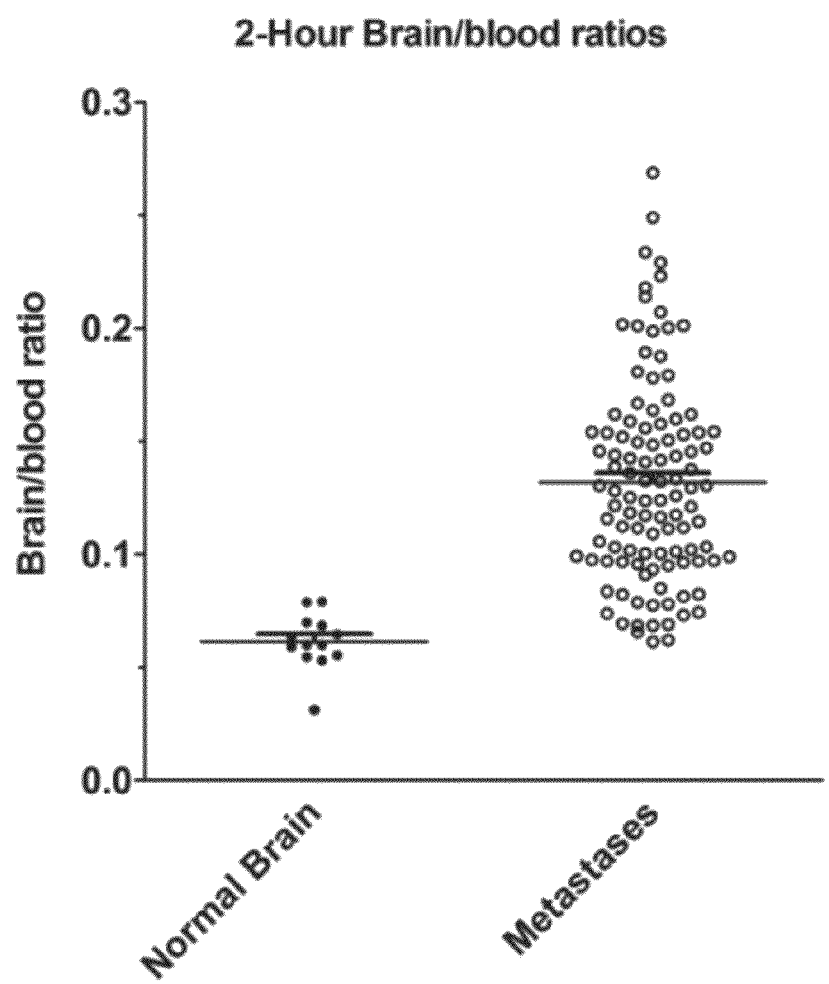
Figure 8F:
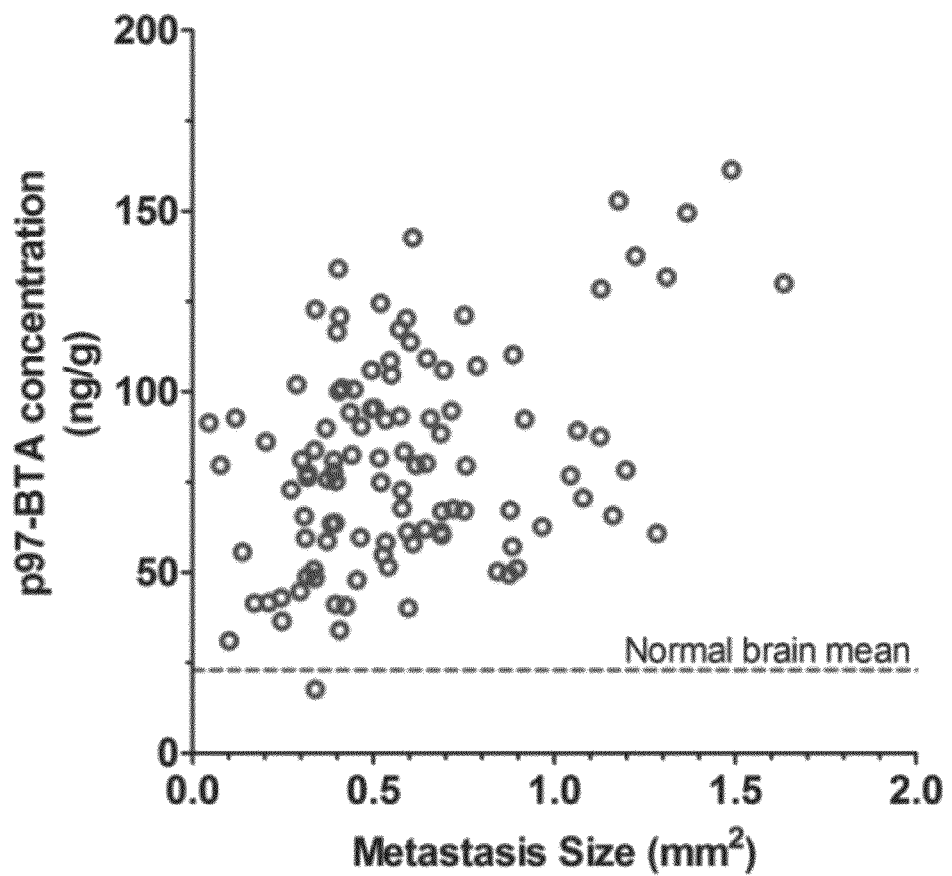

FIGS. 8A-8F show the distribution of $^{125}$I-labeled p97-trastuzumab in the mouse brain and other tissues at two hours post-intravenous administration. FIG. 8A shows brain metastases of heterogenous size within the regions outlined in red, and FIG. 8B shows Texas Red-Dextran staining of the metastases. FIG. 8C shows an autoradiogram of $^{125}$I-labeled p97-trastuzumab conjugates, and the left of FIG. 8C indicates the amount (ng/g) of conjugate found in each metastases. The left of FIG. 8B shows the fold increase of p97-trastuzumab conjugate found in each Metastases, relative to the brain distant to tumor (BDT) region shown in FIG. 8A. FIG. 8D shows the tissue/blood ratio of p97-trastuzumab conjugate for a variety of tissues. Here, distribution to the heart is significantly less than distribution to other tissues (e.g., about 10× less than lung, liver, and spleen). FIG. 8E shows the ratio of p97-trastuzumab conjugate in normal brain/blood and brain metastases/blood. The ratio for normal brain/blood is about 0.06 (compared to 0.04 for $^{125}$I-labeled p97 alone, data not shown), and the ratio for brain metastases/blood is about 0.14 (compared to 0.06 for $^{125}$I-labeled p97 alone, data not shown). FIG. 8F summarizes the concentration of $^{125}$I-labeled p97-trastuzumab conjugate found in individual brain metastases, with concentrations ranging from about 25-175 ng/g tissue.

Figure 9D:
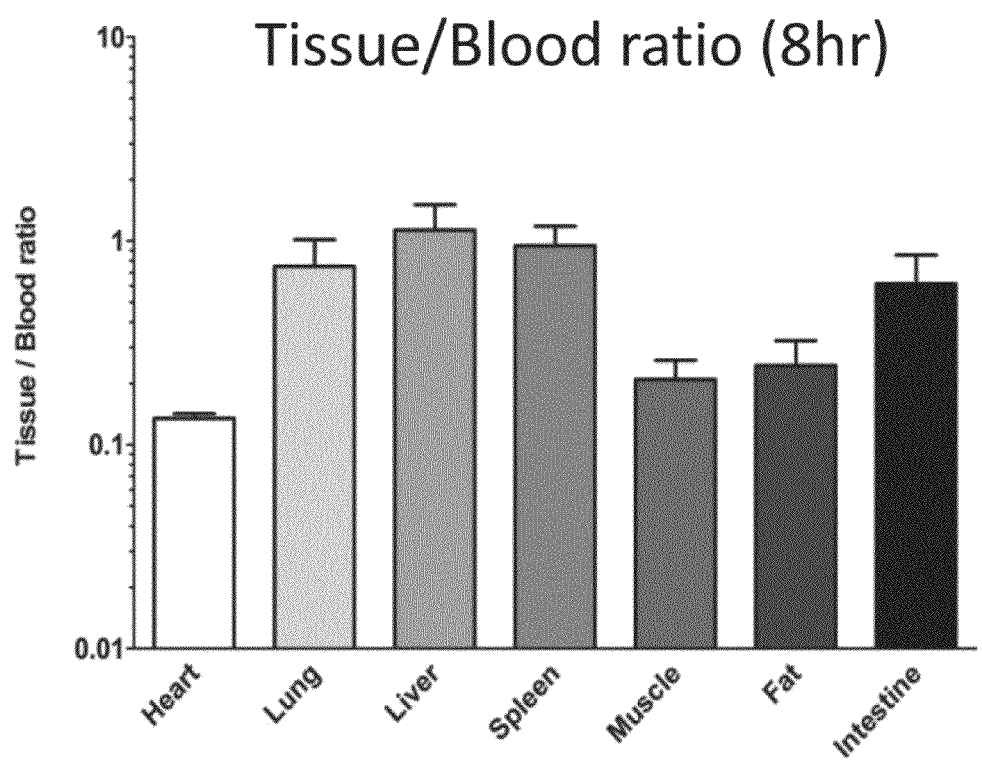
Figure 9E:
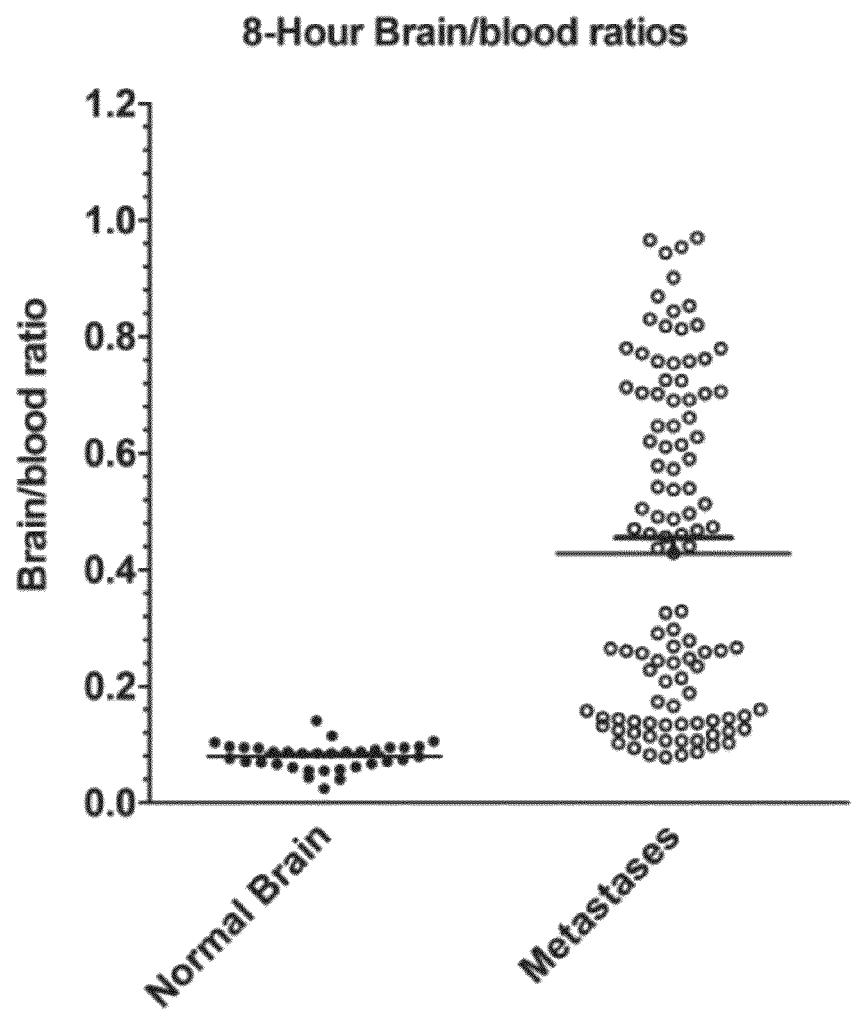
Figure 9F:
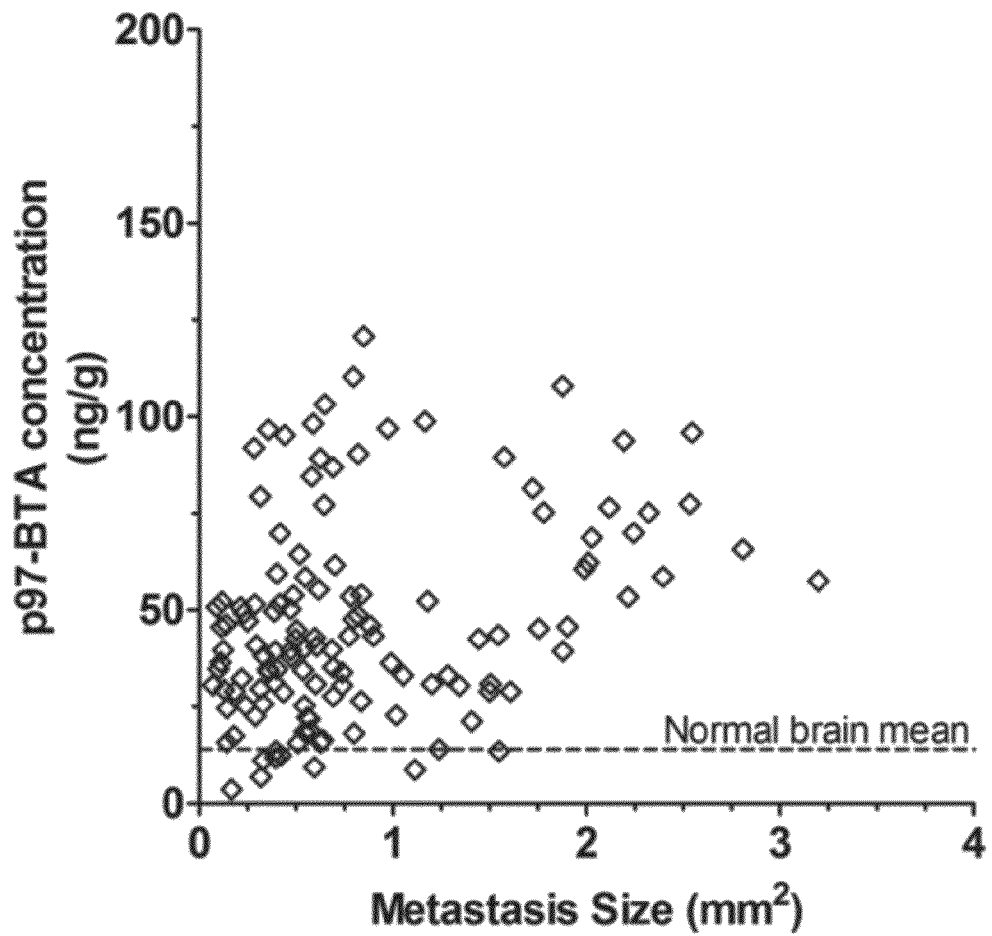

FIGS. 9A-9F show the distribution of $^{125}$I-labeled p97-trastuzumab in the mouse brain and other tissues at eight hours post-intravenous administration. FIG. 9A shows brain metastases of heterogenous size within the regions outlined in red, and FIG. 9B shows Texas Red-Dextran staining of the metastases. FIG. 9C shows an autoradiogram of $^{125}$I-labeled p97-trastuzumab conjugate, and the left of FIG. 9C indicates the amount (ng/g) of conjugate found in each metastases. The left of FIG. 9B shows the fold increase of p97-trastuzumab conjugate found in each Metastases, relative to the brain distant to tumor (BDT) regions shown in FIG. 9A. FIG. 9D shows the tissue/blood ratio of p97-trastuzumab conjugate for a variety of tissues. Here, distribution of p97-trastuzumab to the heart is significantly less than distribution to other tissues. FIG. 9E shows the ratio of p97-trastuzumab conjugate in normal brain/blood and brain metastases/blood, where the ratio in normal brain/blood is about 0.04 (compared to 0.06 for the two-hour time point, see FIG. 8E), and the ratio in brain metastases/blood is about 0.44 (compared to 0.14 for the two hour time point, see FIG. 8E). FIG. 9F summarizes the concentration of $^{125}$I-labeled p97-trastuzumab conjugate found in individual brain metastases, with concentrations ranging from about 25-125 ng/g tissue.

Figure 10A:
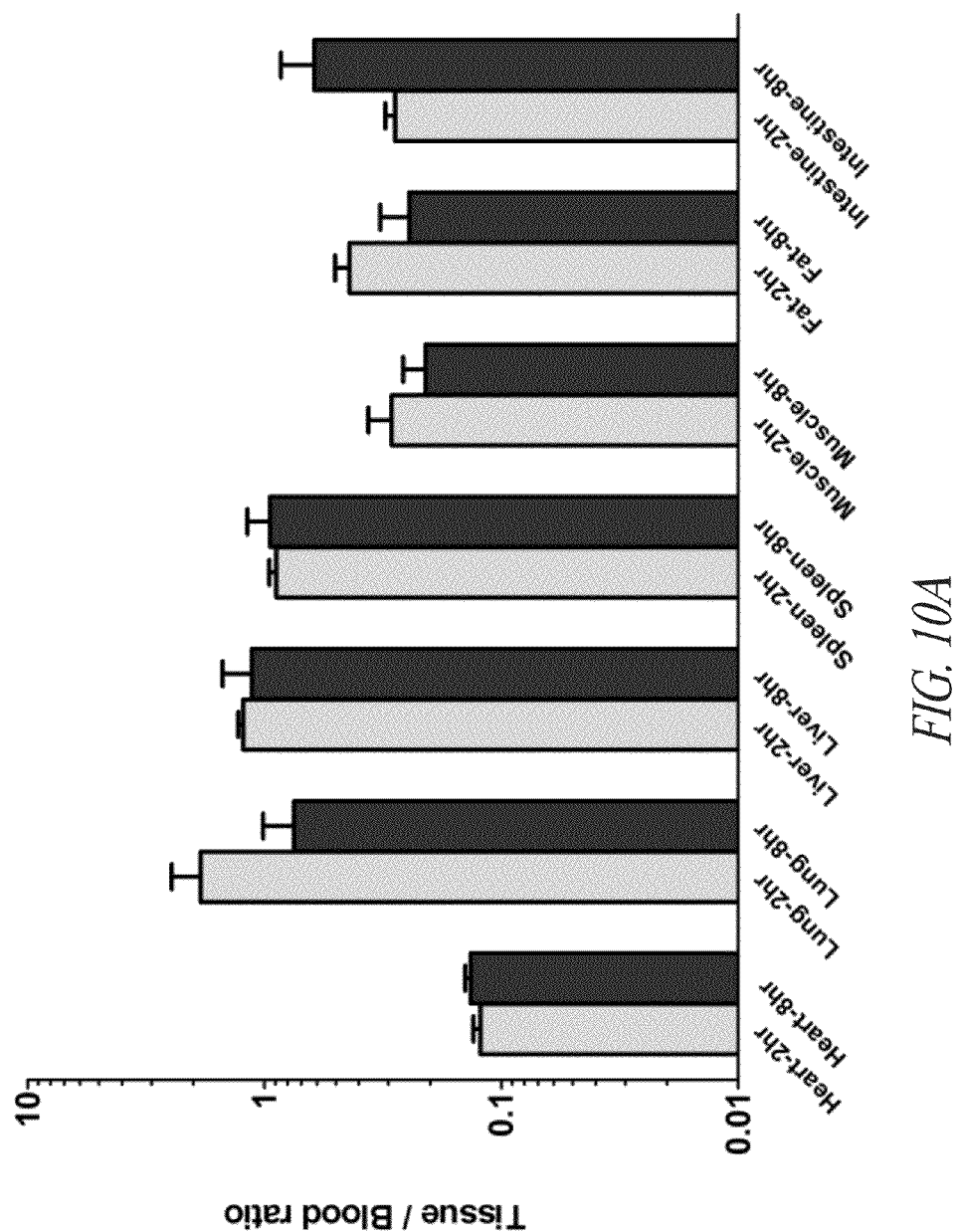
FIGS. 10A-10E summarize the data from the two and eight hour time points following intravenous administration of $^{125}$I-labeled p97-trastuzumab conjugate.
Figure 10C:
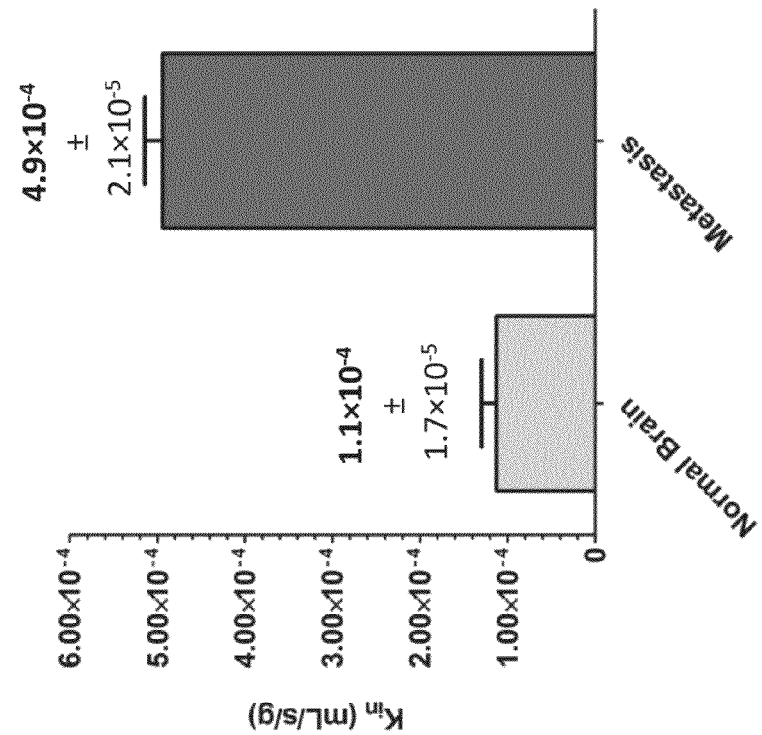
Figure 10B:
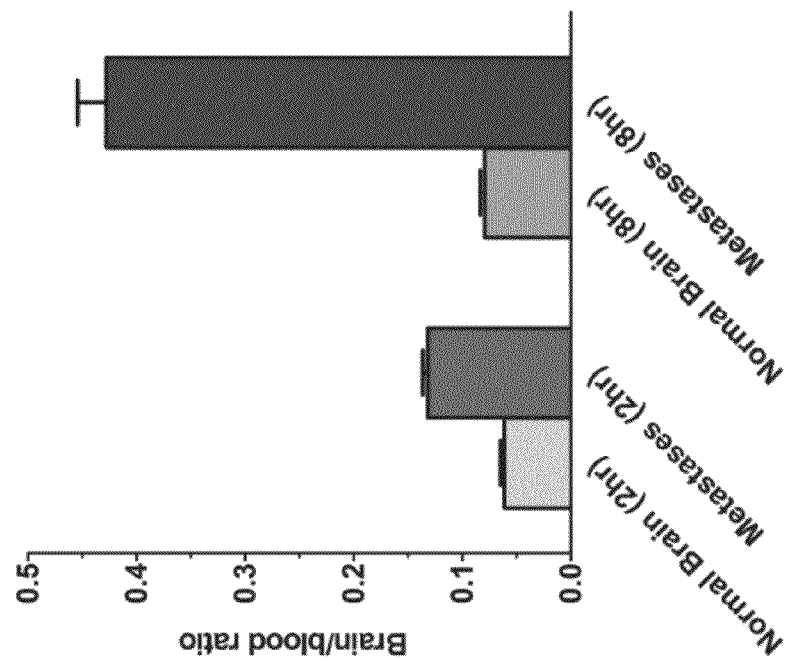
Figure 10E:
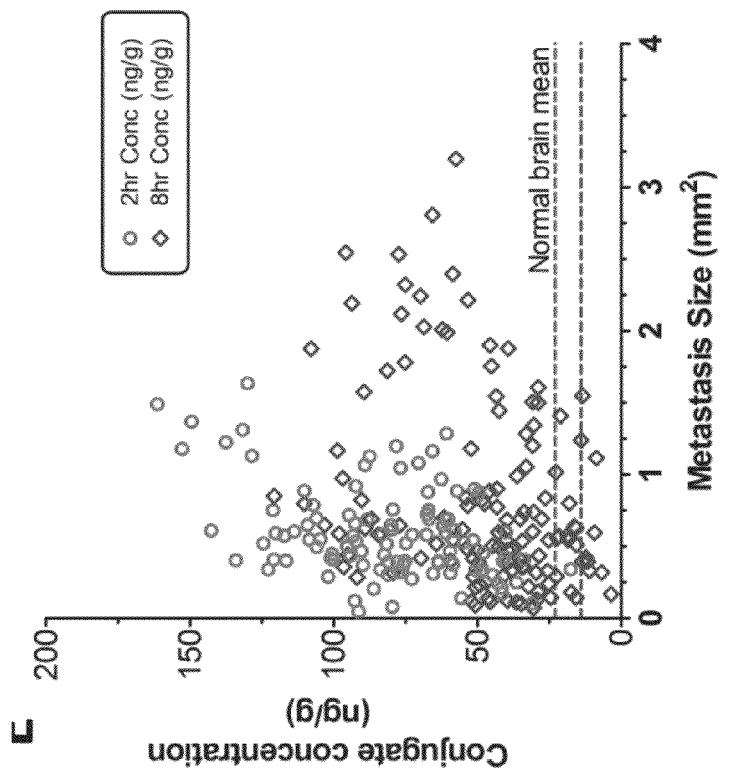
Figure 10D:
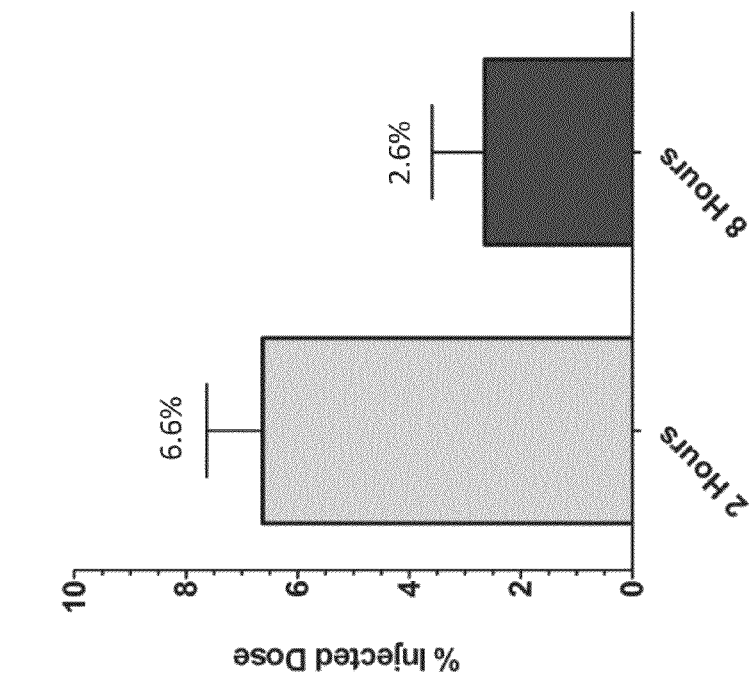

FIGS. 10A-10E summarize the data from the two and eight hour time points following intravenous administration of $^{125}$I-labeled p97-trastuzumab conjugate. FIG. 10A shows the tissue/blood ratio of p97-trastuzumab conjugate for a variety of tissues. The ratios do not vary much between the two and eight hour time points; however, the ratio (levels) of conjugate in heart tissue are significantly lower than other tissues (e.g., about 10× lower that lung and liver tissues). In contrast, the distribution of trastuzumab alone in heart tissue was similar to liver (see FIG. 7D). FIG. 10B shows that the levels of conjugate in normal brain tissue are marginally lower at the eight hour time point (relative to the two hour time point), and the levels of conjugate in brain metastases are significantly higher at the that same time point. FIG. 10C shows the measured $K_{in}$ values for the p97-trastuzumab conjugate in normal brain tissue ($1.1 \times 10^{-4}$ mL/sec/g) and brain metastases ($4.9 \times 10^{-4}$ mL/sec/g). Compared to the $K_{in}$ values for trastuzumab (see FIG. 6F), the p97-trastuzumab conjugate is transported into brain about 1000 times more rapidly than trastuzumab alone. FIG. 10D shows the percentage of injected dose in brain tissue at 2 and 8 hours, and FIG. 10E summarizes the concentration of $^{125}$I-labeled p97-trastuzumab conjugate in individual brain metastases at two and eight hours post-administration.

The pharmacokinetic profile of p97-trastuzumab conjugates was also calculated based on the data from the two and eight hour time points. These data are shown in Table 9 below.

TABLE 9

| Parameter | Value | Unit |
|---|---|---|
| $K_e$ | 0.297 | $hr^{-1}$ |
| $V_d$ | 10.76 | mL |
| $t_{1/2}$ | 2.32 | hr |
| Cl | 3.202 | mL/hr |
| $AUC_{0-\infty}$ | 2.523 | µCi × hr/mL |
| Dose | 8.08 | µCi/mL |
| F | 1 | [Unit-less] |

Overall, these data strongly suggest that therapeutically effective concentrations of p97-trastuzumab conjugate can be achieved in brain tissue metastases, even by systemic (e.g., intravenous) administration of such conjugates. These data also suggest that p97 and trastuzumab work synergistically together to selectively target p97-trastuzumab conjugates to brain metastases relative to normal brain tissue, and at a significantly greater rate (1000 fold) than trastuzumab alone. Conjugation to p97 thus not only increases transport of trastuzumab across the blood-brain barrier, but also the blood-tumor barrier. Further, because of the reduced distribution to heart tissues relative to other tissues, these data suggest that conjugation to p97 might reduce the cardiotoxic effects of antibodies such as trastuzumab.

Example 5

Production of p97-Cetixumab Conjugates and Assays for In Vitro Cytotoxicity

In vitro anticancer efficacy assays are performed in two human cancer cell lines, A-431 and HT-29, to evaluate the relative efficacies as the $IC_{50}$ of cetuximab and p97-cetuximab conjugates, relative to p97 alone and phosphate buffer saline (PBS) as vehicle controls. The A-431 cell line is a EGFR-expressing human epidermoid carcinoma and the HT-29 cell line is a human colorectal adenocarcinomas.

Figure 11A:
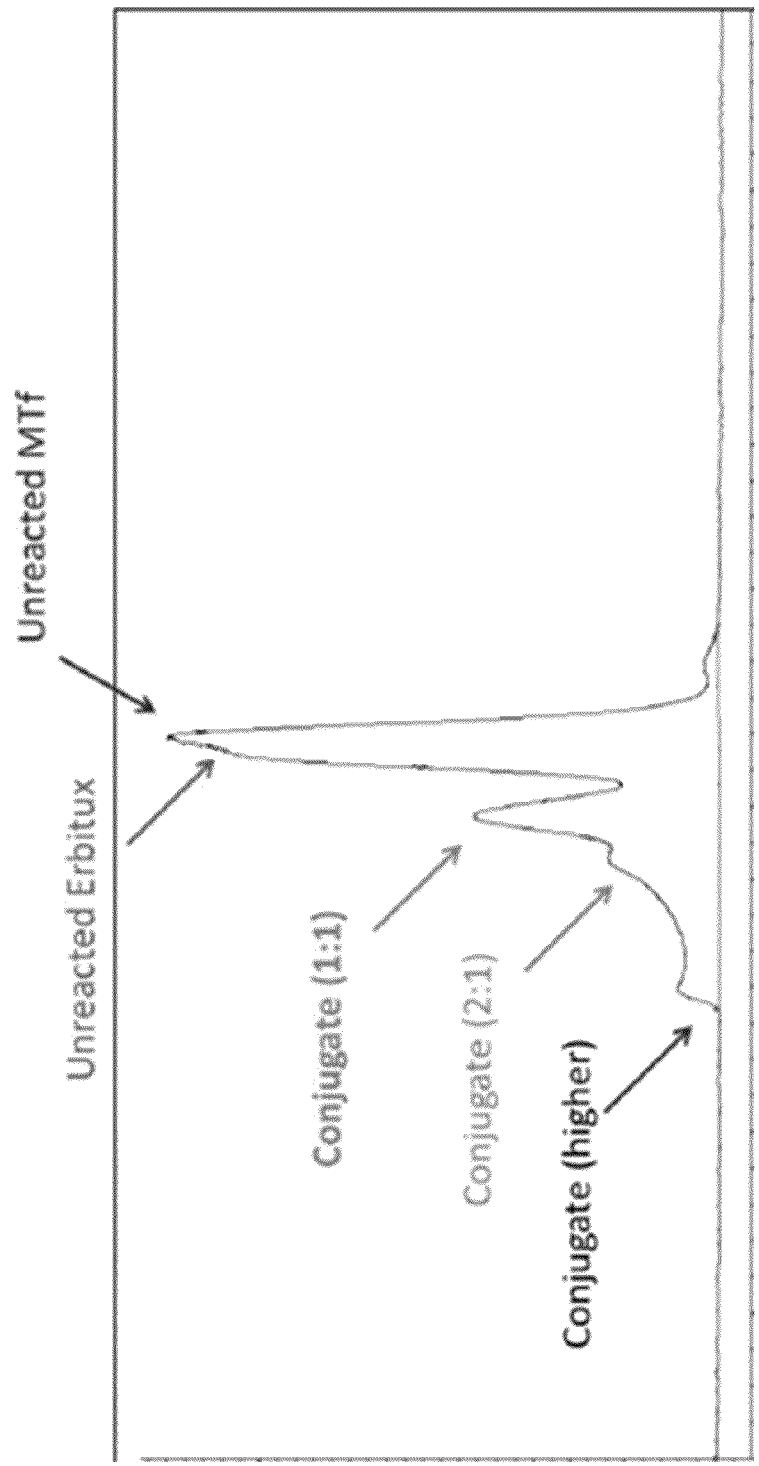
FIGS. 11A and 11B show HPLC analysis of p97-cetuximab conjugates.

As noted above, p97 (melanotransferrin) is a monomeric sialoglycoprotein belonging of the iron binding family of proteins that include transferrin, lactoferrin, and ovatransferrin. It was identified originally as a 97 kD, GPI linked, membrane bound protein on the surface of melanoma cells and was designated as melanoma-associated antigen p97. A soluble form (82 kD) missing the GPI anchor has been produced using recombinant techniques. Cetuximab (Erbitux®) is a human $IgG_1$ monoclonal antibody drug approved for use to treat certain human cancers by acting on the extracellular domain of EGFR and its mechanism of action is related to blocking EGFR activation by interfering with ligand binding.

p97-cetuximab conjugates were prepared by covalently linking soluble p97 to cetuximab via a thioether linker. FIG. 11A shows an HPLC profile of the crude reaction mixture after 24 hours at room temperature.

Figure 11B:
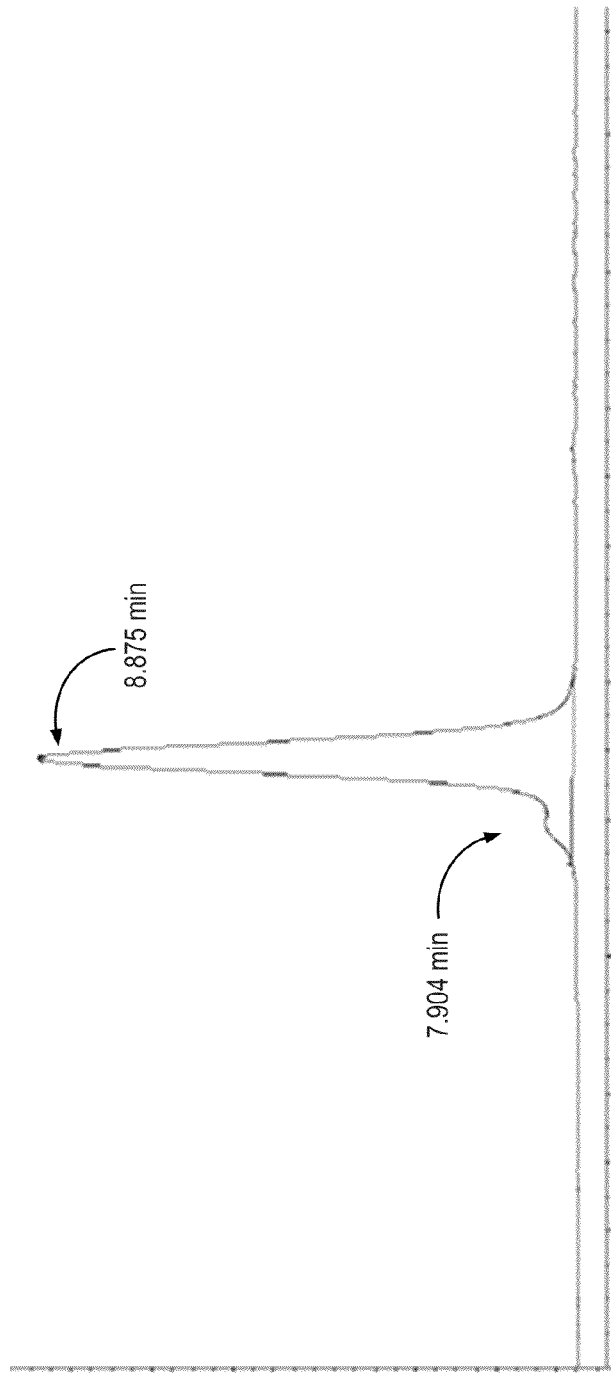

The reaction product was then analyzed by size exclusion HPLC to determine concentration and by SDS-PAGE to determine molecular weight. An aliquot of the concentrated, sterilized p97-cetixumab conjugate was diluted 10 times with 1×PBS, and an aliquot was injected into the HPLC size exclusion column. As shown in FIG. 11B, the elution profile showed a major peak (96%) with a Rt of 8.875 minutes, earlier than that of cetuximab (9.70 min) or p97 (10.03 min). The area of the peak at 220 nm (1856.9) was used together with p97 and cetuximab standard curves to determine the concentration of the product at 4.0 mg/ml.

Figure 12:
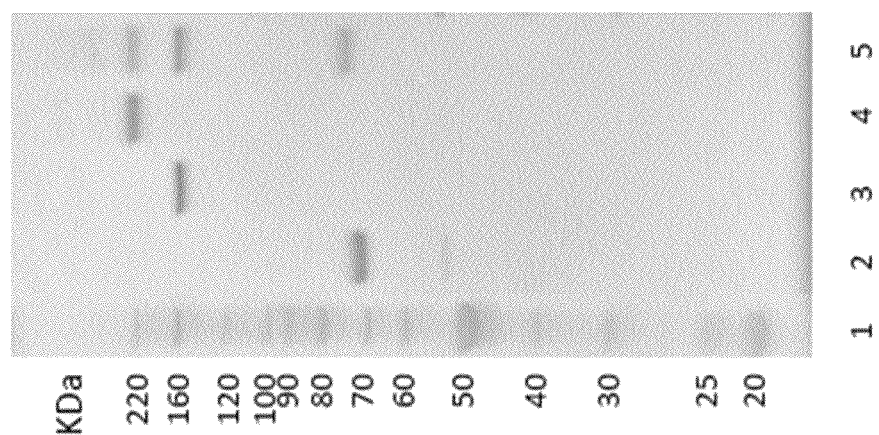
FIG. 12 shows an SDS-PAGE analysis of the purified p97-cetuximab conjugate relative to the crude reaction mixture and p97 and cetuximab alone.

For SDS-PAGE analysis, samples of purified proteins or the reaction mixture (1 μg each) were analyzed on a 4%-12% bis-tris gel with 1λ MES SDS running buffer under non-reducing conditions (Invitrogen NuPAGE® Novex® 1-12% Bis-Tris midi gel). The gel was run at a constant 125V for 150 minutes and stained with SimplyBlue™ SafeStain (Invitrogen). As shown in FIG. 12, the molecular weight of the conjugate was estimated to be about 230 KDa based on the comparison to the protein ladder molecular weight standards; this estimate is consistent with a 1:1 p97-cetuximab ratio.

For in vitro activity assays, A-431 cells are first propagated in ATCC-formulated Dulbecco's Modified Eagle's Medium including 10% FBS, and HT-29 cells are propagated in ATCC-formulated McCoy's 5a Medium Modified including 10% FBS. To ensure reliable $IC_{50}$ assay results, optimal culture conditions are verified based on cell morphology by microscopy, proliferation doubling time monitored by trypan blue exclusion assay, and cell split ratio data prior to treatment with test agents.

$IC_{50}$ assays are performed in flat bottom 96-well plates in, triplicate for each test agent concentration point and all controls at two fetal bovine serum (FBS) concentrations of 1% and 10% during the treatment incubation period of 3 days. The test agents and controls are administered to each of the cell line cultures at eight concentrations covering a 1000-fold dose range based on the $IC_{50}$ of cetuximab in related human tumor cell lines. Specifically, a total of eight test agent concentrations over a semi-logarithmic concentration scale are evaluated for each of the two test agents, cetuximab and p97-cetuximab, and the control (p97) and vehicle (PBS) in PBS at the concentrations shown in Table 10 below.

TABLE 10

| Test Articles and Controls | Test Concentrations (μg/mL) |
|---|---|
| Cetuximab (positive control) | 0.1, 0.3, 1.0, 3.0, 10, 30, 100 and 300 |
| P97-cetuximab | 0.1, 0.3, 1.0, 3.0, 10, 30, 100 and 300 |
| MTf | 0.1, 0.3, 1.0, 3.0, 10, 30, 100 and 300 |
| PBS (vehicle control) | 10% spike volume to incubation medium |

Following 72 hours incubation of the test agents in each Of the two cell cultures, MTT cytotoxicity assay are performed for evaluation of cell apoptosis according to BRI SOP: SOP-TM-GEN-029 (MTT Assay). $IC_{50}$ values and drug response curves are then generated with a SpectraMax™ M2 plate reader operated by SpectraMax™ software (Molecular Devices) and SigmaPlot™ V5.0.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A conjugate comprising a p97 polypeptide covalently or operatively linked to an antibody or antigen-binding fragment thereof that specifically binds the human Her2/neu protein, wherein the p97 polypeptide is a soluble p97 polypeptide that has a deletion of all or a portion of the hydrophobic domain as defined by residues 710-738 of SEQ ID NO: 1, and where the p97 polypeptide is effective for transporting the anti-Her2/neu antibody across the blood brain barrier.

2. The conjugate of claim 1, wherein the p97 polypeptide consists of residues 20-711 of SEQ ID NO: 1 or differs from residues 20-711 of SEQ ID NO: 1 by substitution, deletion, addition, and/or insertion of five amino acids or fewer.

3. The conjugate of claim 1, wherein the p97 polypeptide and the antibody or antigen-binding fragment are covalently linked as a fusion polypeptide.

4. The conjugate of claim 1, wherein the p97 polypeptide is covalently linked to the antibody or antigen-binding fragment with a linker.

5. The conjugate of claim 1, wherein the p97 polypeptide is (a) covalently linked to the antibody or antigen-binding fragment with a polymeric cross-linker, (b) covalently linked to the antibody or antigen-binding fragment via a nanoparticle, or (c) operatively linked to the antibody or antigen-binding fragment thereof via a liposome.

6. The conjugate of claim 1, wherein the p97 polypeptide is covalently linked to the antibody or antigen-binding fragment with a polymeric cross-linker comprising a thioether linkage.

7. The conjugate of claim 1, wherein the p97 polypeptide is covalently linked to the antibody or antigen-binding fragment with a polymeric cross-linker comprising polyethylene glycol.

8. The conjugate of claim 1, wherein the antibody or antigen-binding fragment thereof is specific for a human Her2/neu protein having a sequence set forth in SEQ ID NO: 2.

9. The conjugate of claim 1, wherein the antibody is trastuzumab or an antigen-binding fragment thereof.

10. A pharmaceutical composition comprising a conjugate of claim 1 or 9 and a pharmaceutically acceptable carrier, diluent, or excipient.

11. A method for the treatment of a subject with a Her2/neu-expressing cancer comprising administering to the subject a pharmaceutical composition of claim 10.

12. The method of claim 11, wherein the Her2/neu-expressing cancer is breast cancer, or a metastatic brain cancer.

13. The conjugate of claim 1, where the conjugate is covalently linked to a cytotoxic agent.

14. The conjugate of claim 13, where the conjugate is covalently linked to the cytotoxic agent via the antibody.

15. The conjugate of claim 14, where the cytotoxic agent is covalently linked to the antibody with a linker.

16. The conjugate of claim 13, where the conjugate is covalently linked to the cytotoxic agent via the p97 polypeptide.

17. The conjugate of claim 16, where the cytotoxic agent is covalently linked to the p97 polypeptide with a linker.

* * * * *